(12) United States Patent
Ebata

(10) Patent No.: US 11,925,404 B2
(45) Date of Patent: Mar. 12, 2024

(54) TREATMENT SYSTEM, HEATING CONTROL METHOD, AND HEATING DEVICE

(71) Applicant: OLYMPUS CORPORATION, Hachioji (JP)

(72) Inventor: Sadao Ebata, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 824 days.

(21) Appl. No.: 16/928,415

(22) Filed: Jul. 14, 2020

(65) Prior Publication Data

US 2020/0337758 A1 Oct. 29, 2020

Related U.S. Application Data

(63) Continuation of application No. PCT/JP2018/001264, filed on Jan. 17, 2018.

(51) Int. Cl.
*A61B 18/10* (2006.01)
*A61B 18/08* (2006.01)
(Continued)

(52) U.S. Cl.
CPC ............ *A61B 18/10* (2013.01); *A61B 18/085* (2013.01); *G01R 27/08* (2013.01); *H05B 1/025* (2013.01);
(Continued)

(58) Field of Classification Search
CPC .................. A61B 18/085; A61B 18/10; A61B 2018/0072; A61B 2018/00642;
(Continued)

(56) References Cited

U.S. PATENT DOCUMENTS 834,162 A * 10/1906 Northrup ................. G01K 7/20
374/185
4,196,734 A * 4/1980 Harris ................ A61B 18/1206
219/241
(Continued)

FOREIGN PATENT DOCUMENTS

JP 46-24320 B1 7/1971
JP S63-275949 A 11/1988
(Continued)

OTHER PUBLICATIONS

Apr. 17, 2018 International Search Report issued in International Patent Application No. PCT/JP2018/001264.

*Primary Examiner* — Daniel W Fowler
(74) *Attorney, Agent, or Firm* — Oliff PLC

(57) ABSTRACT

A treatment system that includes a pair of jaws and a heater resistor provided on one jaw of the pair of jaws that generates heat by energization. The system also includes a heating device that controls a current to set a resistance value of the heater resistor to a target resistance value. The heating device includes a double bridge circuit allowing current to flow between the heating device and the heater resister when detecting, by the detection resister, a difference between the resistance value of the heater resistor and the predetermined target resistance value. The heating device including a power supply voltage generator that generates a power supply voltage to be applied to the heater resistor and the double bridge circuit, a controller that modulates the generated power supply voltage, and a heater resistance detector that detects an AC component from the current flowing through the detection resistor.

20 Claims, 44 Drawing Sheets

(51) Int. Cl.
*G01R 27/08* (2006.01)
*H05B 1/02* (2006.01)
*A61B 18/00* (2006.01)
*H03K 7/08* (2006.01)

(52) U.S. Cl.
CPC .......... *A61B 2018/00714* (2013.01); *A61B 2018/0072* (2013.01); *A61B 2018/00732* (2013.01); *A61B 2018/00767* (2013.01); *A61B 2018/00827* (2013.01); *A61B 2018/00875* (2013.01); *H03K 7/08* (2013.01); *H05B 2203/035* (2013.01)

(58) Field of Classification Search
CPC .......... A61B 2018/00827; A61B 2018/00714; A61B 2018/00767; A61B 2018/00732
See application file for complete search history.

(56) References Cited

U.S. PATENT DOCUMENTS

| | | | |
|---|---|---|---|
| 2012/0265189 A1* | 10/2012 | Davis | A61B 18/02 606/22 |
| 2014/0155877 A1 | 6/2014 | Yasunaga | |
| 2016/0106492 A1* | 4/2016 | Honda | A61B 18/1442 606/52 |
| 2016/0242835 A1* | 8/2016 | Ramadhyani | A61B 18/02 |

FOREIGN PATENT DOCUMENTS

| | | |
|---|---|---|
| JP | 2012-125338 A | 7/2012 |
| JP | 2013-34568 A | 2/2013 |

\* cited by examiner

FIG.21
(a)
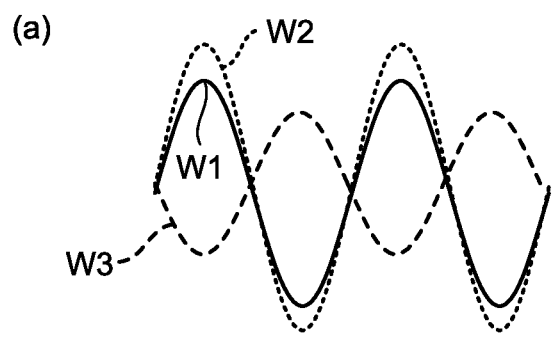
(b)
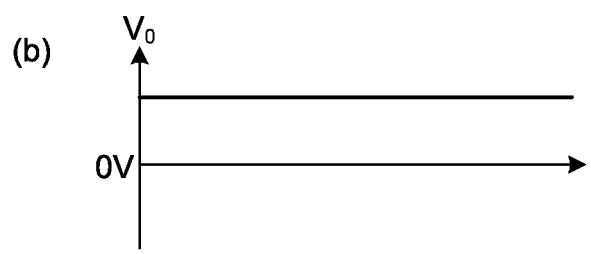
(c)
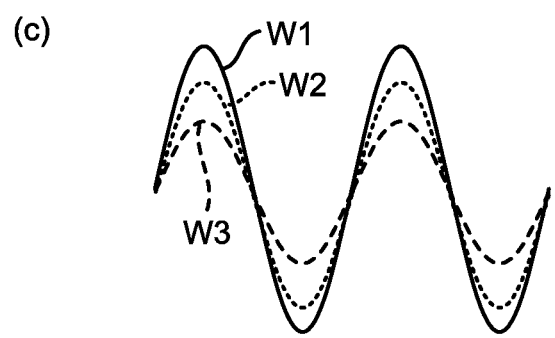
(d)

(12)

TREATMENT SYSTEM, HEATING CONTROL METHOD, AND HEATING DEVICE

CROSS-REFERENCE TO RELATED APPLICATION

This application is a continuation of International Application No. PCT/JP2018/001264, filed on Jan. 17, 2018, the entire contents of which are incorporated herein by reference.

BACKGROUND

1. Technical Field

The present disclosure relates to a treatment system, a heating control method, and a heating device.

2. Related Art

In the related art, there has been a known treatment system including a heater resistor that generates heat by energization and performs treatment (joining (or anastomosis) and dissection, or the like) on a living tissue by applying thermal energy generated by the heater resistor to the living tissue.

The conventional treatment system includes a control device (energy source) that calculates a resistance value of the heater resistor using a fall-of-potential method and controls so that the resistance value is set to a target resistance value.

Specifically, a method of calculating the resistance value of the heater resistor (fall-of-potential method) is as follows.

While applying a power supply voltage to a heater resistor and a detection resistor (monitor resistor) connected in series to the heater resistor, the control device measures a potential difference between both ends of the detection resistor and a current flowing through the detection resistor. The control device subsequently calculates a resistance value of the heater resistor on the basis of the measured potential difference and the current.

SUMMARY

In some embodiments, provided is a treatment system configured to perform treatment of a living tissue using thermal energy. The treatment system includes: a pair of jaws configured to grasp a living tissue; a heater resistor provided on one jaw of the pair of jaws, the heater resistor being configured to generate heat by energization; and a heating device electrically connected to the heater resistor, the heating device being configured to control a current to set a resistance value of the heater resistor to a predetermined target resistance value, the heating device including: a double bridge circuit having a detection resistor connected to the heater resister, the double bridge circuit allowing current to flow between the heating device and the heater resister in response to detecting, by the detection resister, a difference between the resistance value of the heater resistor and the predetermined target resistance value, a power supply voltage generator configured to generate a power supply voltage to be applied to the heater resistor and the double bridge circuit, a controller configured to modulate the generated power supply voltage, and a heater resistance detector configured to detect an alternating-current (AC) component, which is different than a direct current (DC) component, from the current flowing through the detection resistor, the DC component changing in accordance with a modulation of the power supply voltage, the AC component changing in accordance with a temperature change of the heater resistor, the controller being configured to modulate the power supply voltage based on the AC component detected by the heater resistance detector.

In some embodiments, provided is a heating control method performed by a heating device configured to heat a heater resistor that generates heat by energization. The method includes: applying a power supply voltage to the heater resistor and a double bridge circuit having a detection resistor connected to the heater resister, the double bridge circuit allowing current to flow between the heating device and the heater resister in response to detecting, by the detection resister, a difference between a resistance value of the heater resistor and a predetermined target resistance value; modulating the applied power supply voltage; and detecting an alternating-current (AC) component, which is different than a direct current (DC) component, from current flowing through the detection resistor, the DC component changing in accordance with a modulation of the power supply voltage, the AC component changing in accordance with a temperature change of the heater resistor, wherein the modulating of the power supply voltage includes performing modulation of the power supply voltage based on the AC component.

In some embodiments, a heating device includes: a heater resistor configured to generate heat by energization; a double bridge circuit having a detection resistor connected to the heater resister, the double bridge circuit allowing current to flow between the heating device and the heater resister in response to detecting, by the detection resister, a difference between a resistance value of the heater resistor and a predetermined target resistance value; a power supply voltage generator configured to generate a power supply voltage to be applied to the heater resistor and the double bridge circuit; a controller configured to modulate the generated power supply voltage; and a heater resistance detector configured to detect an alternating-current (AC) component, which is different than a direct current (DC) component, from the current flowing through the detection resistor, the DC component changing in accordance with a modulation of the power supply voltage, the AC component changing in accordance with a temperature change of the heater resistor, the controller being configured to modulate the power supply voltage based on the AC component detected by the heater resistance detector.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 21 is a diagram illustrating functions of a polarity determination unit;

DETAILED DESCRIPTION

Figure 1:
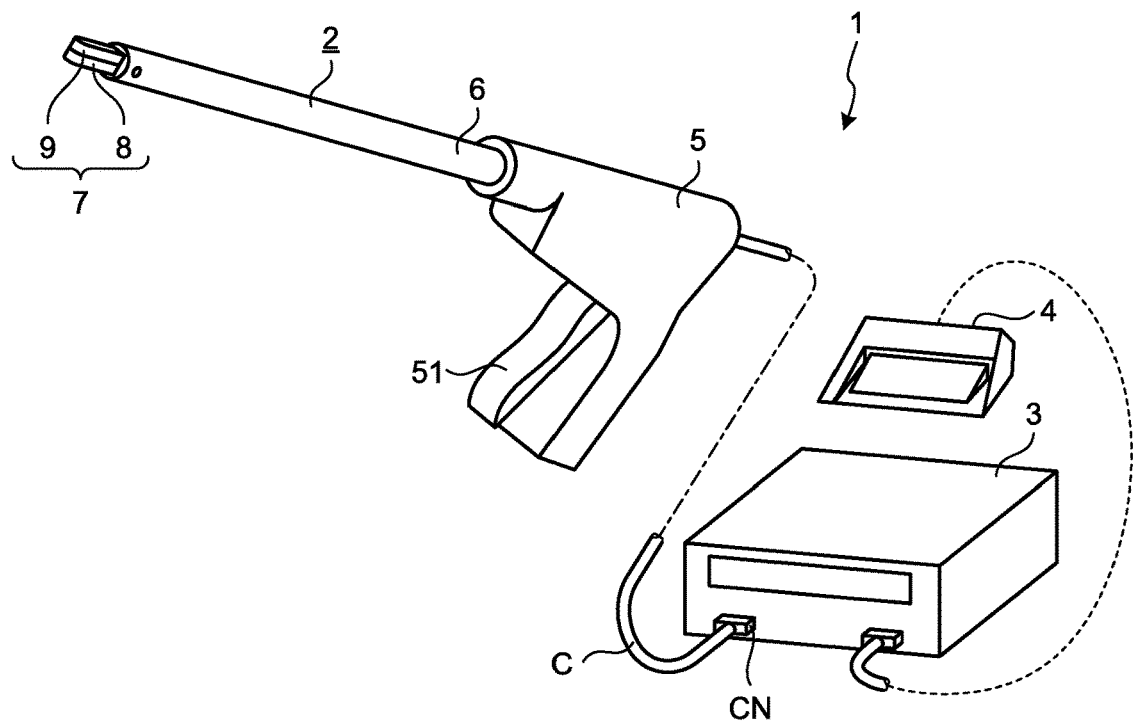
FIG. 1 is a view schematically illustrating a treatment system according to a first embodiment.

Hereinafter, modes for carrying out the disclosure (hereinafter referred to as embodiments) will be described with reference to the drawings. The disclosure is not limited to the embodiments described below. In the description of the drawings, the identical reference numerals will be used to denote identical portions.

First Embodiment

Configuration of Treatment System

FIG. 1 is a view schematically illustrating a treatment system 1 according to a first embodiment.

The treatment system 1 applies thermal energy to a living tissue as a treatment target to provide treatment (joining (or anastomosis) and dissection) to the living tissue. As illustrated in FIG. 1, the treatment system 1 includes a treatment tool 2, a control device 3, and a foot switch 4.

Configuration of Treatment Tool

The treatment tool 2 is a linear-type surgical medical treatment tool for performing treatment on a living tissue through an abdominal wall, for example. As illustrated in FIG. 1, the treatment tool 2 includes a handle 5, a shaft 6, and a grasping unit 7.

The handle 5 is a portion held by an operator by hand. As illustrated in FIG. 1, the handle 5 includes an operation knob 51.

As illustrated in FIG. 1, the shaft 6 has a substantially cylindrical shape and is, on one end (right end portion in FIG. 1), connected to the handle 5. The grasping unit 7 is attached to the other end (left end portion in FIG. 1) of the shaft 6. The shaft 6 internally includes an open-close mechanism (not illustrated) for opening and closing first and second jaws 8 and 9 (FIG. 1) constituting the grasping unit 7 in accordance with operator's operation of the operation knob 51. The shaft 6 also includes an electric cable C (FIG. 1) connected to the control device 3 via a connector CN (FIG. 1), arranged from one end (right end in FIG. 1) side to the other end side (the left end side in FIG. 1) via the handle 5.

Configuration of Grasping Unit

Figure 2:
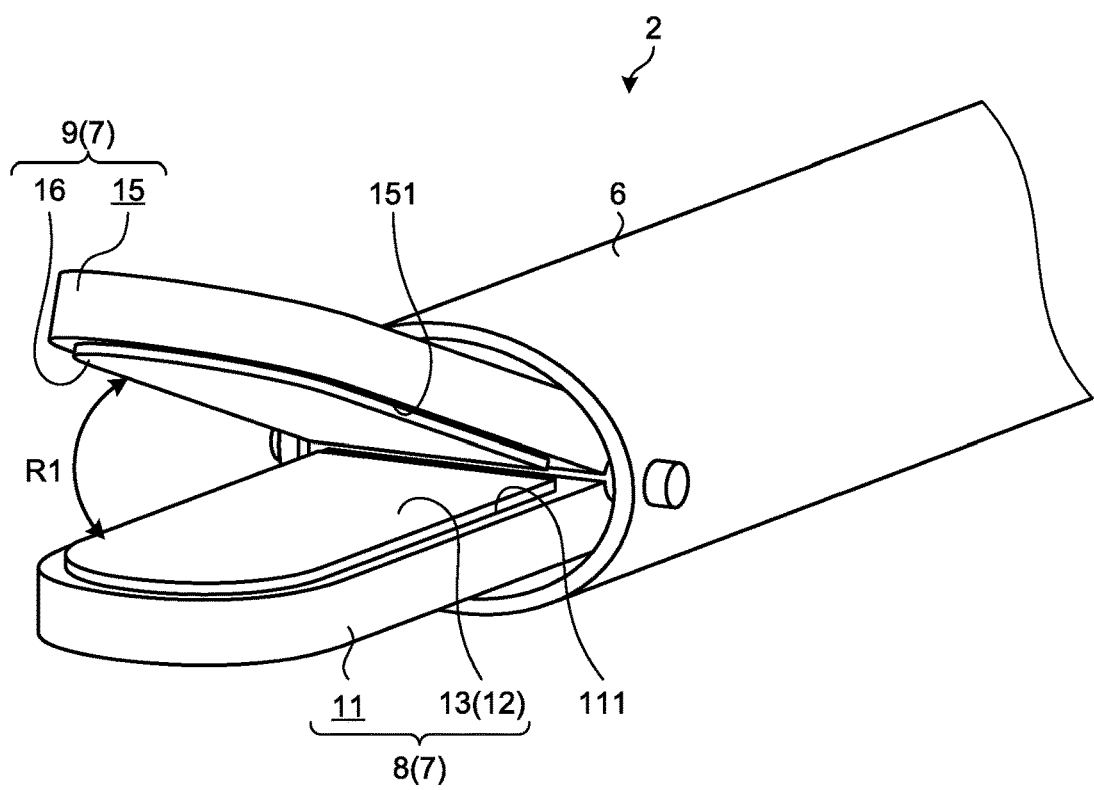
FIG. 2 is an enlarged view of a distal end portion of a treatment tool.

FIG. 2 is an enlarged view of a distal end portion of the treatment tool 2.

The grasping unit 7 is a portion that grasps a living tissue for treatment of the living tissue. The grasping unit 7 includes the first and second jaws 8 and 9 as illustrated in FIG. 1 or 2.

The first and second jaws 8 and 9 correspond to a pair of jaws according to the disclosure. The first and second jaws 8 and 9 are pivotably supported on the other end (left end portion in FIGS. 1 and 2) of the shaft 6 so as to be openable and closable in a direction of an arrow R1 (FIG. 2), enabling grasping of the living tissue in accordance with operator's operation of the operation knob 51.

Configuration of the First Jaw

Note that the "distal end side" described below is a distal end side of the grasping unit 7, corresponding to the left side in FIGS. 1 and 2. In addition, the "proximal end side" described below is the side of the shaft 6 of the grasping unit 7, corresponding to the right side in FIGS. 1 and 2.

The first jaw 8 is disposed below the second jaw 9 in FIG. 1 or 2. As illustrated in FIG. 2, the first jaw 8 includes a first cover member 11 and a heat generating structure 12.

The first cover member 11 is formed of a long plate extending in the longitudinal direction (the left-right direction in FIGS. 1 and 2) from the distal end to the proximal end of the grasping unit 7. The first cover member 11 is provided with a recess 111 formed on the upper surface in FIG. 2.

The recess 111 is located at the center of the first cover member 11 in the width direction, and extends in the longitudinal direction of the first cover member 11. Note that the illustration omits the side wall on the proximal end side, out of the side walls forming the recess 111. The first cover member 11 supports the heat generating structure 12 in the recess 111, while being supported by the shaft 6 with the recess 111 in a posture facing upward in FIG. 2.

The heat generating structure 12 is housed in the recess 111, in a state of partially projecting upward from the recess 111 in FIG. 2. The heat generating structure 12 generates thermal energy under the control of the control device 3. As illustrated in FIG. 2, the heat generating structure 12 includes a heat transfer plate 13 and a heater 14 (refer to FIG. 3).

The heat transfer plate 13 is a long plate (a long plate extending in the longitudinal direction of the grasping unit 7) formed of a material such as copper. In a state where the living tissue is grasped by the first and second jaws 8 and 9, the heat transfer plate 13 brings its upper side plate surface in FIG. 2 into contact with the living tissue, so as to transmit the heat from the heater 14 to the living tissue (apply thermal energy to the living tissue).

The heater 14 generates heat at a partial portion and functions as a sheet heater to heat the heat transfer plate 13 by the generated heat. The heater 14 has a configuration in which a heater resistor 141 (refer to FIG. 3) is provided on one plate surface of a long (long extending in the longitudinal direction of the grasping unit 7) substrate (not illustrated) formed of an insulating material such as polyimide.

The heater resistor 141 is formed of a conductive material and has a substantially U-shape as a whole that extends, on one plate surface of the substrate, to meander in a wavy manner from the proximal end side to the distal end side and is folded back at the distal end side and further extends toward the proximal end side while meandering in a wavy manner again.

The heater 14 is secured to the lower plate surface in FIG. 2 on the heat transfer plate 13 via an adhesive sheet (not illustrated) having good thermal conductivity and electrical insulation, as well as high-temperature resistance and adhesiveness.

Furthermore, the heater resistor 141 is connected, at its both ends, with a pair of lead wires C1 (refer to FIG. 3) constituting the electric cable C. The heater resistor 141 generates heat when a voltage is applied (energized) through the pair of lead wires C1 under the control of the control device 3.

Configuration of Second Jaw

The second jaw 9 includes a second cover member 15 and an opposing plate 16, as illustrated in FIG. 2.

The second cover member 15 has the same shape as the first cover member 11. That is, the second cover member 15 has a recess 151 similar to the recess 111, as illustrated in FIG. 2. The second cover member 15 supports the opposing plate 16 in the recess 151, while being supported by the shaft 6 with the recess 151 in a posture facing downward (opposing the recess 111) in FIG. 2.

The opposing plate 16 is formed of a conductive material such as copper, for example. The opposing plate 16 is formed of a flat plate having substantially the same planar shape as the recess 151, and is secured inside the recess 151. The opposing plate 16 grasps a living tissue with the heat transfer plate 13.

Material of the opposing plate 16 is not limited to a conductive material, and may be formed of another material, for example, a resin material such as polyetheretherketone (PEEK).

Configuration of Control Device and Foot Switch

Figure 3:
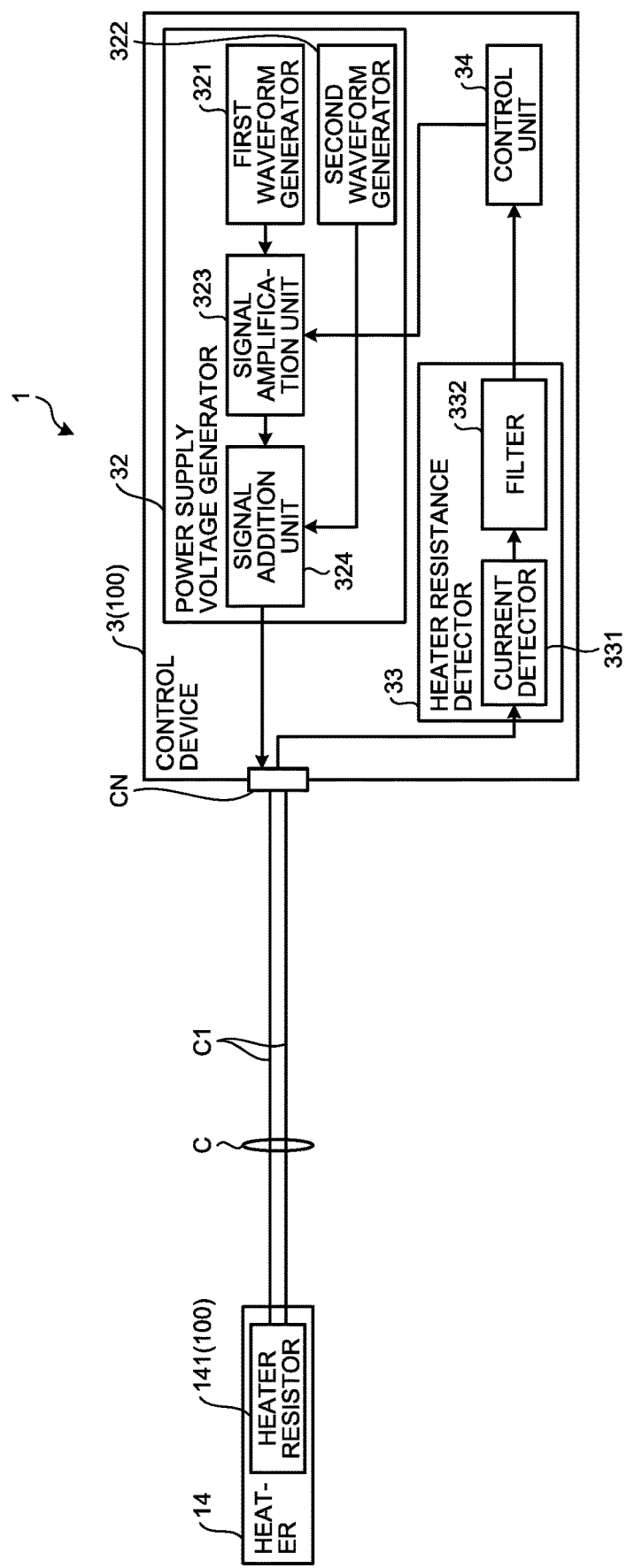
FIG. 3 is a block diagram illustrating a treatment system.
Figure 4:
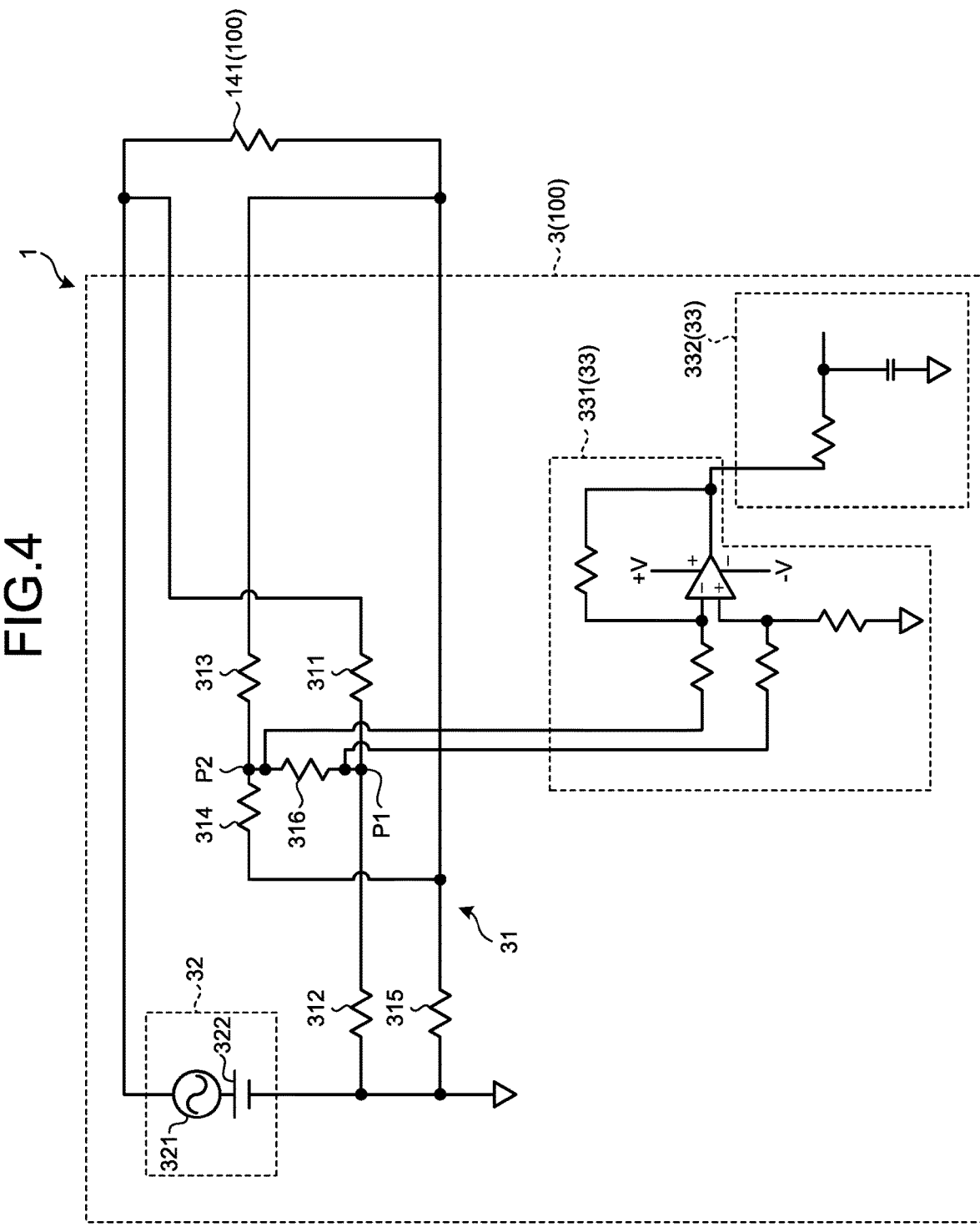
FIG. 4 is a diagram illustrating a circuit configuration of a treatment system.

FIG. 3 is a block diagram illustrating the treatment system 1. FIG. 4 is a diagram illustrating a circuit configuration of the treatment system 1. Note that FIG. 3 omits illustration of a double bridge circuit 31 for convenience of explanation. Also note that FIG. 4 omits illustration of a signal amplification unit 323, a signal addition unit 324, and a control unit 34 for convenience of explanation.

The foot switch 4 is a portion operated by an operator with one's foot. In response to the operation on the foot switch 4, the control device 3 executes heating control of the heater 14 (heater resistor 141). Note that a unit that executes heating control is not limited to the foot switch 4, and other units such as manual operation switches or the like may be employed.

The control device 3 includes a central processing unit (CPU) and controls the operation of the treatment tool 2 in accordance with a predetermined control program. As illustrated in FIG. 3 or 4, the control device 3 includes a double bridge circuit 31 (FIG. 4), a power supply voltage generator 32, a heater resistance detector 33, and a control unit 34 (FIG. 3).

The double bridge circuit 31 is a circuit that uses principles of the Wheatstone bridge and the fall-of-potential method to reduce the influence of the line resistance due to the pair of lead wires C1 or the like and the contact resistance due to the connector CN or the like in the heating control of the heater 14. As illustrated in FIG. 4, the double bridge circuit 31 includes first and second ratio arm resistors 311 and 312, first to third auxiliary ratio arm resistors 313 to 315, and a detection resistor 316.

As illustrated in FIG. 4, the first and second ratio arm resistors 311 and 312 are connected in series in order from one end across the electrodes of the power supply voltage generator 32. Furthermore, the heater resistors 141 and the first to third auxiliary ratio arm resistors 313 to 315 are connected in series from one end so as to be connected in parallel with the first and second ratio arm resistors 311 and 312, across the electrodes of the power supply voltage generator 32. Furthermore, the detection resistor 316 is connected between an intermediate point P1 in the middle of the first and second ratio arm resistors 311-312 and an intermediate point P2 in the middle of the first and second auxiliary ratio arm resistors 313-314.

In the first embodiment, individual resistance values $R_m$ and $R_n$ of the first and second ratio arm resistors 311 and 312, and individual resistance values $R_m'$, $R_n'$, and R of the first to third auxiliary ratio arm resistors 313 to 315 are preliminarily set such that the current will flow through the detection resistor 316 only when there is a difference between a resistance value $R_x$ of the heater resistor 141 and a target resistance value $R_x t$ (such that the current will not flow when there is no difference between the resistance value $R_x$ and the target resistance value $R_x t$). Note that the target resistance value $R_x t$, the resistance values $R_m$ and $R_n$ of the first and second ratio arm resistors 311 and 312, and the resistance values $R_m'$ and $R_n'$ and R of the first to third auxiliary ratio arm resistors 313 to 315 respectively have a relationship represented by the following Formula (1):

$$R_x t = \frac{R_m}{R_n} \cdot R = \frac{R_m'}{R_n'} \cdot R \quad (1)$$

The power supply voltage generator 32 generates a power supply voltage $V_1$ to be applied to the heater resistor 141 and the double bridge circuit 31. As illustrated in FIG. 3 or 4, the power supply voltage generator 32 includes first and second waveform generators 321 and 322, a signal amplification unit 323 (FIG. 3), and a signal addition unit 324 (FIG. 3).

The first waveform generator 321 generates an alternating-current (AC) voltage ($A_1 \sin(\omega t+\alpha)$) corresponding to the driving voltage according to the disclosure.

The second waveform generator 322 generates a direct-current (DC) voltage $B_1$ (constant value) corresponding to the detection voltage according to the disclosure.

The signal amplification unit 323 changes an amplitude $A_1$ (performs amplitude modulation) of the AC voltage ($A_1 \sin(\omega t+\alpha)$) generated by the first waveform generator 321 under the control of the control unit 34.

The signal addition unit 324 superimposes the AC voltage ($A_1 \sin(\omega t+\alpha)$) generated by the first waveform generator 321 and that has undergone amplitude modulation at the signal amplification unit 323 with the DC voltage $B_1$ generated by the second waveform generator 322 and thereby generates a power supply voltage $V_1$ (=$A_1 \sin(\omega t+\alpha)+B_1$).

That is, in the first embodiment, the power supply voltage $V_1$ is implemented by an AC voltage having a DC offset.

The heater resistance detector 33 includes a current detector 331 and a filter 332, as illustrated in FIG. 3 or 4.

The current detector 331 detects a current flowing through the detection resistor 316. In the first embodiment, as illustrated in FIG. 4, the current detector 331 includes an operational amplifier, for example, and converts a current flowing through the detection resistor 316 to a voltage $V_2$ (=$A_2 \cos(\omega t+\beta)+B_2$).

As illustrated in FIG. 4, the filter 332 includes a low-pass filter having a capacitor connected in parallel to the input signal and a resistor connected in series to the input signal. Subsequently, the filter 332 removes the AC component ($A_2 \cos(\omega t+\beta)$) from a detection value $V_2$ of the current detector 331, and thereby extracts a DC component $B_2$.

Subsequently, the detection value $B_2$ of the heater resistance detector 33 is output to the control unit 34.

The control unit 34 includes a CPU and a Field-Programmable Gate Array (FPGA), for example, and executes feedback control and thereby controls the heater resistor 141 to be set to a target temperature (controls the resistance value $R_x$ of the heater resistor 141 to the target resistance value $R_x t$).

Figure 5:
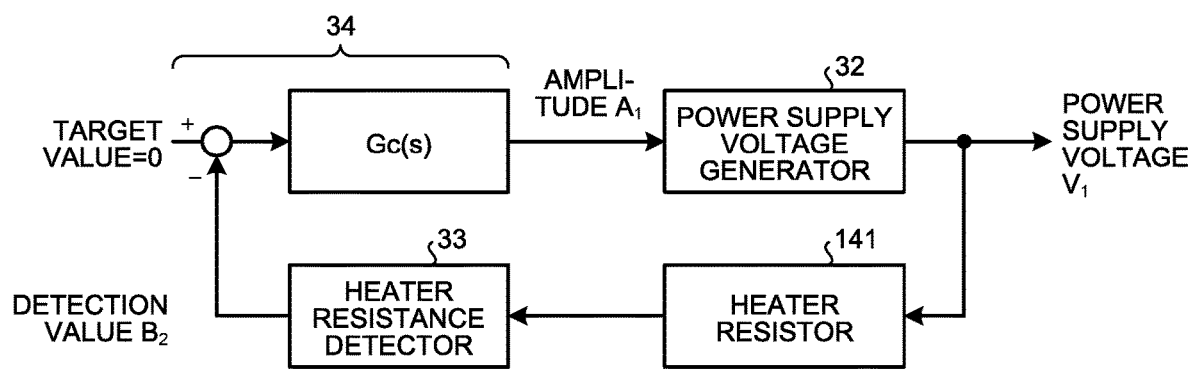
FIG. 5 is a block diagram illustrating feedback control performed by a control unit.

FIG. 5 is a block diagram illustrating feedback control performed by the control unit 34.

Specifically, the control unit 34 calculates a deviation between the detection value $B_2$ output from the heater resistance detector 33 and the target value. Here, as described above, the double bridge circuit 31 has a setting of each of the resistance value $R_m$, $R_n$, $R_m'$, $R_n'$, and R so that the current flowing through the detection resistor 316 becomes 0 in a case where there is no difference between the resistance value $R_x$ of the heater resistor 141 and the target resistance value $R_x t$. Therefore, the target value is "0". Subsequently, the control unit 34 calculates the amplitude $A_1$ of the AC voltage ($A_1 \sin(\omega t+\alpha)$) on the basis of the calculated deviation, and then outputs the calculated amplitude $A_1$ to the power supply voltage generator 32 (the signal amplification unit 323) as a control target. In response to this, the power supply voltage generator 32 applies the power supply voltage $V_1$ having the amplitude $A_1$ calculated by the control unit 34 to the heater resistor 141 and the double bridge circuit 31. That is, in the first embodiment, the control unit 34 performs amplitude modulation on the power supply voltage $V_1$ (AC voltage ($A_1 \sin(\omega t+\alpha)$) via the signal amplification unit 323.

The heater resistor 141 and the control device 3 described above correspond to a heating device 100 (FIGS. 3 and 4) according to the disclosure.

Heating Control Method

Next, operation (a heating control method) of the above-described treatment system 1 will be described.

Figure 6:
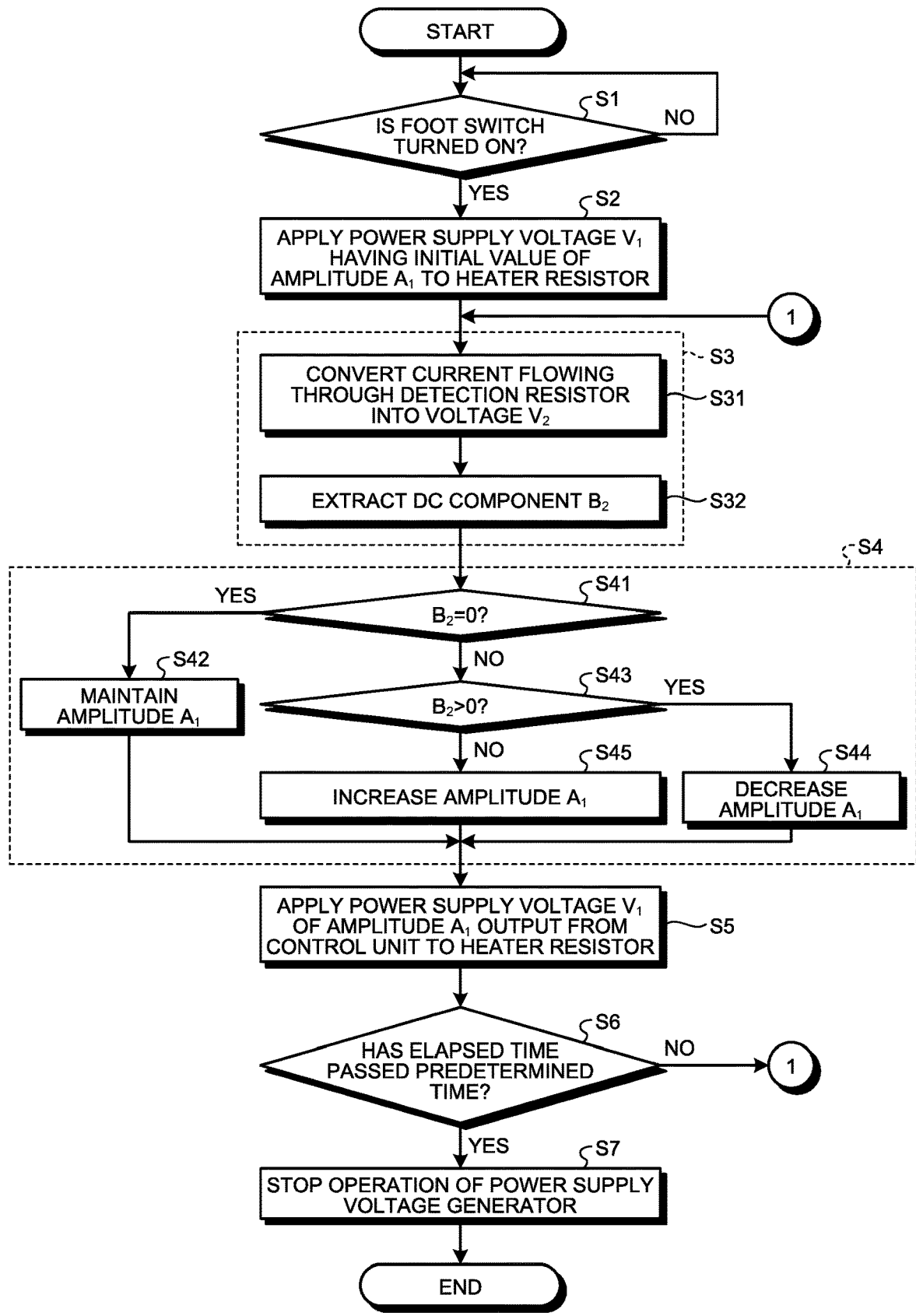
FIG. 6 is a flowchart illustrating a heating control method.

FIG. 6 is a flowchart illustrating a heating control method.

The operator holds the treatment tool 2 by hand and inserts the distal end portion (the grasping unit 7 and a part of the shaft 6) of the treatment tool 2 into the abdominal cavity through the abdominal wall using a trocar, for example. Furthermore, the operator operates the operation knob 51 to grasp the living tissue as a treatment target with the grasping unit 7.

Subsequently, the control device 3 executes the following heating control in accordance with operator's operation of the foot switch 4 (Step S1: Yes).

First, the control unit 34 outputs an initial value of the amplitude $A_1$ of the AC voltage ($A_1 \sin(\omega t+\alpha)$) to the power supply voltage generator 32 (signal amplification unit 323). Subsequently, the power supply voltage generator 32 applies the power supply voltage $V_1$ having the initial value of the amplitude $A_1$ to the heater resistor 141 and the double bridge circuit 31 (Step S2).

After Step S2, the heater resistance detector 33 calculates the detection value $B_2$ and then outputs the calculated value to the control unit 34 (Step S3).

Specifically, the current detector 331 converts the current flowing through the detection resistor 316 into a voltage $V_2$ (=$A_2 \cos(\omega t+\beta)+B_2$) (Step S31).

After Step S31, the filter 332 removes the AC component ($A_2 \cos(\omega t+\beta)$) from the detection value $V_2$ of the current detector 331, and thereby extracts the DC component $B_2$ (Step S32).

After Step S3, the control unit 34 calculates the amplitude $A_1$ of the AC voltage ($A_1 \sin(\omega t+\alpha)$) on the basis of the deviation between the detection value $B_2$ output from the heater resistance detector 33 and the target value "0" (Step S4).

Figure 7:
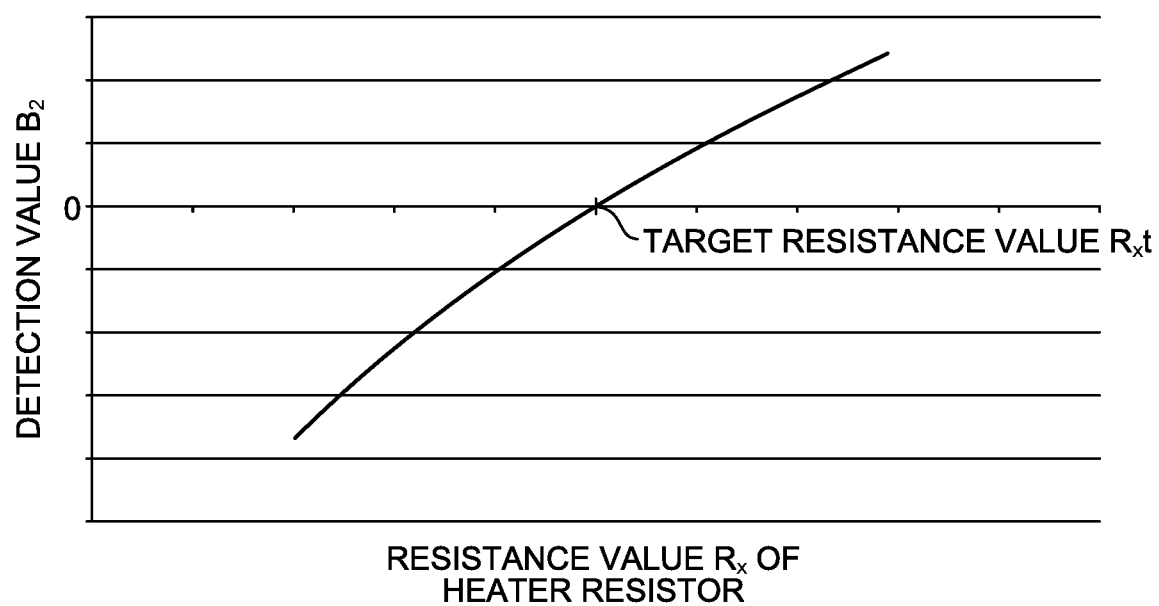
FIG. 7 is a diagram illustrating a relationship between a resistance value of a heater resistor and a detection value.

FIG. 7 is a diagram illustrating a relationship between the resistance value $R_x$ of the heater resistor 141 and the detection value $B_2$.

Here, there is a relationship illustrated in FIG. 7 between the resistance value $R_x$ of the heater resistor 141 (corresponding to the temperature of the heater resistor 141 (hereinafter, referred to as heater temperature)) and the detection value $B_2$.

Specifically, in a case where the detection value $B_2$ is "0", the resistance value $R_x$ of the heater resistor 141 matches the target resistance value $R_x t$. In other words, the heater temperature matches the target temperature. In contrast, the greater the detection value $B_2$ with respect to "0", the greater the resistance value $R_x$ of the heater resistor 141 with respect to the target resistance value $R_x t$. In other words, the heater temperature will exceed the target temperature. Moreover, the smaller the detection value $B_2$ with respect to "0", the smaller the resistance value $R_x$ of the heater resistor 141 with respect to the target resistance value $R_x t$. In other words, the heater temperature is lowered below the target temperature.

In Step S4, the amplitude $A_1$ is calculated on the basis of the deviation between the detection value $B_2$ and the target value "0" in consideration of the relationship illustrated in FIG. 7.

Specifically, first, the control unit 34 judges whether the detection value $B_2$ output from the heater resistance detector 33 matches the target value "0" (whether the detection value $B_2$ is "0") (Step S41).

In a case where the detection value $B_2$ is judged to be "0" (Step S41: Yes), the control unit 34 judges that the resistance value $R_x$ of the heater resistor 141 has reached the target resistance value $R_x t$ (the heater temperature has reached the target temperature). Subsequently, the control unit 34 maintains the amplitude $A_1$ calculated in the immediately preceding loop (the loop of Steps S3 to S6) (Step S42), and outputs the maintained amplitude $A_1$ to the power supply voltage generator 32 (the signal amplification unit 323).

In contrast, in a case where the detection value $B_2$ is judged not to be "0" (Step S41: No), the control unit 34 judges whether the detection value $B_2$ is greater than "0" (Step S43).

In a case where the detection value $B_2$ is judged to greater than "0" (Step S43: Yes), the control unit 34 judges that the resistance value $R_x$ of the heater resistor 141 is greater than the target resistance value $R_x t$ (the heater temperature is higher than the target temperature). Subsequently, in order to reduce the heater temperature, the control unit 34 changes the amplitude $A_1$ of the AC voltage ($A_1 \sin(\omega t+\alpha)$) so as to be smaller than the amplitude $A_1$ calculated in the immediately preceding loop in accordance with the deviation between the detection value $B_2$ and the target value "0" (Step S44), and then outputs the reduced amplitude $A_1$ to the power supply voltage generator 32 (signal amplification unit 323).

In contrast, in a case where the detection value $B_2$ is judged to smaller than "0" (Step S43: No), the control unit 34 judges that the resistance value $R_x$ of the heater resistor 141 is smaller than the target resistance value $R_x t$ (the heater temperature is lower than the target temperature). Subsequently, in order to increase the heater temperature, the control unit 34 changes the amplitude $A_1$ of the AC voltage ($A_1 \sin(\omega t+\alpha)$) so as to be greater than the amplitude $A_1$ calculated in the immediately preceding loop in accordance with the deviation between the detection value $B_2$ and the target value "0" (Step S45), and outputs the increased amplitude $A_1$ to the power supply voltage generator 32 (signal amplification unit 323).

After Step S42, Step S44, or Step S45, the power supply voltage generator 32 applies the power supply voltage $V_1$ having the amplitude $A_1$ output from the control unit 34 in Step S42, Step S44, or Step S45 to the heater resistor 141 and the double bridge circuit 31 (Step S5).

After Step S5, the control unit 54 constantly monitors whether the elapsed time since the start of the heating control (the elapsed time since the foot switch 4 is operated in Step S1) has reached a predetermined time (Step S6).

In a case where it is judged that the elapsed time since the start of the heating control has not reached the predetermined time (Step S6: No), the treatment system 1 returns to Step S3.

In contrast, in a case where it is judged that the elapsed time since the start of the heating control has reached the predetermined time (Step S6: Yes), the control unit 34 stops operation of the power supply voltage generator 32 (stops application of the power supply voltage $V_1$ to the heater resistor 141 and the double bridge circuit 31 (Step S7).

Transition of Power Supply Voltage and Detection Value of Heater Resistance Detector The following is a description of an example of a transition of the power supply voltage $V_1$ and the detection value $B_2$ of the heater resistance detector 33 obtained by the above-described heating control method.

Figure 8:
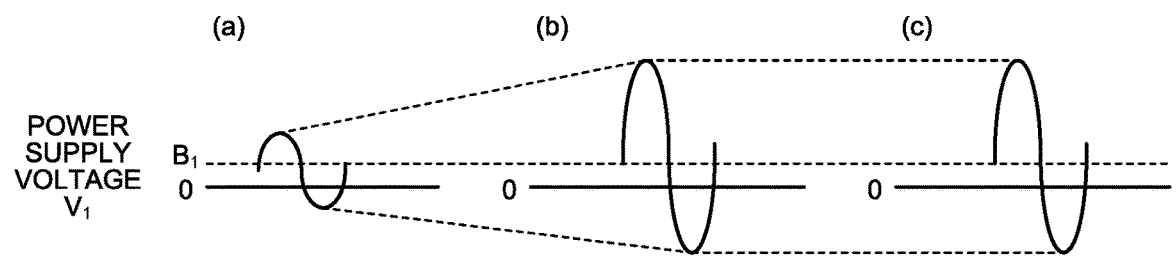
FIG. 8 is a diagram illustrating a transition of a power supply voltage.
Figure 9:
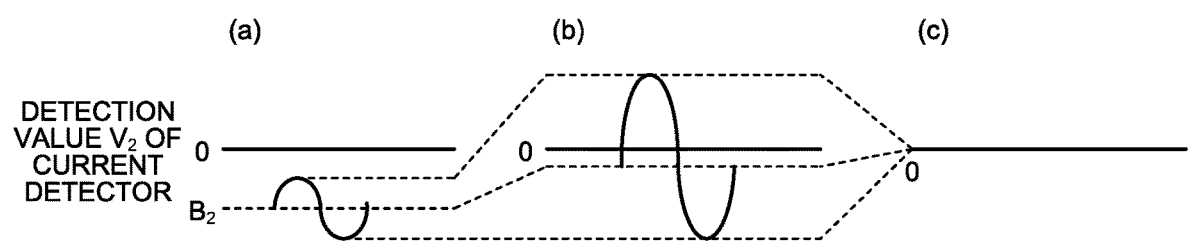
FIG. 9 is a diagram illustrating a transition of an output value of a current detector.
Figure 10:
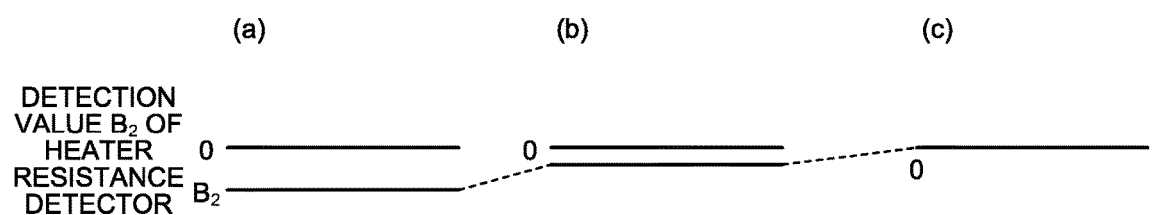
FIG. 10 is a diagram illustrating a transition of a detection value of a heater resistance detector.

FIG. 8 is a diagram illustrating a transition of the power supply voltage $V_1$. FIG. 9 is a diagram illustrating a transition of the detection value $V_2$ of the current detector 331. FIG. 10 is a diagram illustrating a transition of the detection value $B_2$ of the heater resistance detector 33. Note that (a) of FIG. 8, (a) of FIG. 9, and (a) of FIG. 10 illustrate a case where the resistance value $R_x$ of the heater resistor 141 is sufficiently smaller than the target resistance value $R_x t$ (a case where the heater temperature is sufficiently lower than the target temperature). (b) of FIG. 8, (b) of FIG. 9, and (b) of FIG. 10 illustrate a case where the resistance value $R_x$ of the heater resistor 141 approaches the target resistance value $R_x t$ (a case where the heater temperature approaches the target temperature) as a result of heating control, compared with the states illustrated in (a) of FIG. 8, (a) of FIG. 9, and (a) of FIG. 10. (c) of FIG. 8, (c) of FIG. 9, and (c) of FIG. 10 illustrate a case where the resistance value $R_x$ of the heater resistor 141 matches the target resistance value $R_x t$ (a case where the heater temperature matches the target temperature) as a result of heating control.

As observed in comparison between (a) of FIG. 8 and (b) of FIG. 8, in a case where the resistance value $R_x$ of the heater resistor 141 is smaller than the target resistance value $R_x t$ (the heater temperature is lower than the target temperature, the power supply voltage $V_1$ is set such that the amplitude $A_1$ will be increased by the processes in Steps S45 and S5 in order to increase the resistance value $R_x$ of the heater resistor 141 (increase the heater temperature). In a case where the resistance value $R_x$ of the heater resistor 141 matches the target resistance value $R_x t$ (in a case where the heater temperature matches the target temperature) as illustrated in (c) of FIG. 8, the power supply voltage $V_1$ is set to be maintained to have the amplitude $A_1$ ((b) of FIG. 8) of the power supply voltage $V_1$ in the immediately preceding loop by the processes in Steps S42 and S5.

As illustrated in (a) and (b) of FIG. 9 ((a) and (b) of FIG. 10), the DC component $B_2$ (detection value $B_2$) of the detection value $V_2$ of the current detector 331 takes a negative value in a case where the resistance value $R_x$ of the heater resistor 141 is smaller than the target resistance value $R_x t$ (in a case where the heater temperature is lower than the target temperature). In addition, the DC component $B_2$ (detection value $B_2$) approaches the target value "0" as the resistance value $R_x$ of the heater resistor 141 approaches the target resistance value $R_x t$ (as the heater temperature approaches the target temperature) by the processes of Steps S45 and S5. Furthermore, as illustrated in (c) of FIG. 9 ((c) of FIG. 10), the DC component $B_2$ (detection value $B_2$) indicates the target value "0" in a case where the resistance value $R_x$ of the heater resistor 141 matches the target resistance value $R_x t$ (in a case where the heater temperature matches the target temperature).

Here, as observed in comparison of (a) and (b) of FIG. 8 with (a) and (b) of FIG. 9, the AC component ($A_2 \cos(\omega t+\beta)$) of the detection value $V_2$ of the current detector 331 changes in accordance with the amplitude modulation of the power supply voltage $V_1$. Therefore, the AC component ($A_2 \cos(\omega t+\beta)$) corresponds to a first current component according to the disclosure. In contrast, as observed in comparison of (a) to (c) of FIG. 8 with (a) to (c) of FIG. 9 ((a) to (c) of FIG. 10), the DC component $B_2$ (the detection value $B_2$) of the detection value $V_2$ of the current detector 331 would not change in accordance with the amplitude modulation of the power supply voltage $V_1$, but would change in accordance with the change in the heater temperature (change in the resistance value $R_x$ of the heater resistor 141). Therefore, the detection value $B_2$ corresponds to a second current component according to the disclosure.

According to the first embodiment described above, the following effects are obtained.

The heating device 100 according to the first embodiment is provided with the double bridge circuit 31 including the detection resistor 316 connected to the heater resistor 141 such that current flows only when there is a difference between the resistance value $R_x$ and the target resistance value $R_x t$ on the heater resistor 141. Therefore, even when there is line resistance due to the pair of lead wires C1 or the like and contact resistance due to the connector CN or the like, execution of feedback control to change (performing amplitude modulation of) the power supply voltage $V_1$ so that the current flowing through the detection resistor 316 becomes "0" will make it possible to control the heater temperature to the target temperature with high accuracy.

In particular, the heating device 100 according to the first embodiment detects the DC component $B_2$ (detection value $B_2$) that changes in accordance with the change in the heater temperature, other than the AC component ($A_2 \cos(\omega t+\beta)$) that changes in accordance with the amplitude modulation of the power supply voltage $V_1$ in the detection value $V_2$ of the current detector 331. Subsequently, the heating device 100 performs amplitude modulation on the power supply voltage $V_1$ on the basis of the DC component $B_2$ (detection value $B_2$). For this reason, the feedback control can be performed with high accuracy using the detection value $B_2$ which is not affected by the fluctuation of the power supply voltage $V_1$.

Furthermore, since the DC component $B_2$ is used as the second current component according to the disclosure, there is no need to perform smoothing using rectification or integration. This makes it possible to simplify the circuit configuration of the heater resistance detector 33.

Modification 1-1 of First Embodiment

Figure 11:
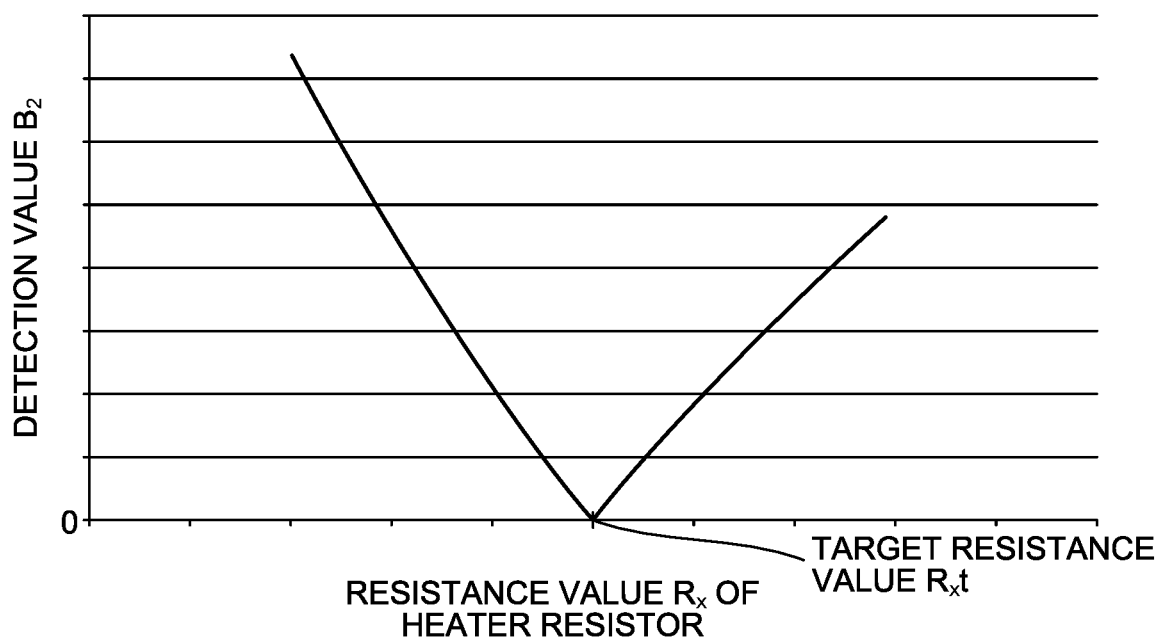
FIG. 11 is a diagram illustrating modification 1-1 of the first embodiment.
Figure 12:
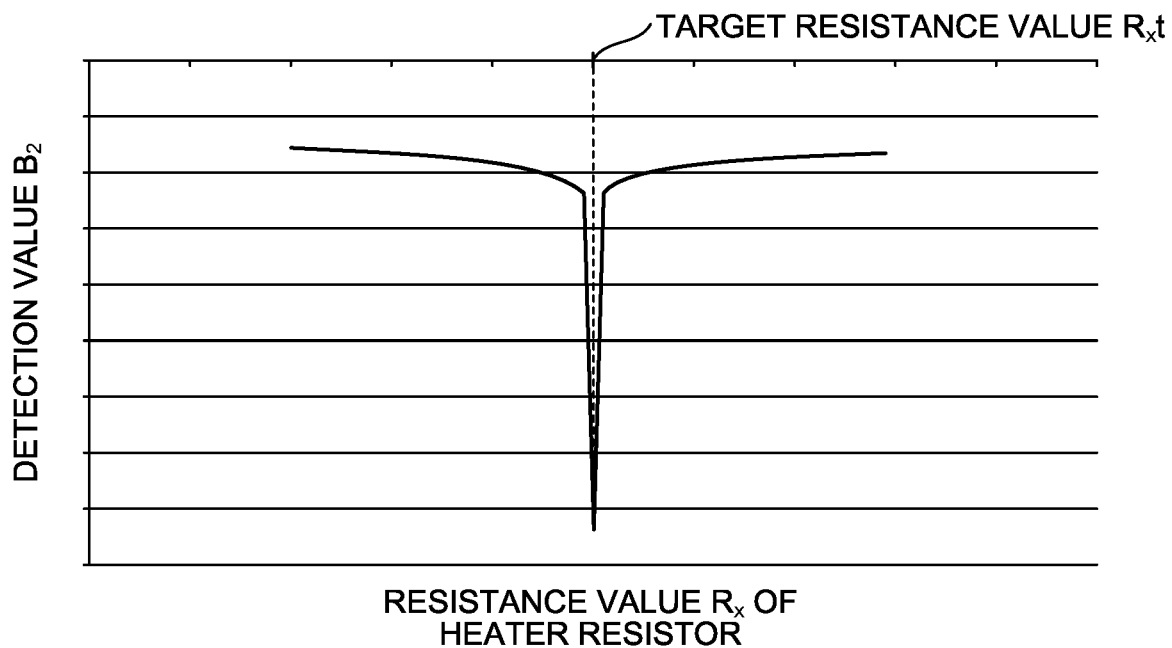
FIG. 12 is a diagram illustrating modification 1-1 of the first embodiment.
Figure 13:
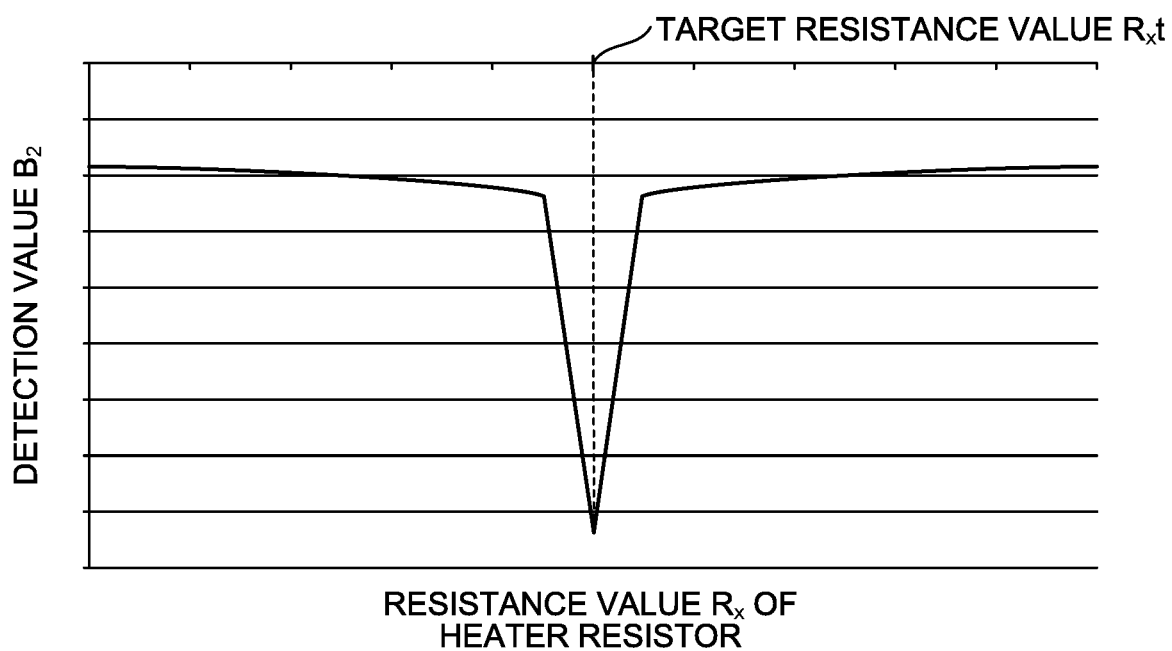
FIG. 13 is a diagram illustrating modification 1-1 of the first embodiment.

FIG. 11 to FIG. 13 are diagrams illustrating modification 1-1 of the first embodiment. Specifically, FIG. 11 is a diagram in which the detection value $B_2$ illustrated in FIG. 7 is represented by an absolute value. FIG. 12 is a logarithmic diagram of the absolute value of the detection value $B_2$ illustrated in FIG. 11. FIG. 13 is an enlarged view of the range on the horizontal axis in FIG. 12.

In the first embodiment described above, the following process may be executed in order to judge whether the detection value $B_2$ is "0" with high accuracy.

Specifically, as illustrated in FIG. 11, the control unit 34 obtains the absolute value of the detection value $B_2$. Furthermore, as illustrated in FIG. 12 or 13, the control unit 34 obtains the logarithm of the absolute value of the detection value $B_2$. Subsequently, in a case where the absolute value of the logarithmic detection value $B_2$ is a local minimum, the control unit 34 judges that the detection value $B_2$ is "0".

Modification 1-2 of First Embodiment

Figure 14:
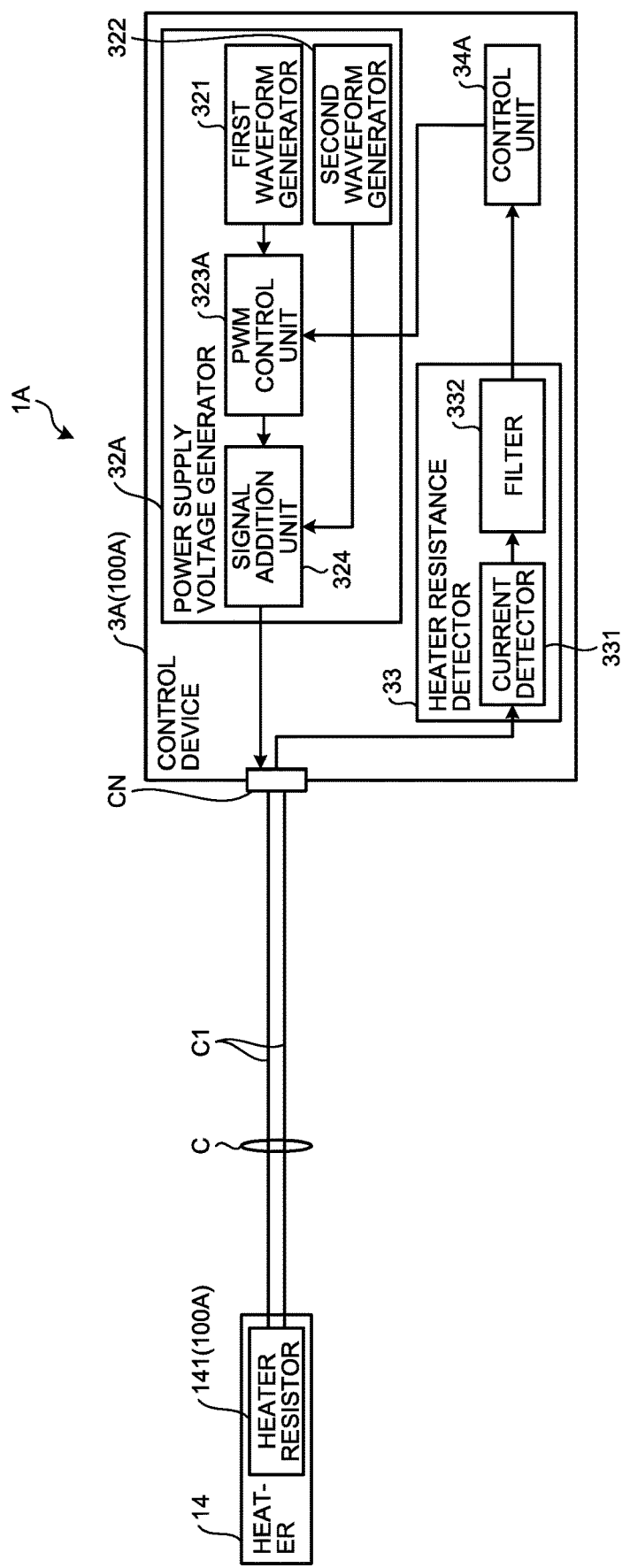
FIG. 14 is a diagram illustrating modification 1-2 of the first embodiment.
Figure 15:
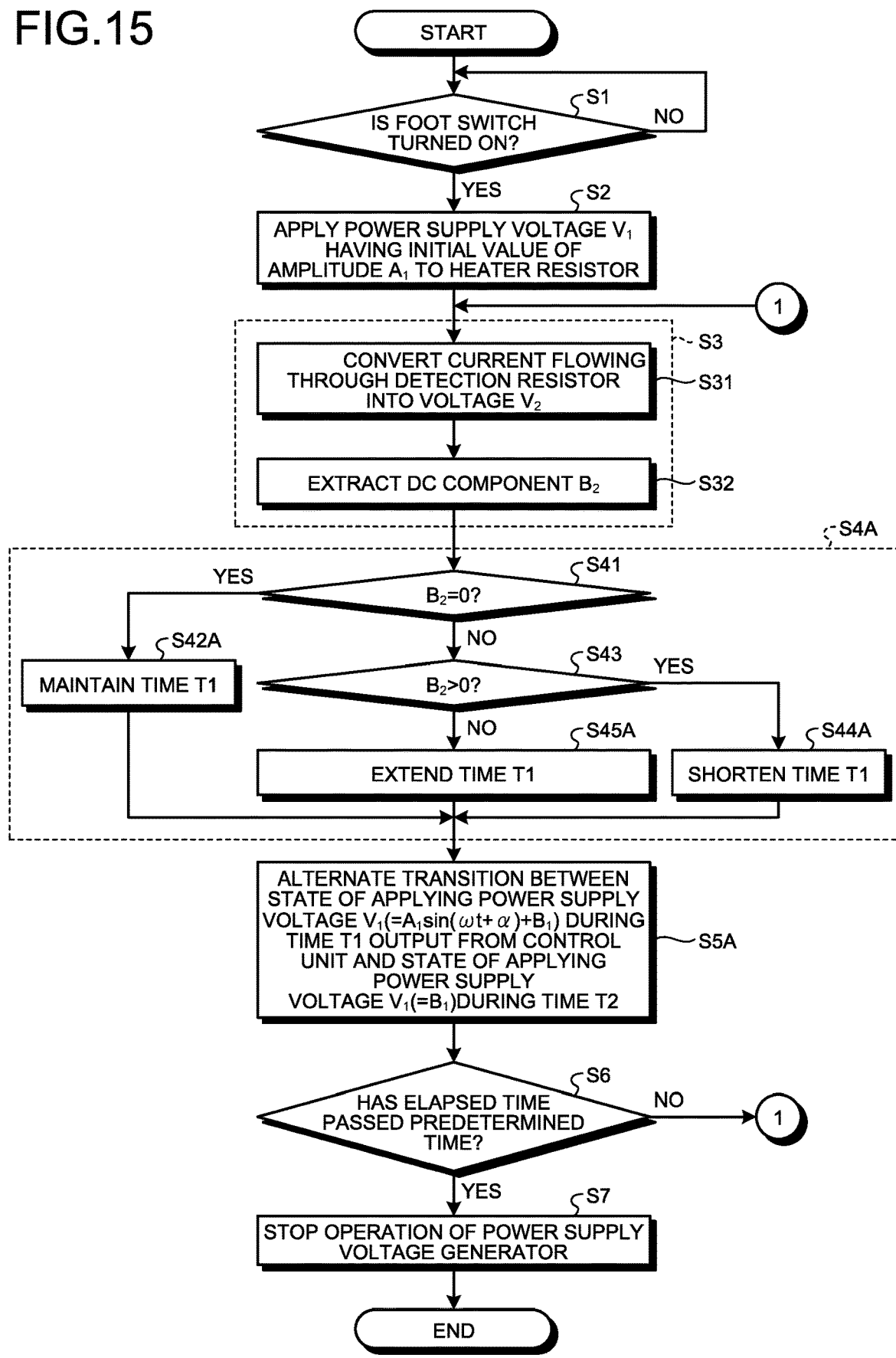
FIG. 15 is a diagram illustrating modification 1-2 of the first embodiment.
Figure 16:
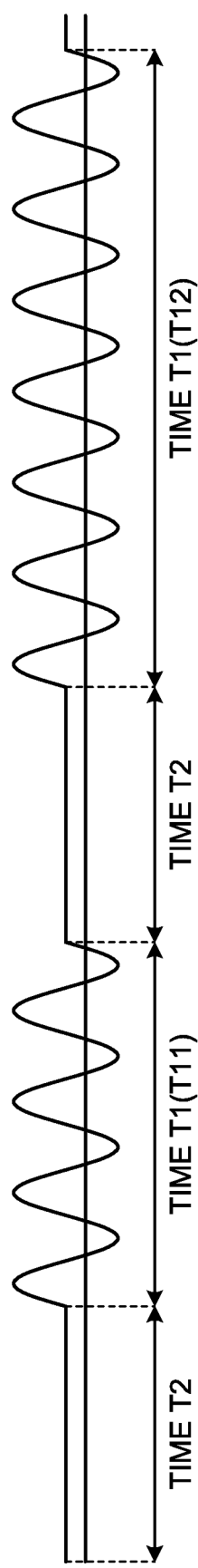
FIG. 16 is a diagram illustrating modification 1-2 of the first embodiment.

FIG. 14 to FIG. 16 are diagrams illustrating modification 1-2 of the first embodiment. Specifically, FIG. 14 is a block diagram illustrating a treatment system 1A according to modification 1-2. FIG. 15 is a flowchart illustrating a heating control method according to modification 1-2. FIG. 16 is a diagram illustrating a waveform of the power supply voltage $V_1$ according to modification 1-2.

As illustrated in FIG. 14, the treatment system 1A (a control device 3A) according to modification 1-2 employs a power supply voltage generator 32A equipped with a PWM control unit 323A instead of the signal amplification unit 323, and employs a control unit 34A having a function different from the control unit 34, compared to the treatment system 1 described above in the first embodiment.

Under the control of the control unit 34A, the PWM control unit 323A changes a period of time T1 (FIG. 16) for outputting the AC voltage ($A_1 \sin(\omega t+\alpha)$) generated by the first waveform generator 321 to the signal addition unit 324. In other words, the PWM control unit 323A performs pulse width modulation on the AC voltage ($A_1 \sin(\omega t+\alpha)$). Furthermore, after the time T1, the PWM control unit 323A does not output the AC voltage ($A_1 \sin(\omega t+\alpha)$) to the signal addition unit 324 during a fixed period of time T2 (FIG. 16). Subsequently, the PWM control unit 323A alternates transition between a state of outputting the AC voltage ($A_1 \sin(\omega t+\alpha)$) during the time T1 and a state of not outputting the AC voltage ($A_1 \sin(\omega t+\alpha)$) during the time T2 to the signal addition unit 324 (FIG. 16).

Note that, during the time T1, the signal addition unit 324 superimposes the AC voltage ($A_1 \sin(\omega t+\alpha)$) generated by the first waveform generator 321 and that has undergone pulse width modulation at the PWM control unit 323A with the DC voltage $B_1$ generated by the second waveform generator 322, and thereby generates a power supply voltage $V_1$ ($=A_1 \sin(\omega t+\alpha)+B_1$). On the other hand, during time T2, the signal addition unit 324 outputs the DC voltage $B_1$ generated by the second waveform generator 322, as the power supply voltage $V_1$ ($=B_1$).

Similarly to the control unit 34 described above in the first embodiment, the control unit 34A calculates the deviation between the detection value $B_2$ output from the heater resistance detector 33 and the target value "0". Subsequently, the control unit 34A changes the above-described time T1 on the basis of the calculated deviation. That is, the control unit 34A performs, in modification 1-2, pulse width modulation on the power supply voltage $V_1$ (AC voltage ($A_1$ sin($\omega t+\alpha$)) via the PWM control unit 323A.

The heater resistor 141 and the control device 3A described above correspond to a heating device 100A (FIG. 14) according to the disclosure.

Next, a heating control method according to modification 1-2 will be described.

As illustrated in FIG. 15, the heating control method according to modification 1-2 employs Steps S4A and S5A instead of Steps S4 and S5, with respect to the heating control method described above in the first embodiment. Therefore, Steps S4A and S5A alone will be described below.

In Step S4A, the control unit 34A calculates the time T1 on the basis of the deviation between the detection value $B_2$ output from the heater resistance detector 33 and the target value "0" in consideration of the relationship illustrated in FIG. 7.

Note that Step S4A includes Steps S41, S42A, S43, S44A, and S45A similar to Steps S41 to S45 in Step S4 described above in the first embodiment. Here, Steps S42A, S44A, and S45A are different from Steps S42, S44, and S45 respectively only in that the change target has been changed from amplitude $A_1$ to the time T1 along with the change from amplitude modulation to pulse width modulation.

For example, in Step S44A, the control unit 34A sets the time T1 shorter than the time T1 calculated at the immediately preceding loop (loop including Steps S3, S4A, S5A, and S6) in accordance with the deviation between the detection value $B_2$ and the target value "0" in order to reduce the heater temperature, and then outputs the shortened time T1 (for example, time T11 (FIG. 16)) to the power supply voltage generator 32A (PWM control unit 323A).

Furthermore, for example, in Step S45A, the control unit 34A extends the time T1 to be longer than the time T1 calculated in the immediately preceding loop in accordance with the deviation between the detection value $B_2$ and the target value "0" in order to increase the heater temperature, and then outputs the extended time T1 (for example, time T12 (FIG. 16)) to the power supply voltage generator 32A (PWM control unit 323A).

After Steps S42A, S44A, or S45A, the power supply voltage generator 32A performs, in Step S5A, for the heater resistor 141 and the double bridge circuit 31, alternate transition between a state of applying the power supply voltage $V_1$ (=$A_1$ sin($\omega t+\alpha$)+$B_1$) obtained by superimposing the AC voltage ($A_1$ sin($\omega t+\alpha$)) with the DC voltage $B_1$ during the time T1 output from the control unit 34 in Steps S42A, S44A, or S45A, and a state of applying the power supply voltage $V_1$ (=$B_1$) which is the DC voltage $B_1$ during the time T2 (FIG. 16). Thereafter, the treatment system 1A proceeds to Step S6.

It is also possible to have an effect similar to the above-described first embodiment even in the case of employing the configuration in which pulse width modulation is performed on the power supply voltage $V_1$ (AC voltage ($A_1$ sin($\omega t+\alpha$)) as in the above-described modification 1-2.

Modification 1-3 of First Embodiment

Figure 17:
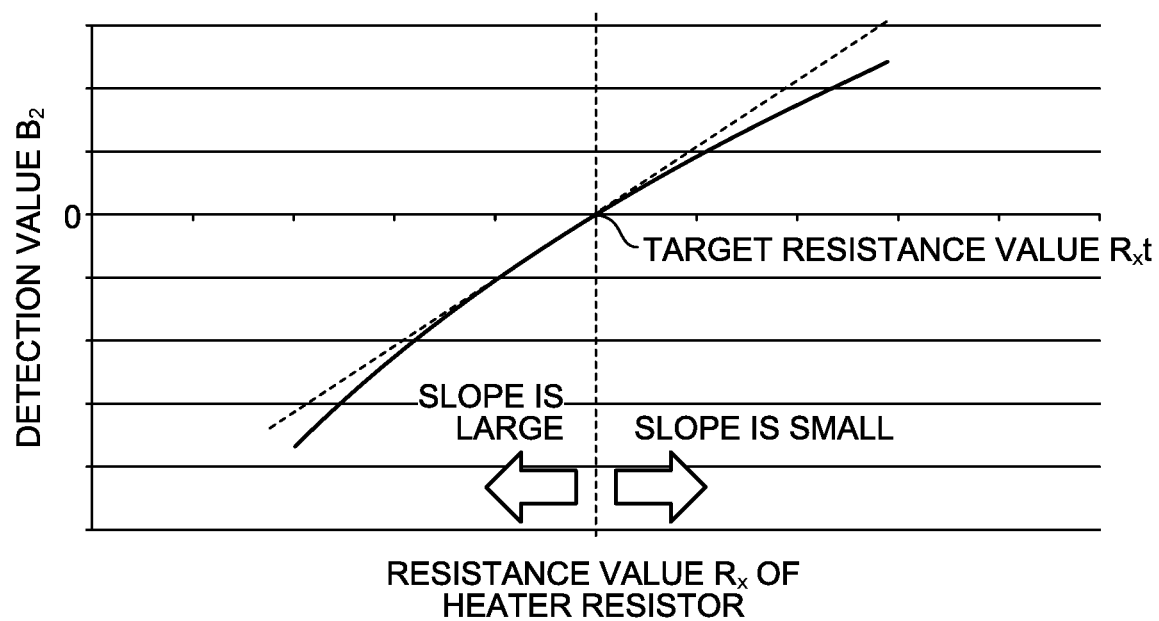
FIG. 17 is a diagram illustrating modification 1-3 of the first embodiment.

FIG. 17 is a diagram illustrating modification 1-3 of the first embodiment. Specifically, FIG. 17 is a diagram that corresponds to FIG. 7.

Meanwhile, the relationship between the resistance value $R_x$ of the heater resistor 141 and the detection value $B_2$ is not a linear relationship as illustrated in FIG. 17. Specifically, the ratio (slope) of the increase (or decrease) of the detection value $B_2$ to a constant increase (or decrease) of the resistance value $R_x$ of the heater resistor 141 in a case where the resistance value $R_x$ is greater than the target resistance value $R_x t$ (where the detection value $B_2$ is greater than 0) is smaller than the ratio (slope) of the increase (decrease) of the detection value $B_2$ to a constant increase (or decrease) of the resistance value $R_x$ in a case where the resistance value $R_x$ is smaller than the target resistance value $R_x t$ (where the detection value $B_2$ is smaller than 0).

That is, in the case where the resistance value $R_x$ of the heater resistor 141 is smaller than the target resistance value $R_x t$, the resistance value $R_x$ is likely to converge to the target resistance value $R_x t$ more rapidly than the case where the resistance value $R_x$ is greater than the target resistance value $R_x t$. Therefore, in consideration of the convergence of the resistance value $R_x$ of the heater resistor 141 to the target resistance value $R_x t$, it is not preferable to set a control proportional gain Gc(s) to the same level between the case where the resistance value $R_x$ is greater than the target resistance value $R_x t$ (where the detection value $B_2$ is greater than 0) and the case where the resistance value $R_x$ is smaller than the target resistance value $R_x t$ (where the detection value $B_2$ is smaller than 0).

Therefore, Steps S44 and S45 may be executed as described below in the above-described first embodiment.

In Step S44, since the detection value $B_2$ is greater than "0" (the resistance value $R_x$ of the heater resistor 141 is greater than the target resistance value $R_x t$), the control unit 34 sets the amplitude $A_1$ of the AC voltage ($A_1$ sin($\omega t+\alpha$)), by a relatively large decrease, to be smaller than the amplitude $A_1$ calculated in the immediately preceding loop (so as to increase the control proportional gain Gc(s)).

In contrast, in Step S45, since the detection value $B_2$ is smaller than "0" (the resistance value $R_x$ of the heater resistor 141 is smaller than the target resistance value $R_x t$), the control unit 34 sets the amplitude $A_1$ of the AC voltage ($A_1$ sin($\omega t+\alpha$)), by a relatively small increase, to be greater than the amplitude $A_1$ calculated in the immediately preceding loop (so as to decrease the control proportional gain Gc(s)).

According to the modification 1-3 described above, the following effects are obtained in addition to the effects similar to the case of the first embodiment described above.

That is, execution of Steps S44 and S45 as described above makes it possible to rapidly control (converge) the resistance value $R_x$ of the heater resistor 141 to the target resistance value $R_x t$ (the heater temperature to the target temperature).

Second Embodiment

Next, a second embodiment will be described.

In the following description, identical reference numerals are given to the components and steps similar to those in the first embodiment described above, and detailed description thereof will be omitted or simplified.

Figure 18:
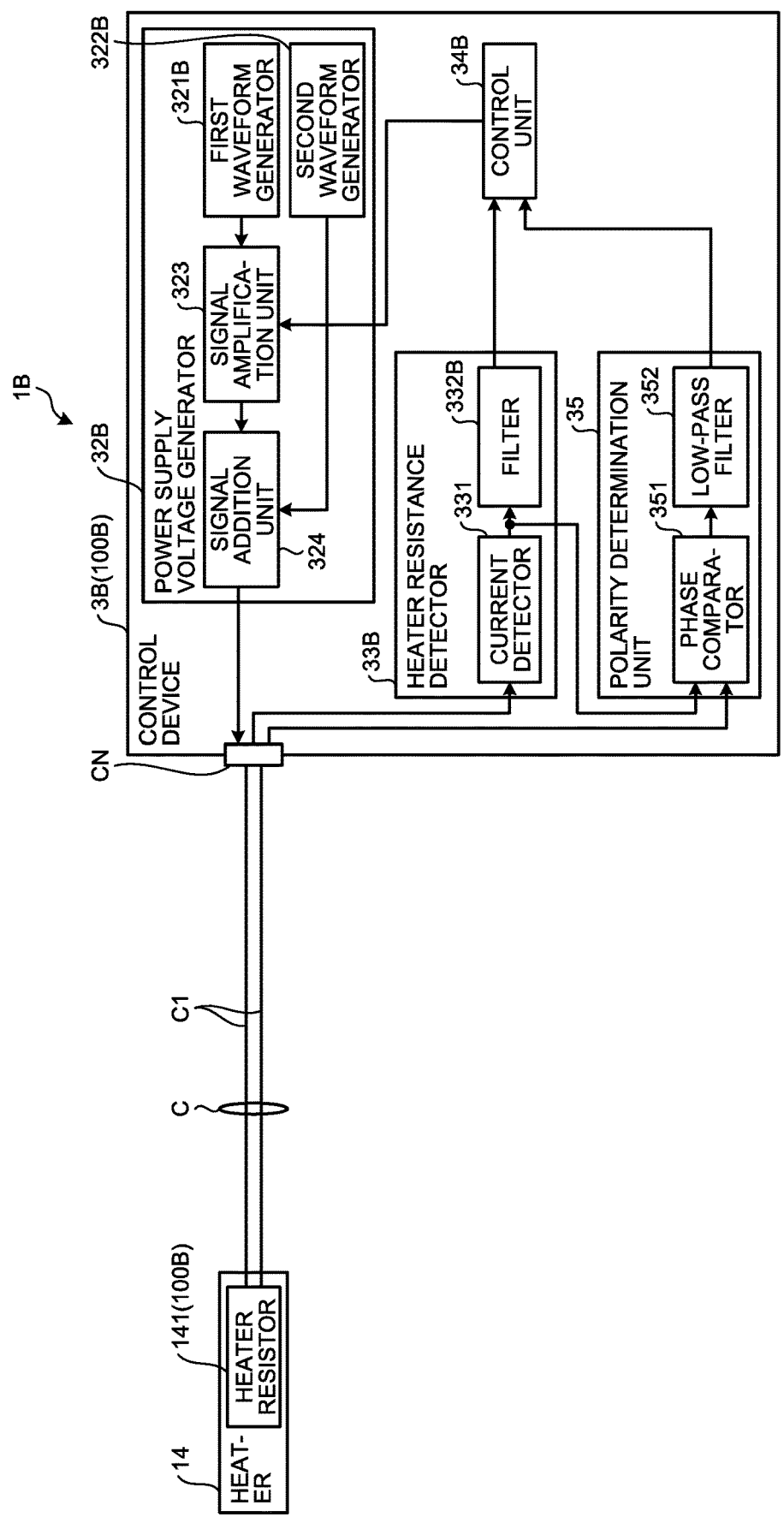
FIG. 18 is a block diagram illustrating a treatment system according to a second embodiment.
Figure 19:
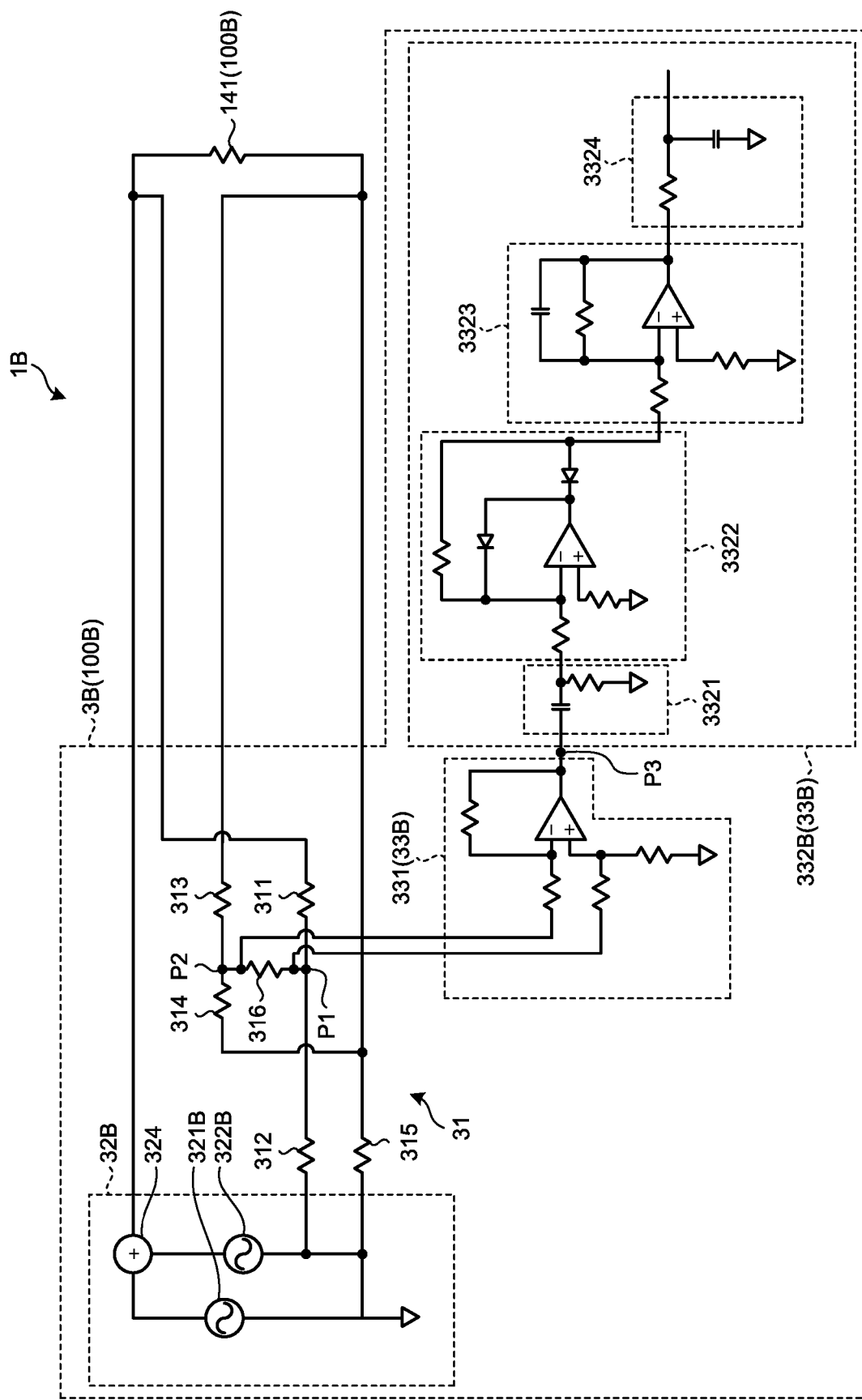
FIG. 19 is a diagram illustrating a circuit configuration of a treatment system.

FIG. 18 is a block diagram illustrating a treatment system 1B according to the second embodiment. FIG. 19 is a diagram illustrating a circuit configuration of the treatment system 1B. Note that FIG. 18 omits illustration of the double bridge circuit 31 similarly to FIG. 3. Also note that FIG. 19 omits illustration of the signal amplification unit 323, a control unit 34B and the polarity determination unit 35 for convenience of explanation.

As illustrated in FIG. 18 or 19, the treatment system 1B (control device 3B) according to the second embodiment employs a power supply voltage generator 32B, a heater resistance detector 33B, and a control unit 34B having functions different from the power supply voltage generator 32, the heater resistance detector 33, and the control unit 34 respectively, and additionally includes a polarity determination unit 35, compared to the treatment system 1 described above in the first embodiment.

As illustrated in FIG. 18 or 19, the power supply voltage generator 32B employs first and second waveform generators 321B and 322B instead of the first and second waveform generators 321 and 322, respectively, compared to the power supply voltage generator 32 described above in the first embodiment.

The first waveform generator 321B generates an AC voltage ($A_3 \sin(\omega_3 t)$) having a first frequency $\omega_3$ corresponding to the driving voltage according to the disclosure.

The second waveform generator 322B generates an AC voltage ($A_4 \sin(\omega_4 t)$) having a second frequency $\omega_4$ corresponding to the detection voltage according to the disclosure. Here, the second frequency $\omega_4$ is a frequency that is about three to four times higher than the first frequency $\omega_3$, for example. An amplitude $A_4$ of the AC voltage ($A_4 \sin(\omega_4 t)$) is a constant value.

Note that under the control of the control unit 34B, the signal amplification unit 323 changes an amplitude $A_3$ (performs amplitude modulation) of the AC voltage ($A_3 \sin(\omega_3 t)$) generated by the first waveform generator 321B. The signal addition unit 324 superimposes the AC voltage ($A_3 \sin(\omega_3 t)$) generated by the first waveform generator 321B and that has undergone amplitude modulation at the signal amplification unit 323 with the AC voltage ($A_4 \sin(\omega_4 t)$) generated by the second waveform generator 322, and thereby generates a power supply voltage $V_3$ (=$A_3 \sin(\omega_3 t) + A_4 \sin(\omega_4 t)$).

That is, in the second embodiment, the power supply voltage $V_3$ is formed by an AC voltage on which a harmonic component is superimposed.

As illustrated in FIG. 18 or 19, the heater resistance detector 33B employs a filter 332B instead of the filter 332 in the heater resistance detector 33 described above in the first embodiment.

Note that a detection value $V_4$ of the current detector 331 is $A_5 \cos(\omega_3 t) + A_6 \sin(\omega_4 t)$ because the power supply voltage is the power supply voltage $V_3$, rather than the power supply voltage $V_1$.

As illustrated in FIG. 19, the filter 332 includes a high-pass filter 3321, a half-wave rectifier circuit 3322, an integration circuit 3323, and a low-pass filter 3324.

As illustrated in FIG. 19, the high-pass filter 3321 includes: a resistor connected in parallel to the input signal; and a capacitor connected in series to the input signal. Subsequently, the high-pass filter 3321 removes a low-frequency component ($A_5 \cos(\omega_3 t)$) and extracts a high-frequency component ($A_6 \sin(\omega_4 t)$) from the detection value $V_4$ of the current detector 331.

As illustrated in FIG. 19, the half-wave rectifier circuit 3322 includes a diode and an operational amplifier, for example. Subsequently, the half-wave rectifier circuit 3322 applies half-wave rectification on the high-frequency component ($A_6 \sin(\omega_4 t)$) extracted by the high-pass filter 3321, and then outputs the result.

As illustrated in FIG. 19, the integration circuit 3323 includes a capacitor, an operational amplifier, for example. Subsequently, the integration circuit 3323 integrates the output signal from the half-wave rectifier circuit 3322 and then outputs the result.

As illustrated in FIG. 19, the low-pass filter 3324 includes: a capacitor connected in parallel to the input signal; and a resistor connected in series to the input signal. Subsequently, an output signal from the integration circuit 3323 is input to the low-pass filter 3324.

Subsequently, in the second embodiment, the heater resistance detector 33B (low-pass filter 3324) outputs a detection value $V_4'$ represented by the following Formula (2) to the control unit 34.

$$V_4' = \frac{A_6}{\sqrt{2}} \quad (2)$$

Figure 20:
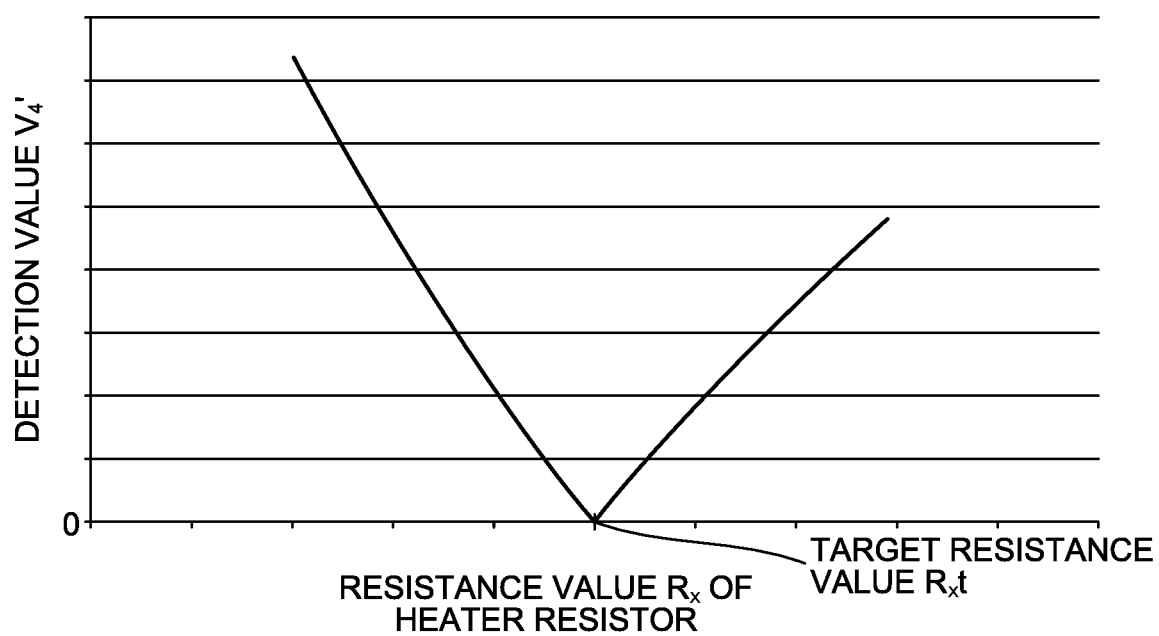
FIG. 20 is a diagram illustrating a relationship between a resistance value of a heater resistor and a detection value.

FIG. 20 is a diagram illustrating a relationship between the resistance value $R_x$ of the heater resistor 141 and the detection value $V_4'$.

Here, there is a relationship illustrated in FIG. 20 between the resistance value $R_x$ (heater temperature) of the heater resistor 141 and the detection value $V_4'$.

Specifically, in the second embodiment, the detection value $V_4'$ is calculated using the half-wave rectifier circuit 3322. Therefore, as illustrated in FIG. 20, the relationship between the resistance value $R_x$ (heater temperature) of the heater resistor 141 and the detection value $V_4'$ is a relationship similar to that of FIG. 11 described above in modification 1-1.

FIG. 21 is a diagram illustrating functions of the polarity determination unit 35. Specifically, (a) and (b) of FIG. 21 illustrate voltage waveforms W1 to W3 and a signal (voltage $V_O$) waveform output from the polarity determination unit 35 at intermediate points P1, P2 and P3 (FIG. 19) in a case where the resistance value $R_x$ of the heater resistor 141 is smaller than the target resistance value $R_x t$ ($R_x < R_x t$). (c) and (d) of FIG. 21 illustrate voltage waveforms W1 to W3 and a signal (voltage $V_O$) waveform output from the polarity determination unit 35 at the intermediate points P1, P2 and P3 in a case where the resistance value $R_x$ of the heater resistor 141 is greater than the target resistance value $R_x t$ ($R_x > R_x t$).

The polarity determination unit 35 is used to determine the magnitude relationship ($R_x < R_x t$ or $R_x > R_x t$) between the resistance value $R_x$ of the heater resistor 141 and the target resistance value $R_x t$. The polarity determination unit 35 includes a phase comparator 351 and a low-pass filter 352, as illustrated in FIG. 18.

The phase comparator 351 outputs a signal (voltage) corresponding to a phase difference between the voltage waveforms W1 and W2 at the intermediate point P1 or P2 and the voltage waveform W3 at the point P3.

The low-pass filter 352 has a configuration similar to the low-pass filter 3324, and receives an output signal from the phase comparator 351, as an input.

Subsequently, the polarity determination unit 35 (low-pass filter 352) outputs a signal (voltage $V_O$) to the control unit 34B.

Here, in a case where the resistance value $R_x$ of the heater resistor 141 is smaller than the target resistance value $R_x t$ ($R_x < R_x t$), the voltage waveforms W1 and W2 at the intermediate point P1 or the intermediate point P2 respectively have a phase difference of 180° from the voltage waveform W3 at the point P3, as illustrated in (a) of FIG. 21. Therefore, as illustrated in (b) of FIG. 21, the polarity determination unit 35 outputs a signal in which the voltage $V_0$ is positive.

In contrast, in a case where the resistance value $R_x$ of the heater resistor 141 is greater than the target resistance value $R_xt$ ($R_x$>$R_xt$), the voltage waveforms W1 and W2 at the intermediate point P1 or the intermediate point P2 respectively have a phase difference of 0° from the voltage waveform W3 at the point P3, as illustrated in (c) of FIG. 21. Therefore, as illustrated in (d) of FIG. 21, the polarity determination unit 35 outputs a signal in which the voltage $V_0$ is 0.

Figure 22:
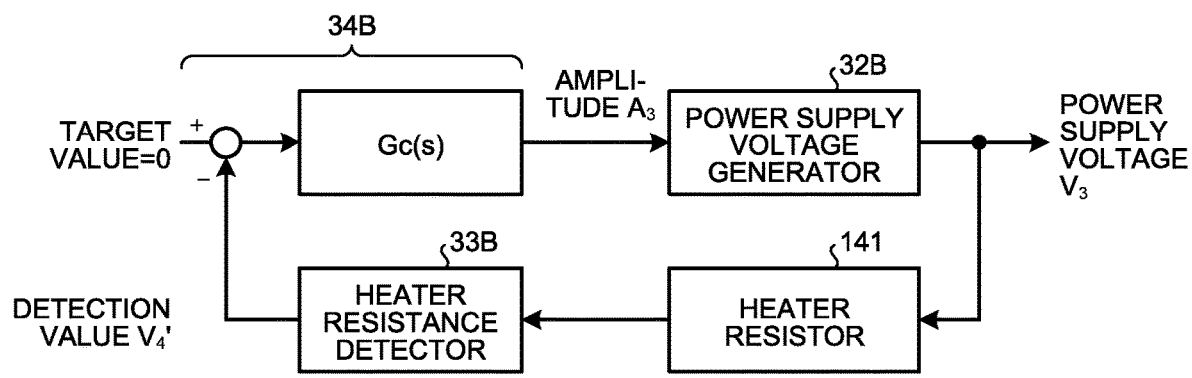
FIG. 22 is a block diagram illustrating feedback control performed by a control unit.

FIG. 22 is a block diagram illustrating feedback control performed by the control unit 34B.

The control unit 34B determines a magnitude relationship ($R_x$<$R_xt$ or $R_x$>$R_xt$) between the resistance value $R_x$ of the heater resistor 141 and the target resistance value $R_xt$ on the basis of the signal (voltage $V_0$) output from the polarity determination unit 35. The control unit 34B also calculates a deviation between the detection value $V_4'$ output from the heater resistance detector 33B and the target value "0". Subsequently, the control unit 34B calculates the amplitude $A_3$ of the AC voltage ($A_3 \sin(\omega_3 t)$) on the basis of the determined magnitude relationship and the calculated deviation, and then outputs the calculated amplitude $A_3$ to the power supply voltage generator 32B (the signal amplification unit 323) as a control target. In response to this, the power supply voltage generator 32B applies the power supply voltage $V_3$ having the amplitude $A_3$ calculated by the control unit 34B to the heater resistor 141 and the double bridge circuit 31. That is, in the second embodiment, the control unit 34B performs amplitude modulation on the power supply voltage $V_3$ (AC voltage ($A_3 \sin(\omega_3 t)$)) via the signal amplification unit 323 similarly to the control unit 34 described above in the first embodiment.

The heater resistor 141 and the control device 3B described above correspond to a heating device 100B (FIGS. 18 and 19) according to the disclosure.

Next, operation (heating control method) of the above-described treatment system 1B will be described.

Figure 23:
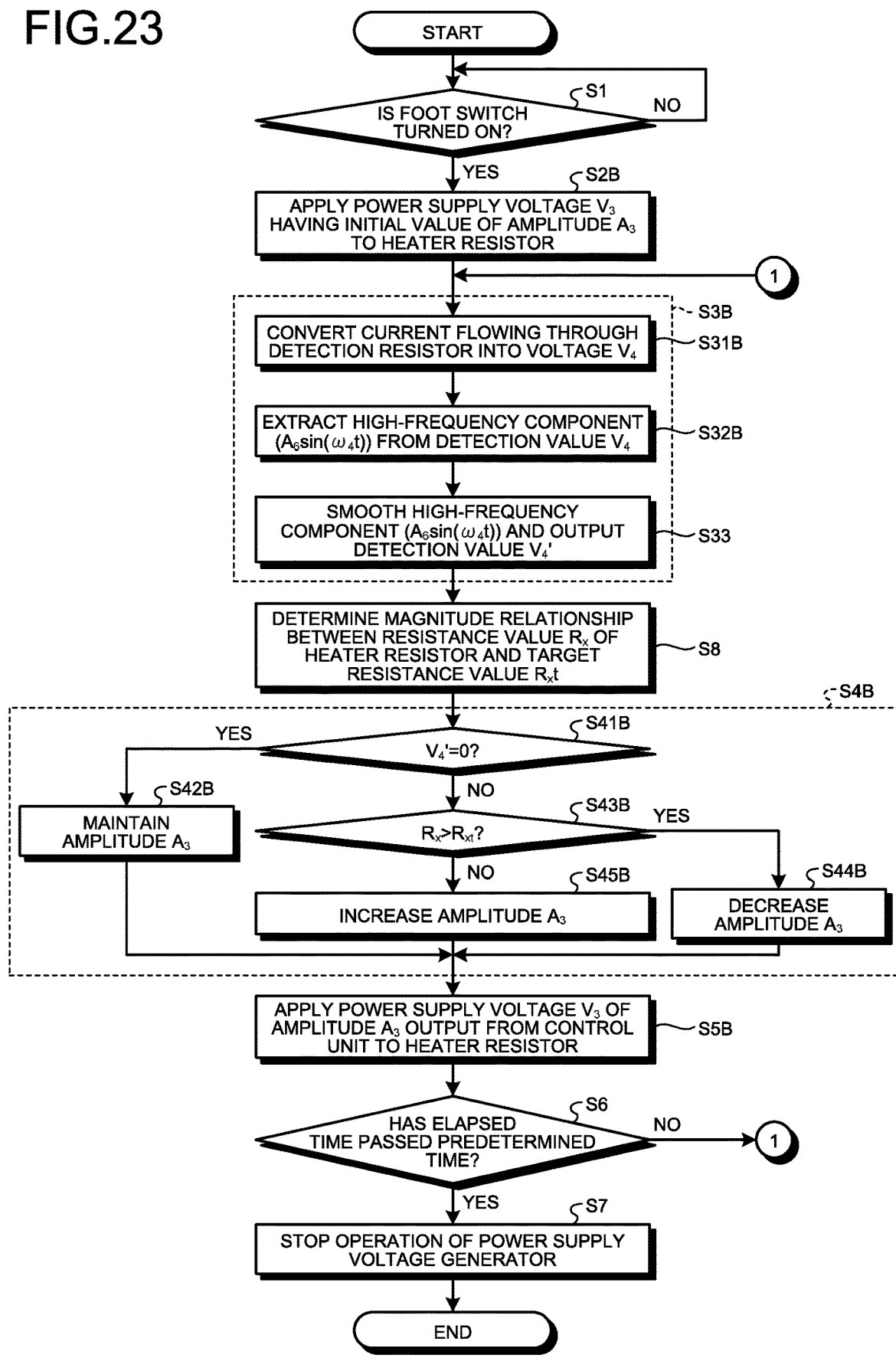
FIG. 23 is a flowchart illustrating a heating control method.

FIG. 23 is a flowchart illustrating a heating control method.

As illustrated in FIG. 23, the heating control method according to the second embodiment employs Steps S2B, S3B, S4B and S5B instead of Steps S2 to S5 and includes an additional Step S8, compared to the heating control method described above in the first embodiment. Therefore, hereinafter, Steps S2B, S3B, S4B, S5B, and S8 will simply be described.

In Step S2B, control unit 34B outputs an initial value of amplitude $A_3$ of AC voltage ($A_3 \sin(\omega_3 t)$) to the power supply voltage generator 32B (signal amplification unit 323). Subsequently, the power supply voltage generator 32B applies the power supply voltage $V_3$ having the initial value of the amplitude $A_3$ to the heater resistor 141 and the double bridge circuit 31.

After Step S2B, the heater resistance detector 33B calculates a detection value $V_4'$ and outputs the calculated value to the control unit 34B (Step S3B).

Specifically, the current detector 331 converts the current flowing through the detection resistor 316 into a voltage $V_4$ (=$A_5 \cos(\omega_3 t)+A_6 \sin(\omega_4 t)$) (Step S31B).

After Step S31B, the filter 332B uses the high-pass filter 3321 and thereby removes a low-frequency component ($A_5 \cos(\omega_3 t)$) and extracts a high-frequency component ($A_6 \sin(\omega_4 t)$) from the detection value $V_4$ of the current detector 331 (Step S32B).

After Step S32B, the filter 332B uses the half-wave rectifier circuit 3322, the integration circuit 3323, and the low-pass filter 3324 to smooth the high-frequency component ($A_6 \sin(\omega_4 t)$) extracted in Step S32B, and then outputs a detection value $V_4'$ (Step S33).

After Step S3B, the control unit 34B determines a magnitude relationship ($R_x$<$R_xt$ or $R_x$>$R_xt$) between the resistance value $R_x$ of the heater resistor 141 and the target resistance value $R_xt$ (Step S8).

That is, the phase comparator 351 outputs a signal (voltage) corresponding to the phase difference between the voltage waveforms W1 and W2 at the intermediate point P1 or P2 and the voltage waveform W3 at the point P3. The low-pass filter 352 receives the output signal from the phase comparator 351 as an input, and then outputs a signal in which the voltage $V_0$ is positive or 0. Subsequently, in a case where, in Step S8, the polarity determination unit 35 has output a signal in which the voltage $V_0$ is positive, the control unit 34B determines that the resistance value $R_x$ of the heater resistor 141 is smaller than the target resistance value $R_xt$ ($Rx$<$R_xt$). In contrast, in a case where the polarity determination unit 35 has output a signal in which the voltage $V_0$ is 0, the control unit 34B determines that the resistance value $R_x$ of the heater resistor 141 is greater than the target resistance value $R_xt$ ($R_x$>$R_xt$).

Although FIG. 23 illustrates the procedure in which Step S8 is executed after Step S3B for convenience of explanation, Step S3B and Step S8 are to be executed in parallel in practice.

After Step S8, the control unit 34B calculates the amplitude $A_3$ of the AC voltage ($A_3 \sin(\omega_3 t)$) on the basis of the magnitude relationship determined in Step S8 and the deviation between the detection value $V_4'$ output from the heater resistance detector 33B and the target value "0" (Step S4B).

Specifically, first, the control unit 34B judges whether the detection value $V_4'$ output from the heater resistance detector 33B matches the target value "0" (whether the detection value $V_4'$ is "0") (Step S41B).

In a case where the detection value $V_4'$ is judged to be "0" (Step S41B: Yes), the control unit 34B judges that the resistance value $R_x$ of the heater resistor 141 has reached the target resistance value $R_xt$ (the heater temperature has reached the target temperature). Subsequently, the control unit 34B maintains (Step S42B) the amplitude $A_3$ calculated in the immediately preceding loop (loop including Steps S3B, S8, S4B, S5B, and S6), and then outputs the maintained amplitude $A_3$ to the power supply voltage generator 32B (the signal amplification unit 323).

In contrast, in a case where it is judged that the detection value $V_4'$ is not "0" (Step S41B: No), the control unit 34B judges whether the magnitude relationship determined in Step S8 is $R_x$>$R_xt$ (Step S43B).

When it is judged that $R_x$>$R_xt$, (Step S43B: Yes), the control unit 34B judges that the heater temperature is higher than the target temperature. Subsequently, in order to reduce the heater temperature, the control unit 34B changes the amplitude $A_3$ of the AC voltage ($A_3 \sin(\omega_3 t)$) so as to be smaller than the amplitude $A_3$ calculated in the immediately preceding loop in accordance with the deviation between the detection value $V_4'$ and the target value "0" (Step S44B), and then outputs the reduced amplitude $A_3$ to the power supply voltage generator 32B (signal amplification unit 323).

In contrast, in a case where it is judged that $R_x$<$R_xt$ (Step S43B: No), the control unit 34B judges that the heater temperature is lower than the target temperature. Subsequently, in order to increase the heater temperature, the control unit 34B changes the amplitude $A_3$ of the AC voltage ($A_3 \sin(\omega_3 t)$) so as to be greater than the amplitude $A_3$ calculated in the immediately preceding loop in accordance with the deviation between the detection value $V_4'$ and the target value "0" (Step S45B), and outputs the increased amplitude $A_3$ to the power supply voltage generator 32B (signal amplification unit 323).

After Step S42B, Step S44B, or Step S45B, the power supply voltage generator 32B applies, in Step S5B, the power supply voltage $V_3$ having the amplitude $A_3$ output from the control unit 34B in Step S42B, Step S44B, or Step S45B to the heater resistor 141 and the double bridge circuit 31. Thereafter, the treatment system 1B proceeds to Step S6.

The following is a description of an example of transition of the power supply voltage $V_3$, the detection value $V_4$ of the current detector 331, the high-frequency component ($A_6 \sin(\omega_4 t)$) after passing through the high-pass filter 3321, and the detection value $V_4'$ of the heater resistance detector 33B according to the above-described heating control method.

Figure 24:
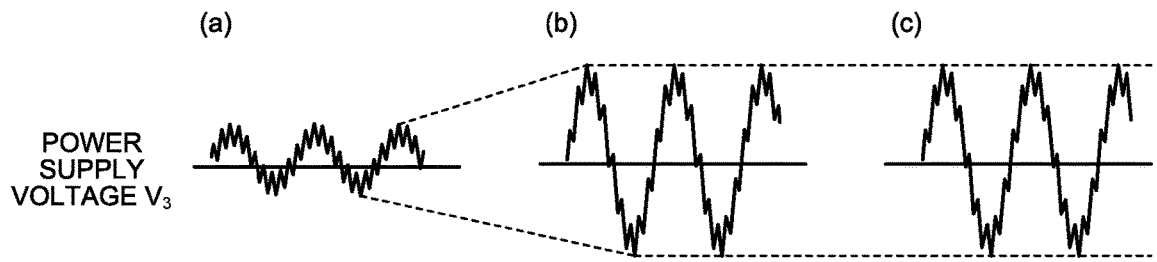
FIG. 24 is a diagram illustrating a transition of a power supply voltage.
Figure 25:
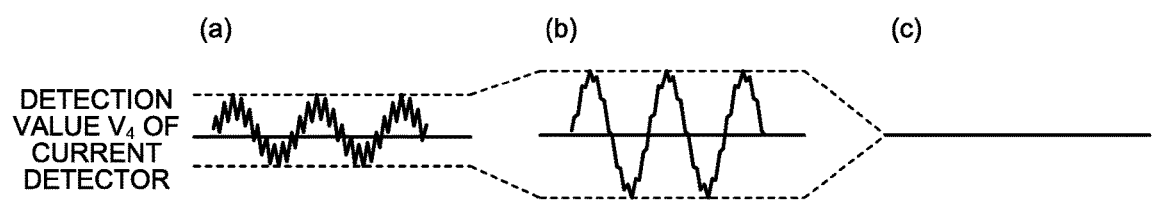
FIG. 25 is a diagram illustrating a transition of an output value of a current detector.
Figure 26:
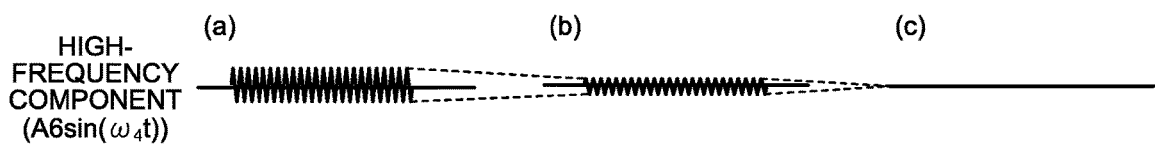
FIG. 26 is a diagram illustrating a transition of a high-frequency component after passing through a high-pass filter.
Figure 27:
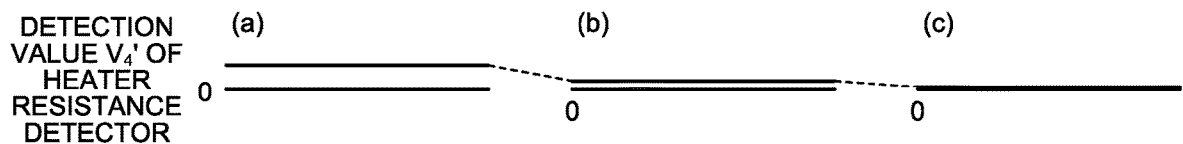
FIG. 27 is a diagram illustrating a transition of a detection value of a heater resistance detector.

FIG. 24 is a diagram illustrating a transition of the power supply voltage $V_3$. FIG. 25 is a diagram illustrating a transition of the detection value $V_4$ of the current detector 331. FIG. 26 is a diagram illustrating a transition of the high-frequency component ($A_6 \sin(\omega_4 t)$) after passing through the high-pass filter 3321. FIG. 27 is a diagram illustrating a transition of the detection value $V_4'$ of the heater resistance detector 33B. Note that (a) of FIG. 24, (a) of FIG. 25, (a) of FIG. 26, and (a) of FIG. 27 illustrate a case where the resistance value $R_x$ of the heater resistor 141 is sufficiently smaller than the target resistance value $R_x t$ (a case where the heater temperature is sufficiently lower than the target temperature). (b) of FIG. 24, (b) of FIG. 25, (b) of FIG. 26, and (b) of FIG. 27 illustrate a case where the resistance value $R_x$ of the heater resistor 141 approaches the target resistance value $R_x t$ (a case where the heater temperature approaches the target temperature) as a result of heating control, compared with the states illustrated in (a) of FIG. 24, (a) of FIG. 25, (a) of FIG. 26, and (a) of FIG. 27. (c) of FIG. 24, (c) of FIG. 25, (c) of FIG. 26, and (c) of FIG. 27 illustrate a case where the resistance value $R_x$ of the heater resistor 141 matches the target resistance value $R_x t$ (a case where the heater temperature matches the target temperature) as a result of heating control.

As observed in comparison between (a) and (b) of FIG. 24, in a case where the resistance value $R_x$ of the heater resistor 141 is smaller than the target resistance value $R_x t$ (the heater temperature is lower than the target temperature), the power supply voltage $V_3$ is set such that the amplitude $A_3$ will be increased by the processes in Steps S45B and S5B in order to increase the resistance value $R_x$ of the heater resistor 141 (increase the heater temperature). In a case where the resistance value $R_x$ of the heater resistor 141 matches the target resistance value $R_x t$ (in a case where the heater temperature matches the target temperature) as illustrated in (c) of FIG. 24, the power supply voltage $V_3$ is set to be maintained to have the amplitude $A_3$ ((b) of FIG. 24) of the power supply voltage $V_3$ in the immediately preceding loop by the processes in Steps S42B and S5B.

In the detection value $V_4$ of the current detector 331 and the high-frequency component ($A_6 \sin(\omega_4 t)$) after passing through the high-pass filter 3321, an amplitude $A_6$ (detection value $V_4'$) approaches "0" as the resistance value $R_x$ of the heater resistor 141 approaches the target resistance value $R_x t$ (as the heater temperature approaches the target temperature) by the processes of Steps S45B and S5B, as illustrated in (a) and (b) of FIG. 25 and (a) and (b) of FIG. 26 ((a) and (b) of FIG. 27). Furthermore, as illustrated in (c) of FIG. 25 and (c) of FIG. 26 ((c) of FIG. 27), the amplitude $A_6$ (detection value $V_4'$) indicates "0" in a case where the resistance value $R_x$ of the heater resistor 141 matches the target resistance value $R_x t$ (in a case where the heater temperature matches the target temperature).

Here, as observed in comparison of (a) and (b) of FIG. 24 with (a) and (b) of FIG. 25, a low-frequency component ($A_5 \cos(\omega_3 t)$) of the detection value $V_4$ of the current detector 331 changes in accordance with the amplitude modulation of the power supply voltage $V_3$. Therefore, the low-frequency component ($A_5 \cos(\omega_3 t)$) corresponds to the first current component according to the disclosure. In contrast, as observed in comparison of (a) to (c) of FIG. 24 with (a) to (c) of FIG. 25 ((a) to (c) of FIG. 26) or (a) to (c) of FIG. 27, the high-frequency component ($A_6 \sin(\omega_4 t)$) of the detection value $V_4$ of the current detector 331 and the detection value $V_4'$ would not change in accordance with the amplitude modulation of the power supply voltage $V_3$, but would change in accordance with the change in the heater temperature (change in the resistance value $R_x$ of the heater resistor 141). Therefore, the high-frequency component ($A_6 \sin(\omega_4 t)$) and the detection value $V_4'$ of the detection value $V_4$ of the current detector 331 correspond to the second current component according to the disclosure.

According to the second embodiment described above, the following effects are obtained in addition to the effects similar to the case of the first embodiment described above.

The heating device 100B according to the second embodiment employs the high-frequency AC voltage ($A_4 \sin(\omega_4 t)$) as the detection voltage according to the disclosure. This makes it possible to significantly reduce the risk of electric shock.

Modification 2-1 of Second Embodiment

Figure 28:
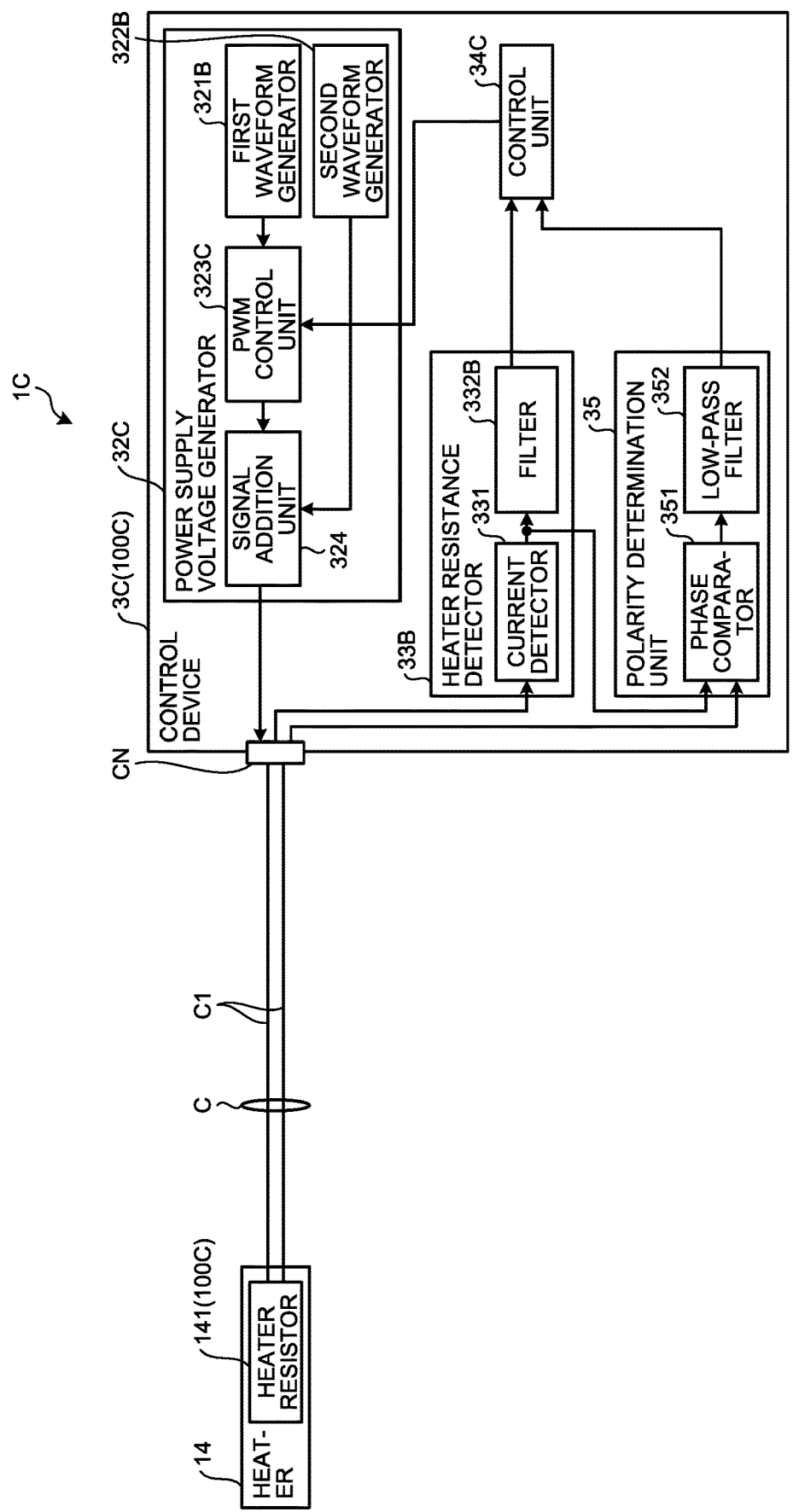
FIG. 28 is a diagram illustrating modification 2-1 of the second embodiment.
Figure 29:
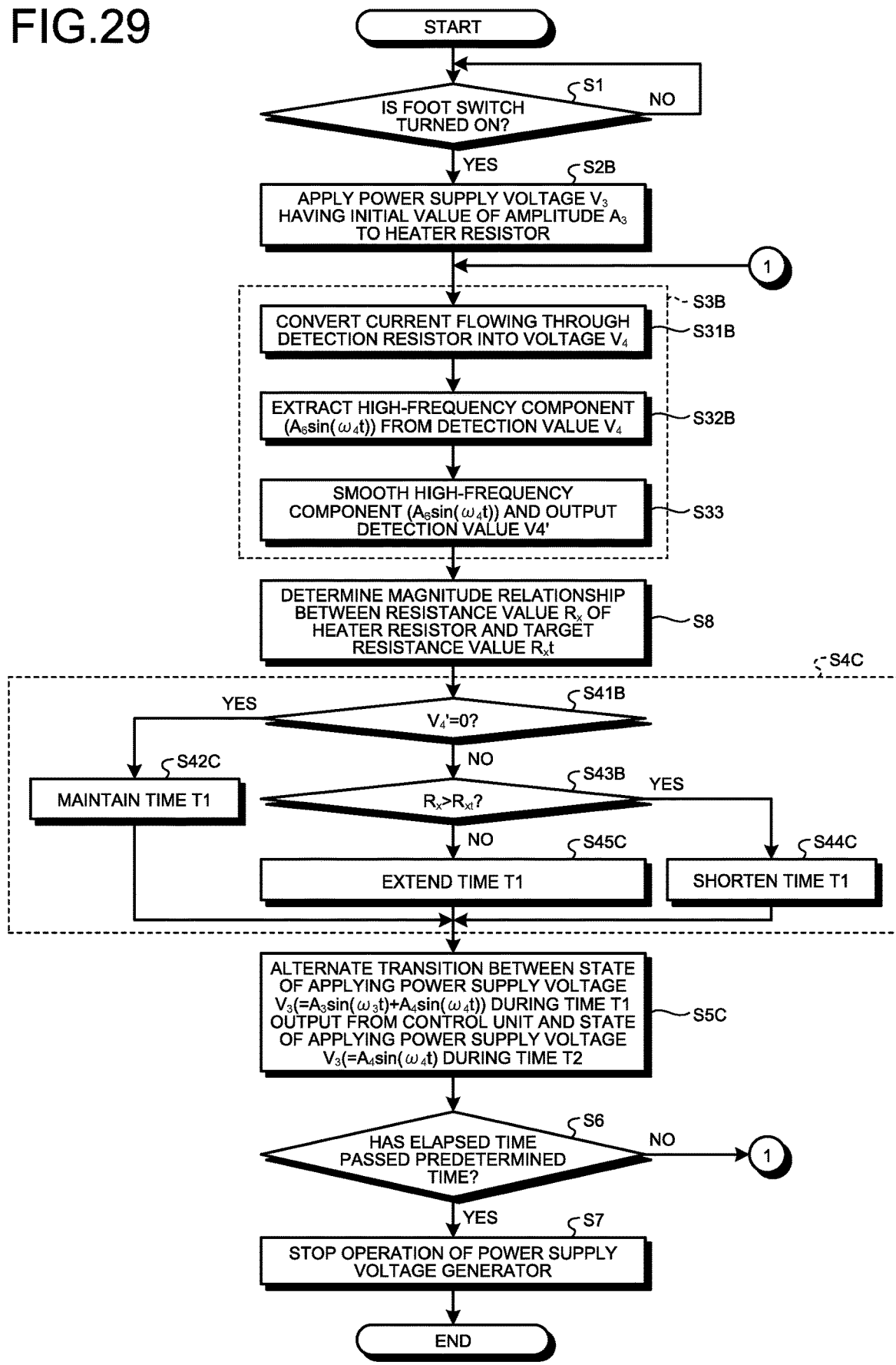
FIG. 29 is a diagram illustrating modification 2-1 of the second embodiment.
Figure 30:
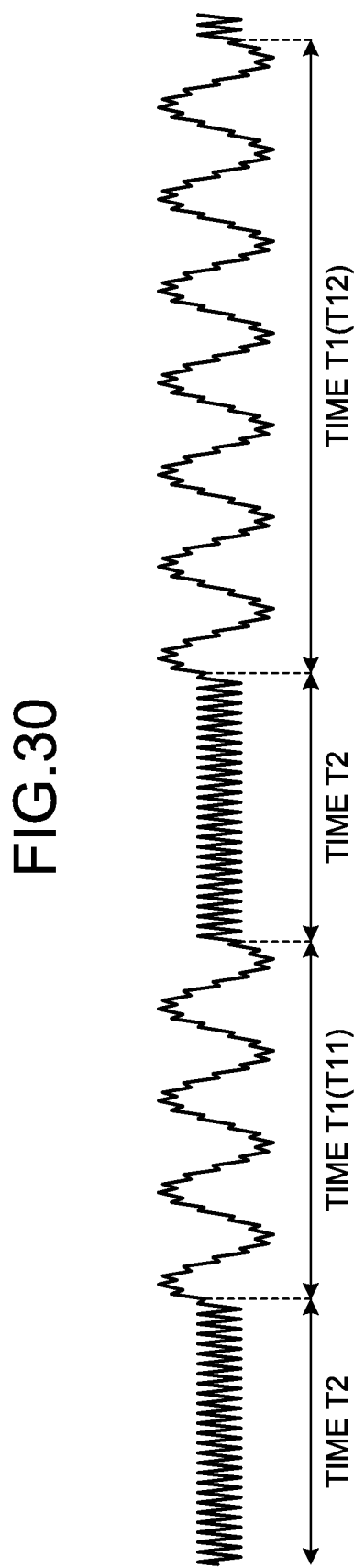
FIG. 30 is a diagram illustrating modification 2-1 of the second embodiment.

FIGS. 28 to 30 are diagrams illustrating modification 2-1 of the second embodiment. Specifically, FIG. 28 is a block diagram illustrating a treatment system 10 according to modification 2-1. FIG. 29 is a flowchart illustrating a heating control method according to modification 2-1. FIG. 30 is a diagram illustrating a waveform of the power supply voltage $V_3$ according to modification 2-1.

In contrast to the treatment system 1B described above in the second embodiment, the treatment system 10 (control device 3C) according to modification 2-1 as illustrated in FIG. 28 employs a power supply voltage generator 32C including a PWM control unit 323C instead of the signal amplification unit 323 as well as employing a control unit 34C having a function different from that of the control unit 34B.

Under the control of the control unit 34C, the PWM control unit 323C changes the time T1 (FIG. 30) for outputting the AC voltage ($A_3 \sin(\omega_3 t)$) generated by the first waveform generator 321B to the signal addition unit 324. In other words, the PWM control unit 323C performs pulse width modulation on the AC voltage ($A_3 \sin(\omega_3 t)$). Furthermore, after the time T1, the PWM control unit 323C does not output the AC voltage ($A_3 \sin(\omega_3 t)$) to the signal addition unit 324 during a fixed period of time T2 (FIG. 30). Subsequently, the PWM control unit 323C alternates transition between a state of outputting the AC voltage ($A_3 \sin(\omega_3 t)$) during the time T1 and a state of not outputting the AC voltage ($A_3 \sin(\omega_3 t)$) during the time T2 to the signal addition unit 324 (FIG. 30).

Note that, for the time T1, the signal addition unit 324 superimposes the AC voltage ($A_3 \sin(\omega_3 t)$) generated by the first waveform generator 321B and that has undergone pulse width modulation at the PWM control unit 323C with the AC voltage ($A_4 \sin(\omega_4 t)$) generated by the second waveform generator 322B, and thereby generates a power supply voltage $V_3$ (=$A_3 \sin(\omega_3 t)+A_4 \sin(\omega_4 t)$). On the other hand, during the time T2, the signal addition unit 324 outputs the AC voltage ($A_4 \sin(\omega_4 t)$) generated by the second waveform generator 322B as the power supply voltage $V_3$ (=$A_4 \sin(\omega_4 t)$).

Similarly to the control unit 34B described above in the second embodiment, the control unit 34C determines the magnitude relationship ($R_x<R_x t$ or $R_x>R_x t$) between the resistance value $R_x$ of the heater resistor 141 and the target resistance value $R_x t$, and together with this, calculates a deviation between the detection value $V_4'$ output from the heater resistance detector 33B and the target value. Subsequently, the control unit 34C changes the above-described time T1 on the basis of the determined magnitude relationship and the calculated deviation. That is, in modification 2-1, the control unit 34C performs pulse width modulation on the power supply voltage $V_3$ (AC voltage ($A_3 \sin(\omega_3 t)$)) via the PWM control unit 323C.

The heater resistor 141 and the control device 3C described above correspond to a heating device 100C (FIG. 28) according to the disclosure.

Next, a heating control method according to modification 2-1 will be described.

As illustrated in FIG. 29, the heating control method according to modification 2-1 employs Steps S4C and S5C instead of Steps S4B and S5B, respectively, compared to the heating control method described above in the second embodiment. Therefore, Steps S4C and S5C alone will be described below.

In Step S4C, the control unit 34C calculates the time T1 on the basis of the magnitude relationship ($R_x<R_x t$ or $R_x>R_x t$) between the resistance value $R_x$ of the heater resistor 141 and the target resistance value $R_x t$, and on the basis of the deviation between the detection value $V_4'$ output from the heater resistance detector 33B and the target value.

Note that Step S4C includes Steps S41B, S42C, S43B, S44C, and S45C similar to Steps S41B, S42B, S43B, S44B, and S45B in Step S4B described above in the second embodiment. Here, Steps S42C, S44C, and S45C are different from Steps S42B, S44B, and S45B respectively only in that the change target has been changed from the amplitude $A_3$ to the time T1 along with the change from amplitude modulation to pulse width modulation.

For example, in Step S44C, the control unit 34C sets the time T1 shorter than the time T1 calculated at the immediately preceding loop (loop including Steps S3B, S8, S4C, S5C, and S6) in accordance with the deviation between the resistance value $R_x$ and the target resistance value $R_x t$ in order to reduce the heater temperature, and then outputs the shortened time T1 (for example, time T11 (FIG. 30)) to the power supply voltage generator 32C (PWM control unit 323C).

Furthermore, for example, in Step S45C, the control unit 34C extends the time T1 to be longer than the time T1 calculated in the immediately preceding loop in accordance with the deviation between the resistance value $R_x$ and the target resistance value $R_x t$ in order to increase the heater temperature, and then outputs the extended time T1 (for example, time T12 (FIG. 30)) to the power supply voltage generator 32C (PWM control unit 323C).

After Steps S42C, S44C, or S45C, the power supply voltage generator 32C performs, in Step S5C, for the heater resistor 141 and the double bridge circuit 31, alternate transition between a state of applying the power supply voltage $V_3$ (=$A_3 \sin(\omega_3 t)+A_4 \sin(\omega_4 t)$) obtained by superimposing the AC voltage ($A_3 \sin(\omega_3 t)$) with the AC voltage ($A_4 \sin(\omega_4 t)$) during the time T1 output from the control unit 34C in Steps S42C, S44C, or S45C, and a state of applying the power supply voltage $V_3$ (=$A_4 \sin(\omega_4 t)$) which is the AC voltage ($A_4 \sin(\omega_4 t)$) during the time T2 (FIG. 30). Thereafter, the treatment system 10 proceeds to Step S6.

It is also possible to have an effect similar to the above-described second embodiment even in the case of employing the configuration in which pulse width modulation is performed on the power supply voltage $V_3$ (AC voltage ($A_3 \sin(\omega_3 t)$)) as in the above-described modification 2-1.

Third Embodiment

Next, a third embodiment of the disclosure will be described.

In the following description, identical reference numerals are given to the components and steps similar to those in the first embodiment described above, and detailed description thereof will be omitted or simplified.

Figure 31:
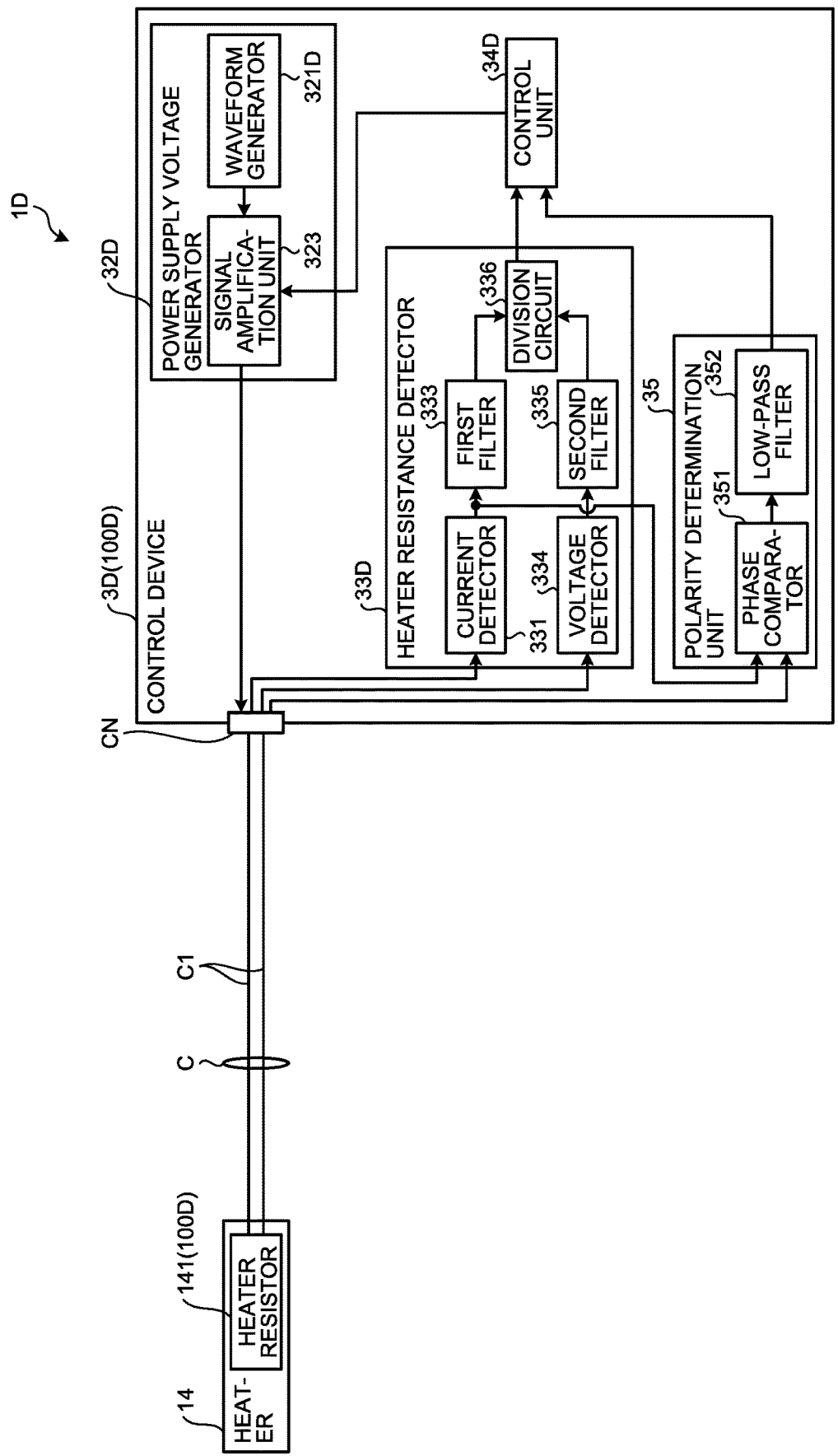
FIG. 31 is a block diagram illustrating a treatment system according to a third embodiment.
Figure 32:
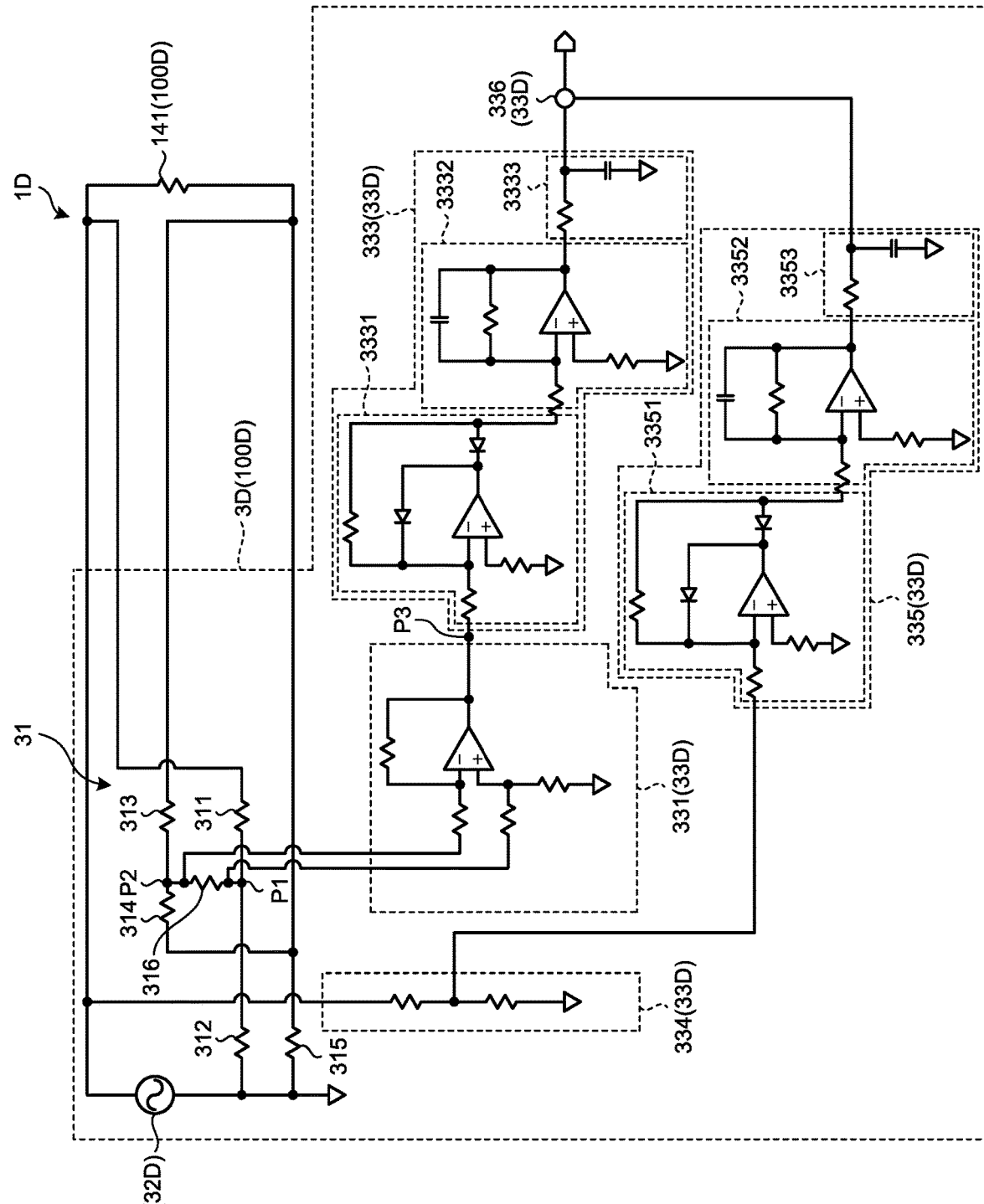
FIG. 32 is a diagram illustrating a circuit configuration of a treatment system.

FIG. 31 is a block diagram illustrating a treatment system 1D according to the third embodiment. FIG. 32 is a diagram illustrating a circuit configuration of the treatment system 1D. Note that FIG. 31 omits illustration of the double bridge circuit 31 similarly to FIG. 3. Also note that FIG. 32 omits illustration of the signal amplification unit 323, a control unit 34D and the polarity determination unit 35 for convenience of explanation.

As illustrated in FIG. 31 or 32, the treatment system 1D (control device 3D) according to the third embodiment employs a power supply voltage generator 32D, a heater resistance detector 33D, and the control unit 34D having functions different from the power supply voltage generator 32, the heater resistance detector 33, and the control unit 34 respectively, and additionally includes the polarity determination unit 35 described above in the second embodiment, compared to the treatment system 1 described above in the first embodiment.

As illustrated in FIG. 31 or 32, the power supply voltage generator 32D omits the signal addition unit 324 and employs a single waveform generator 321D instead of the first and second waveform generators 321 and 322, compared to the power supply voltage generator 32 described above in the first embodiment.

The waveform generator 321D generates a power supply voltage $V_5$ (=$A_7 \sin \omega t$) that is an AC voltage.

Note that under the control of the control unit 34D, the signal amplification unit 323 changes an amplitude $A_7$ (performs amplitude modulation) of the power supply voltage $V_5$ (=$A_7 \sin \omega t$) generated by the waveform generator 321D.

As illustrated in FIG. 31 or 32, the heater resistance detector 33D includes a first filter 333, a voltage detector 334, a second filter 335, and a division circuit 336, in addition to the current detector 331 described above in the first embodiment.

Note that a detection value $V_6$ of the current detector 331 is $A_8 \cos \omega t$ because the power supply voltage is the power supply voltage $V_5$, rather than the power supply voltage $V_1$.

As illustrated in FIG. 32, the first filter 333 includes a half-wave rectifier circuit 3331, an integration circuit 3332, and a low-pass filter 3333.

As illustrated in FIG. 32, the half-wave rectifier circuit 3331 includes a diode and an operational amplifier, for example. Subsequently, the half-wave rectifier circuit 3331 performs half-wave rectification on the detection value $V_6$ (=$A_8 \cos \omega t$) of the current detector 331 and outputs the result.

As illustrated in FIG. 32, the integration circuit 3332 includes a capacitor, an operational amplifier, for example. Subsequently, the integration circuit 3332 integrates the output signal from the half-wave rectifier circuit 3331 and outputs the result.

As illustrated in FIG. 32, the low-pass filter 3333 includes: a capacitor connected in parallel to the input signal; and a resistor connected in series to the input signal. Subsequently, an output signal from the integration circuit 3332 is input to the low-pass filter 3333.

Subsequently, the first filter 333 (low-pass filter 3333) outputs a detection value $V_6'$ illustrated in the following Formula (3) to the division circuit 336.

$$V_6' = \frac{A_8}{\sqrt{2}} \quad (3)$$

As illustrated in FIG. 32, the voltage detector 334 is formed of a resistor or the like, and divides the power supply voltage $V_5$ (=$A_7 \sin \omega t$) to output a detection value $V_7$ (=$A_9 \sin \omega t$).

As illustrated in FIG. 32, the second filter 335 includes a half-wave rectifier circuit 3351, an integration circuit 3352, and a low-pass filter 3353.

As illustrated in FIG. 32, the half-wave rectifier circuit 3351 includes a diode and an operational amplifier, for example. Subsequently, the half-wave rectifier circuit 3351 applies half-wave rectification on the detection value $V_7$ (=$A_9 \sin \omega t$) of the voltage detector 334 and outputs the result.

As illustrated in FIG. 32, the integration circuit 3352 includes a capacitor, an operational amplifier, for example. Subsequently, the integration circuit 3352 integrates the output signal from the half-wave rectifier circuit 3351 and outputs the result.

As illustrated in FIG. 32, the low-pass filter 3353 includes a capacitor connected in parallel to the input signal and a resistor connected in series to the input signal. Subsequently, an output signal from the integration circuit 3352 is input to the low-pass filter 3353.

Subsequently, the second filter 335 (low-pass filter 3353) outputs a detection value $V_7'$ represented by the following Formula (4) to the division circuit 336.

$$V_7' = \frac{A_9}{\sqrt{2}} \quad (4)$$

The division circuit 336 receives detection values $V_6'$ and $V_7'$ of the first and second filters 333 and 335 respectively as an input, divides the detection value $V_6'$ by the detection value $V_7'$, and then outputs a detection value $V_8$ (=$V_6'/V_7'$) obtained as a result of division to the control unit 34D.

Here, the detection value $V_6$ of the current detector 331 is proportional to the power supply voltage $V_5$. Furthermore, the detection value $V_6$ includes both a component that changes in accordance with the amplitude modulation of the power supply voltage $V_5$ and a component that changes in accordance with a change in the heater temperature (a change in the resistance value $R_x$ of the heater resistor 141). Therefore, the division circuit 336 divides the detection value $V_6'$ (the value obtained by smoothing the detection value $V_6$ by the first filter 333) by the detection value $V_7'$ (the value obtained by performing smoothing using the second filter 335 on the detection value $V_7$ obtained by dividing the power supply voltage $V_5$) so as to remove a component that changes in accordance with the amplitude modulation of the power supply voltage $V_5$ from the detection value $V_6'$. That is, the detection value $V_8$ obtained as a result of division would not change in accordance with the amplitude modulation of the power supply voltage $V_5$ but would change in accordance with the change in the heater temperature (change in the resistance value $R_x$ of the heater resistor 141). Therefore, the detection value $V_8$ corresponds to the second current component according to the disclosure.

Figure 33:
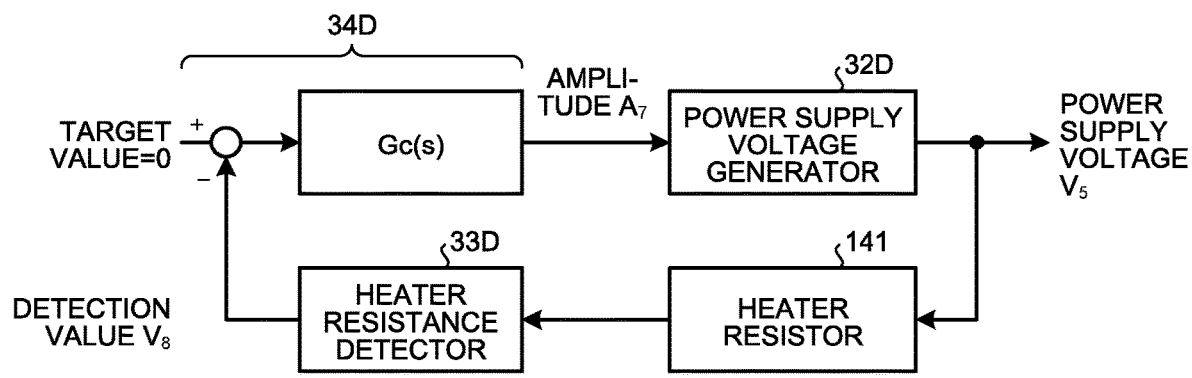
FIG. 33 is a block diagram illustrating feedback control performed by a control unit.

FIG. 33 is a block diagram illustrating feedback control performed by the control unit 34D.

Similarly to the control unit 34B described above in the second embodiment, the control unit 34D determines a magnitude relationship ($R_x < R_x t$ or $R_x > R_x t$) between the resistance value $R_x$ of the heater resistor 141 and the target resistance value $R_x t$ on the basis of the signal (voltage $V_0$) output from the polarity determination unit 35. The control unit 34D also calculates a deviation between the detection value $V_8$ output from the heater resistance detector 33D (division circuit 336) and the target value "0". Subsequently, the control unit 34D calculates the amplitude $A_7$ of the power supply voltage $V_5$ (=$A_7 \sin \omega t$) on the basis of the determined magnitude relationship and the calculated deviation, and then outputs the calculated amplitude $A_7$ to the power supply voltage generator 32D (the signal amplification unit 323) as a control target. In response to this, the power supply voltage generator 32D applies the power supply voltage $V_5$ having the amplitude $A_7$ calculated by the control unit 34D to the heater resistor 141 and the double bridge circuit 31. That is, in the third embodiment, the control unit 34D performs amplitude modulation on the power supply voltage $V_5$ via the signal amplification unit 323 similarly to the control unit 34 described above in the first embodiment.

The heater resistor 141 and the control device 3D described above correspond to a heating device 100D (FIGS. 31 and 32) according to the disclosure.

Next, operation (heating control method) of the above-described treatment system 1D will be described.

Figure 34:
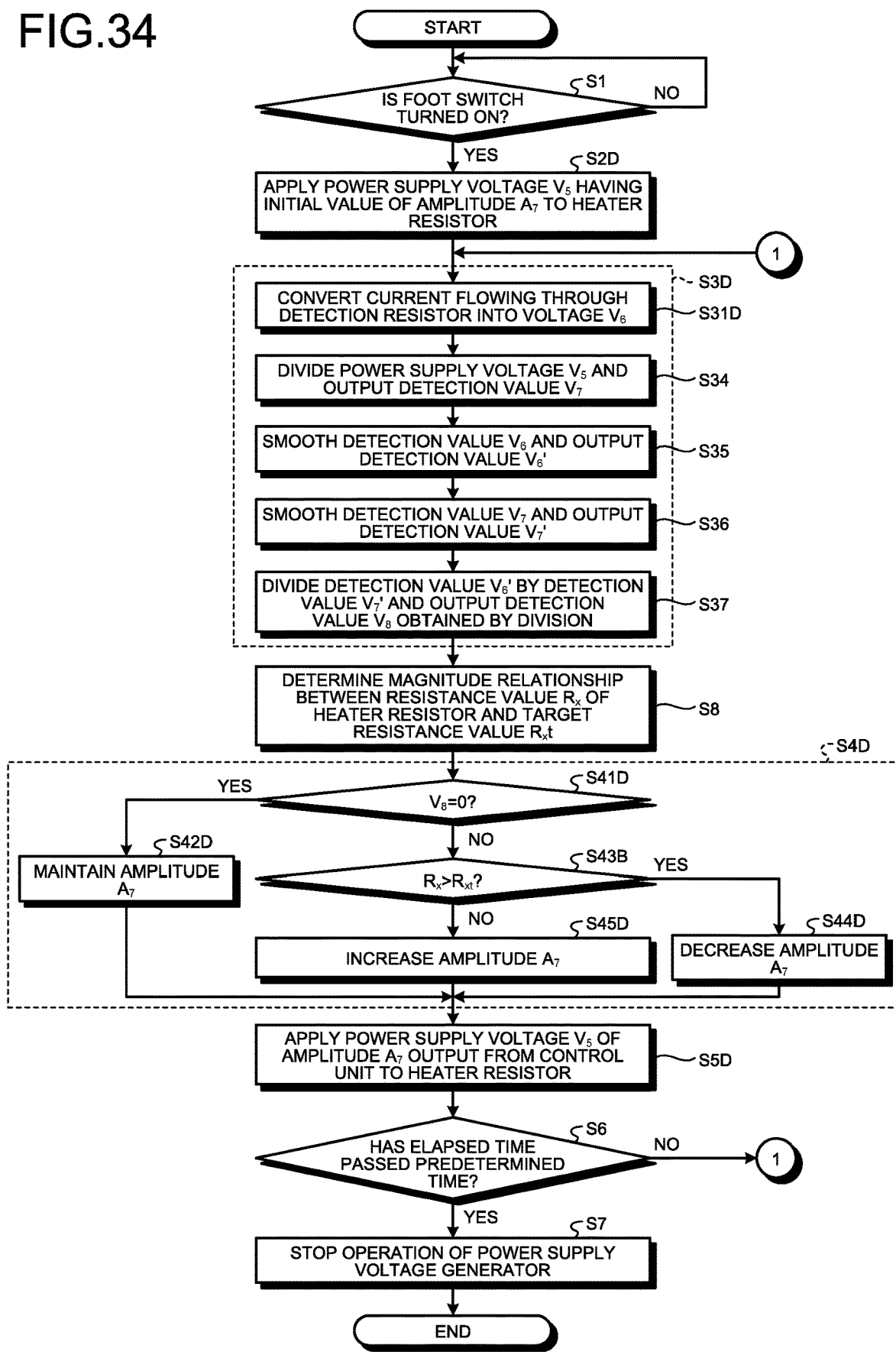
FIG. 34 is a flowchart illustrating a heating control method.

FIG. 34 is a flowchart illustrating a heating control method.

As illustrated in FIG. 34, the heating control method according to the third embodiment employs Steps S2D, S3D, S4D and S5D instead of Steps S2 to S5 and includes an additional Step S8 described above in the second embodiment, compared to the heating control method described above in the first embodiment. Therefore, Steps S2D, S3D, S4D, and S5D alone will be described below.

In Step S2D, the control unit 34D outputs an initial value of the amplitude $A_7$ of the power supply voltage $V_5$ (=$A_7 \sin \omega t$) to the power supply voltage generator 32D (the signal amplification unit 323). Subsequently, the power supply voltage generator 32D applies the power supply voltage $V_5$ having the initial value of the amplitude $A_7$ to the heater resistor 141 and the double bridge circuit 31.

After Step S2D, the heater resistance detector 33D calculates the detection value $V_8$, and outputs the calculated value to the control unit 34D (Step S3D).

Specifically, the current detector 331 converts the current flowing through the detection resistor 316 into a voltage $V_6$ (=$A_8 \cos \omega t$) (Step S31D).

After Step S31D, the voltage detector 334 divides the power supply voltage $V_5$ and outputs the detection value $V_7$ (=$A_9 \sin \omega t$) (Step S34).

After Step S34, the first filter 333 uses the half-wave rectifier circuit 3331, the integration circuit 3332, and the low-pass filter 3333 to smooth the detection value $V_6$ of the current detector 331 in Step S31D, and then outputs a detection value $V_6'$ (Step S35).

After Step S35, the second filter 335 uses the half-wave rectifier circuit 3351, the integration circuit 3352, and the low-pass filter 3353 to smooth the detection value $V_7$ of the voltage detector 334 in Step S34, and then outputs a detection value $V_7'$ (Step S36).

After Step S36, the division circuit 336 divides the detection value $V_6'$ of the first filter 333 in Step S35 by the detection value $V_7'$ of the second filter 335 in Step S36, and then outputs the detection value $V_8$ obtained by the division (Step S37).

Although FIG. 34 illustrates the procedure in which Step S34 is executed after Step S31D for convenience of explanation, Step S31D and Step S34 are to be executed in parallel in practice. Steps S35 and S36 are also executed in parallel. Furthermore, although FIG. 34 illustrates the procedure in which Step S8 is executed after Step S3D for convenience of explanation, Step S3D and Step S8 are to be executed in parallel in practice.

After Step S8, the control unit 34D calculates the amplitude $A_7$ of the power supply voltage $V_5$ (=$A_7 \sin \omega t$) on the basis of the magnitude relationship determined in Step S8 and the deviation between the detection value $V_8$ output from the heater resistance detector 33D and the target value "0" (Step S4D).

Note that Step S4D includes Steps S41D, S42D, S43B, S44D, and S45D similar to Steps S41B, S42B, S43B, S44B, and S45B in Step S4B described above in the second embodiment. Here, Step S41D is different from Step S41B only in that the comparison target with the target value "0" has been changed from the detection value $V_4'$ to the detection value $V_8$. Furthermore, Steps S42D, S44D, and S45D are different from Steps S42B, S44B, and S45B respectively only in that the change target has been changed from amplitude $A_3$ to amplitude $A_7$.

After Step S42D, Step S44D, or Step S45D, the power supply voltage generator 32D applies, in Step S5D, the power supply voltage $V_5$ having the amplitude $A_7$ output from the control unit 34D in Step S42D, Step S44D, or Step S45D to the heater resistor 141 and the double bridge circuit 31. Thereafter, the treatment system 1D proceeds to Step S6.

Even with the configuration of the third embodiment described above, effects similar to those in the first embodiment can be obtained.

Modification 3-1 of Third Embodiment

Figure 35:
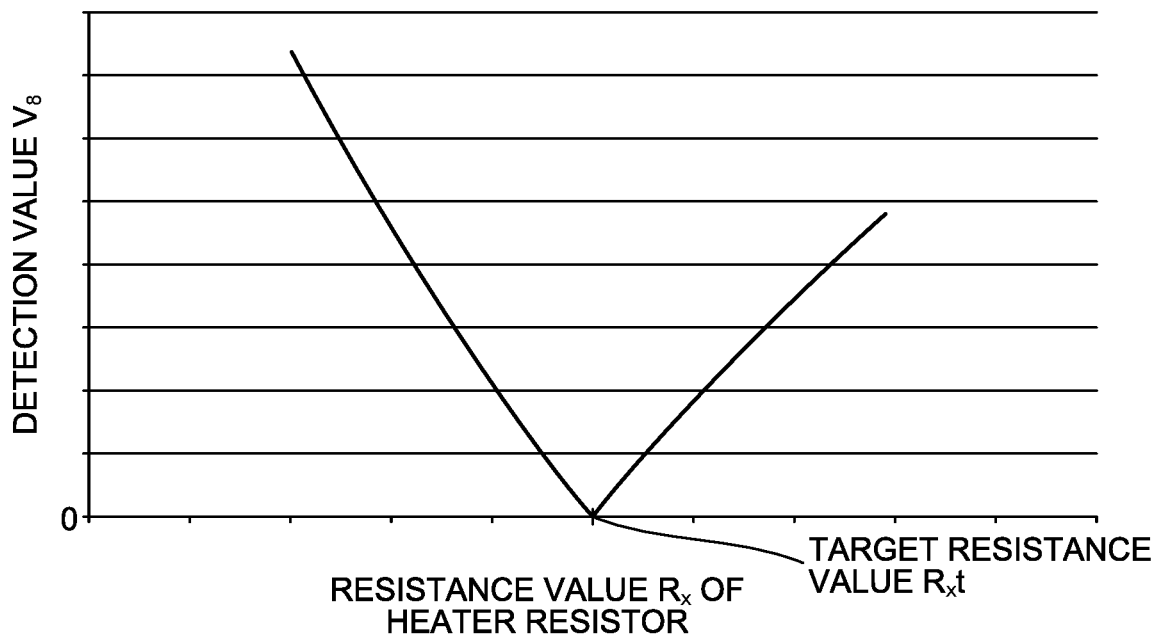
FIG. 35 is a diagram illustrating modification 3-1 of the third embodiment.
Figure 36:
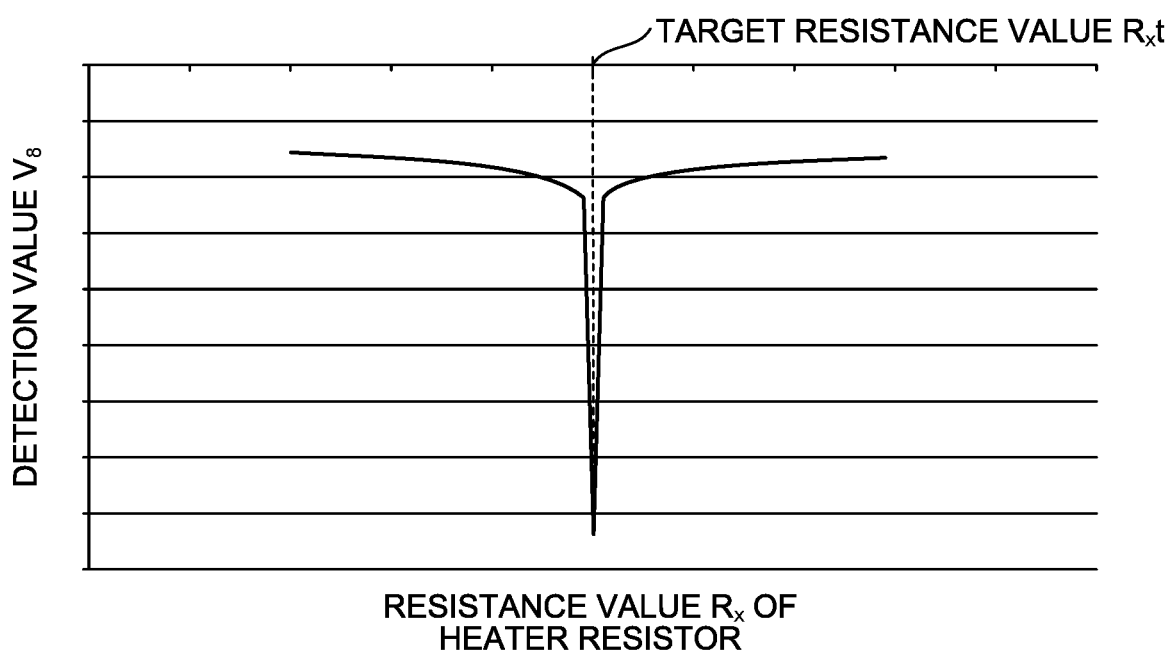
FIG. 36 is a diagram illustrating modification 3-1 of the third embodiment.
Figure 37:
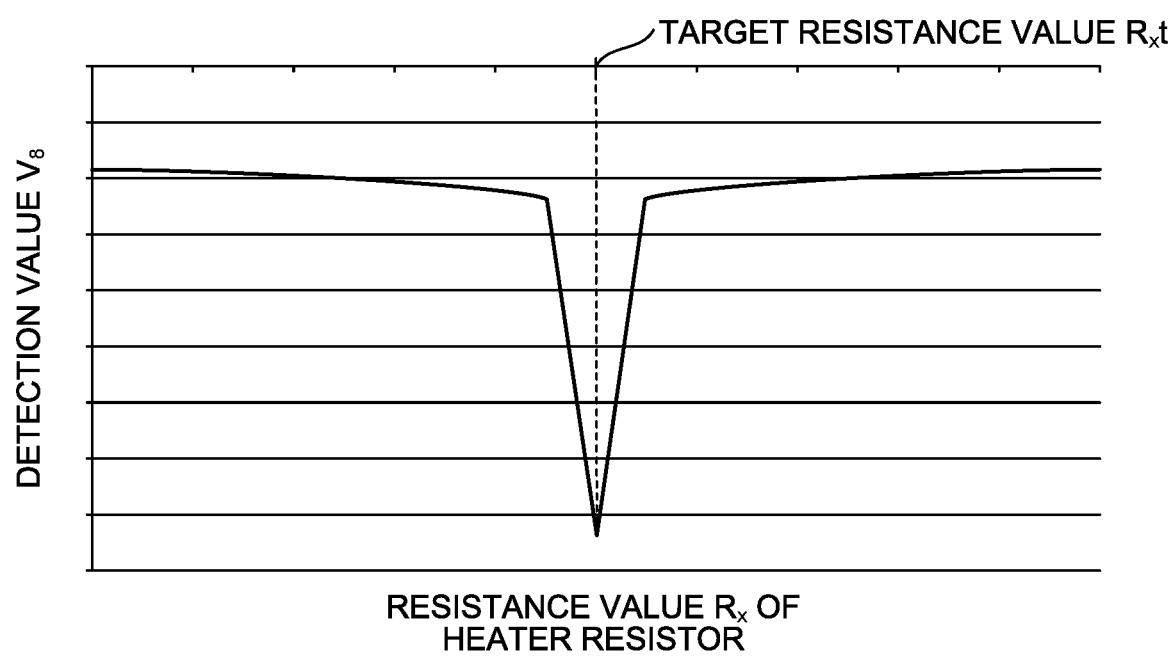
FIG. 37 is a diagram illustrating modification 3-1 of the third embodiment.

FIGS. 35 to 37 are diagrams illustrating modification 3-1 of the third embodiment. Specifically, FIGS. 35 to 37 are diagrams illustrating a relationship between the resistance value $R_x$ of the heater resistor 141 and the detection value $V_8$. FIG. 36 is a logarithmic diagram of the detection value $V_8$ illustrated in FIG. 35. FIG. 37 is an enlarged view of the range on the horizontal axis in FIG. 35.

Here, there is a relationship illustrated in FIG. 35 between the resistance value $R_x$ (heater temperature) of the heater resistor 141 and the detection value $V_8$.

Specifically, in the third embodiment described above, the detection value $V_8$ is calculated using half-wave rectifier circuits 3331 and 3351. Therefore, as illustrated in FIG. 35, the relationship between the resistance value $R_x$ (heater temperature) of the heater resistor 141 and the detection value $V_8$ is a relationship similar to that of FIG. 11 described above in modification 1-1.

Therefore, similarly to the above-described modification 1-1, the following processing may be executed in the third embodiment described above in order to judge whether the detection value $V_8$ is "0" with high accuracy.

Specifically, the control unit 34D obtains the logarithm of the detection value $V_8$ as illustrated in FIGS. 36 and 37. Subsequently, in a case where the logarithmic detection value $V_8$ is a local minimum, the control unit 34D judges that the detection value $V_8$ is "0".

Modification 3-2 of Third Embodiment

Figure 38:
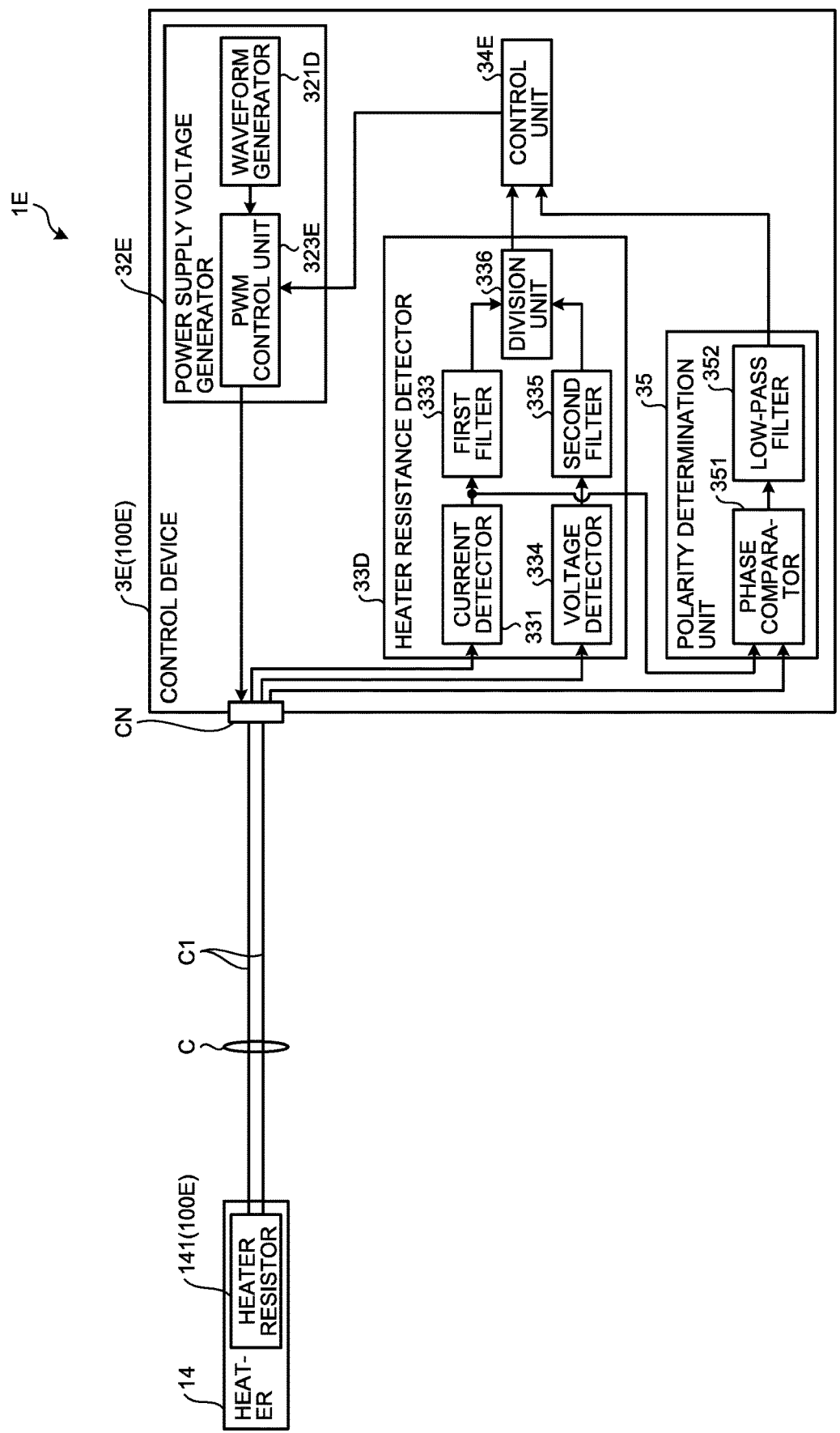
FIG. 38 is a diagram illustrating modification 3-2 of the third embodiment.
Figure 39:
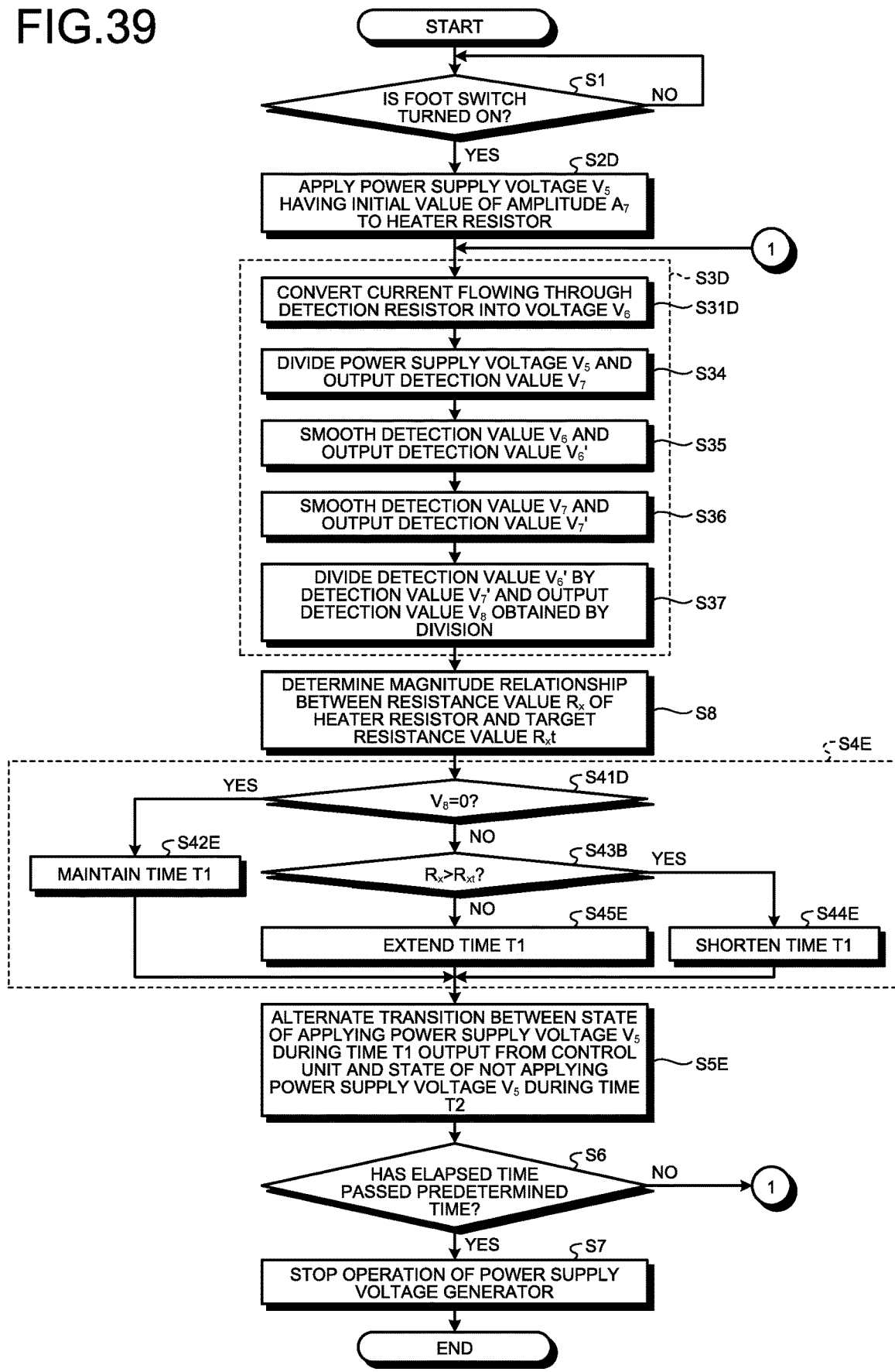
FIG. 39 is a diagram illustrating modification 3-2 of the third embodiment.
Figure 40:
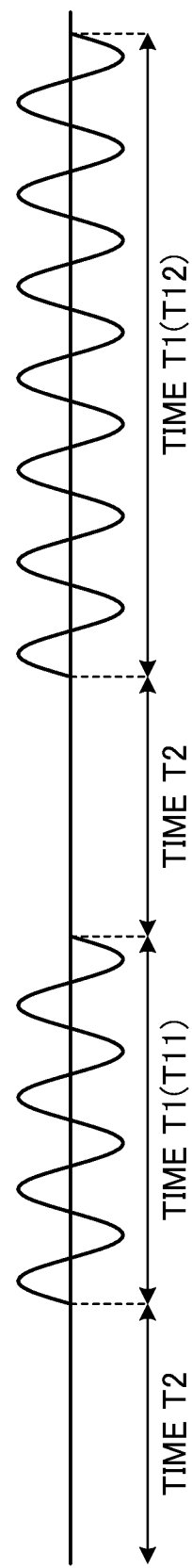
FIG. 40 is a diagram illustrating modification 3-2 of the third embodiment.

FIG. 38 to FIG. 40 are diagrams illustrating modification 3-2 of the third embodiment. Specifically, FIG. 38 is a block diagram illustrating a treatment system 1E according to modification 3-2. FIG. 39 is a flowchart illustrating a heating control method according to modification 3-2. FIG. 40 is a diagram illustrating a waveform of the power supply voltage $V_5$ according to modification 3-2.

In contrast to the treatment system 1D described above in the third embodiment, the treatment system 1E (control device 3E) according to modification 3-2 as illustrated in FIG. 38 employs a power supply voltage generator 32E including a PWM control unit 323E instead of the signal amplification unit 323 as well as employing a control unit 34E having a function different from that of the control unit 34D.

The PWM control unit 323E changes the time T1 (FIG. 40) for applying the power supply voltage $V_5$ (=$A_7 \sin \omega t$) generated by the waveform generator 321D to the heater resistor 141 and the double bridge circuit 31 under the control of the control unit 34E. In other words, the PWM control unit 323E performs pulse width modulation on the power supply voltage $V_5$. Furthermore, after the time T1, the PWM control unit 323E does not apply the power supply voltage $V_5$ to the heater resistor 141 or the double bridge circuit 31 during a fixed period of time T2 (FIG. 40). Subsequently, the PWM control unit 323E alternates transition between a state of applying the power supply voltage $V_5$ during the time T1 and a state of not applying the power supply voltage $V_5$ during the time T2 to the heater resistor 141 and the double bridge circuit 31 (FIG. 40).

Similarly to the control unit 35D described above in the third embodiment, the control unit 35E determines the magnitude relationship ($R_x < R_x t$ or $R_x > R_x t$) between the resistance value $R_x$ of the heater resistor 141 and the target resistance value $R_x t$, and together with this, calculates a deviation between the detection value $V_8$ output from the heater resistance detector 33D and the target value. Subsequently, the control unit 35E changes the above-described time T1 on the basis of the determined magnitude relationship and the calculated deviation. That is, in modification 3-2, the control unit 35E performs pulse width modulation on the power supply voltage $V_5$ (=$A_7 \sin \omega t$) via the PWM control unit 323E.

The heater resistor 141 and the control device 3E described above correspond to a heating device 100E (FIG. 38) according to the disclosure.

Next, a heating control method according to modification 3-2 will be described.

As illustrated in FIG. 39, the heating control method according to modification 3-2 employs Steps S4E and S5E instead of Steps S4D and S5D, respectively, compared to the heating control method described above in the third embodiment. Therefore, Steps S4E and S5E alone will be described below.

In Step S4E, the control unit 34E calculates the time T1 on the basis of the magnitude relationship ($R_x < R_xt$ or $R_x > R_xt$) between the resistance value $R_x$ of the heater resistor 141 and the target resistance value $R_xt$, and on the basis of the deviation between the detection value $V_8$ output from the heater resistance detector 33D and the target value.

Note that Step S4E includes Steps S41D, S42E, S43B, S44E, and S45E similar to Steps S41D, S42D, S43B, S44D, and S45D in Step S4D described above in the third embodiment. Here, Steps S42E, S44E, and S45E are different from Steps S42D, S44D, and S45D respectively only in that the change target has been changed from amplitude $A_7$ to time T1 along with the change from amplitude modulation to pulse width modulation.

For example, in Step S44E, the control unit 34E sets the time T1 shorter than the time T1 calculated at the immediately preceding loop (Steps S3D, S8, S4E, S5E, and S6) in accordance with the deviation between the resistance value $R_x$ and the target resistance value $R_xt$ in order to reduce the heater temperature, and then outputs the shortened time T1 (for example, time T11 (FIG. 40)) to the power supply voltage generator 32E (PWM control unit 323E).

Furthermore, for example, in Step S45E, the control unit 34E extends the time T1 to be longer than the time T1 calculated in the immediately preceding loop in accordance with the deviation between the resistance value $R_x$ and the target resistance value $R_xt$ in order to increase the heater temperature, and then outputs the extended time T1 (for example, time T12 (FIG. 40)) to the power supply voltage generator 32E (PWM control unit 323E).

After Step S42E, Step S44E, or Step S45E, the power supply voltage generator 32E performs, in Step S5E, for the heater resistor 141 and the double bridge circuit 31, alternate transition between a state of applying the power supply voltage $V_5$ (=$A_7 \sin \omega t$) during the time T1 output from the control unit 34E in Step S42E, Step S44E, or Step S45E, and a state of not applying the power supply voltage $V_5$ (=$A_7 \sin \omega t$) during the time T2 (FIG. 40). Thereafter, the treatment system 1E proceeds to Step S6.

It is also possible to have an effect similar to the above-described third embodiment even in the case of employing the configuration in which pulse width modulation is performed on the power supply voltage $V_5$ (=$A_7 \sin \omega t$) as in the above-described modification 3-2.

Modification 3-3 of Third Embodiment

Figure 41:
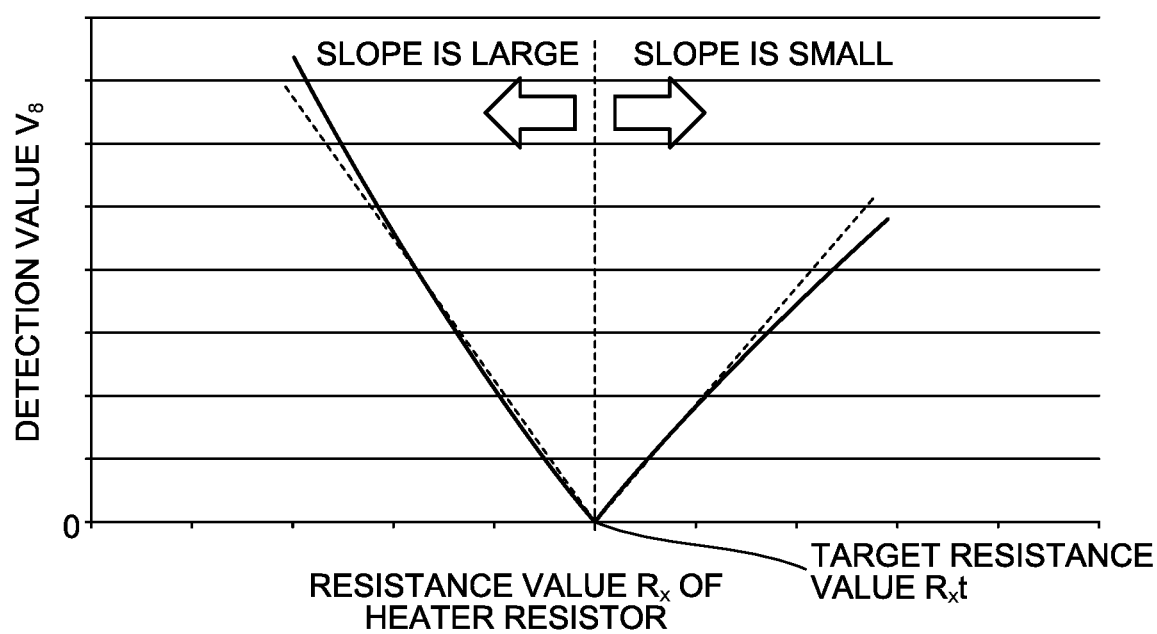
FIG. 41 is a diagram illustrating modification 3-3 of the third embodiment.

FIG. 41 is a diagram illustrating modification 3-3 of the third embodiment. Specifically, FIG. 41 is a diagram that corresponds to FIG. 35.

Meanwhile, as illustrated in FIG. 41, the relationship between the resistance value $R_x$ of the heater resistor 141 and the detection value $V_8$ is not a linear relationship in both the cases where the resistance value $R_x$ is greater than the target resistance value $R_xt$ and where the resistance value $R_x$ is smaller than the target resistance value $R_xt$. Specifically, the ratio (slope) of the increase (or decrease) of the detection value $V_8$ to a constant increase (or decrease) of the resistance value $R_x$ of the heater resistor 141 in a case where the resistance value $R_x$ is greater than the target resistance value $R_xt$ is smaller than the ratio (slope) of the increase (decrease) of the detection value $V_8$ to a constant increase (or decrease) of the resistance value $R_x$ in a case where the resistance value $R_x$ is smaller than the target resistance value $R_xt$.

That is, in the case where the resistance value $R_x$ of the heater resistor 141 is smaller than the target resistance value $R_xt$, the resistance value $R_x$ is likely to converge to the target resistance value $R_xt$ more rapidly than the case where the resistance value $R_x$ is greater than the target resistance value $R_xt$. Therefore, in consideration of the convergence of the resistance value $R_x$ of the heater resistor 141 to the target resistance value $R_xt$, it is not preferable to set a control proportional gain Gc(s) to the same level between the case where the resistance value $R_x$ is greater than the target resistance value $R_xt$ and the case where the resistance value $R_x$ is smaller than the target resistance value $R_xt$.

Therefore, Steps S44D and S45D may be executed as described below in the above-described third embodiment.

In Step S44D, since the resistance value $R_x$ of the heater resistor 141 is greater than the target resistance value $R_xt$, the control unit 34D sets the amplitude $A_7$ of the power supply voltage $V_5$ (=$A_7 \sin \omega t$) by a relatively large decrease, to be smaller than the amplitude $A_7$ calculated in the immediately preceding loop (loops of S3D, S8, S4D, S5D, and S6) (so as to increase the control proportional gain Gc(s)).

In contrast, in Step S45D, since the resistance value $R_x$ of the heater resistor 141 is smaller than the target resistance value $R_xt$, the control unit 34D sets the amplitude $A_7$ of the power supply voltage $V_5$ (=$A_7 \sin \omega t$), by a relatively small increase, to be greater than the amplitude $A_7$ calculated in the immediately preceding loop (so as to decrease the control proportional gain Gc(s)).

Fourth Embodiment

Next, a fourth embodiment of the disclosure will be described.

In the following description, identical reference numerals are given to the components and steps similar to those in the first and third embodiments described above, and detailed description thereof will be omitted or simplified.

Figure 42:
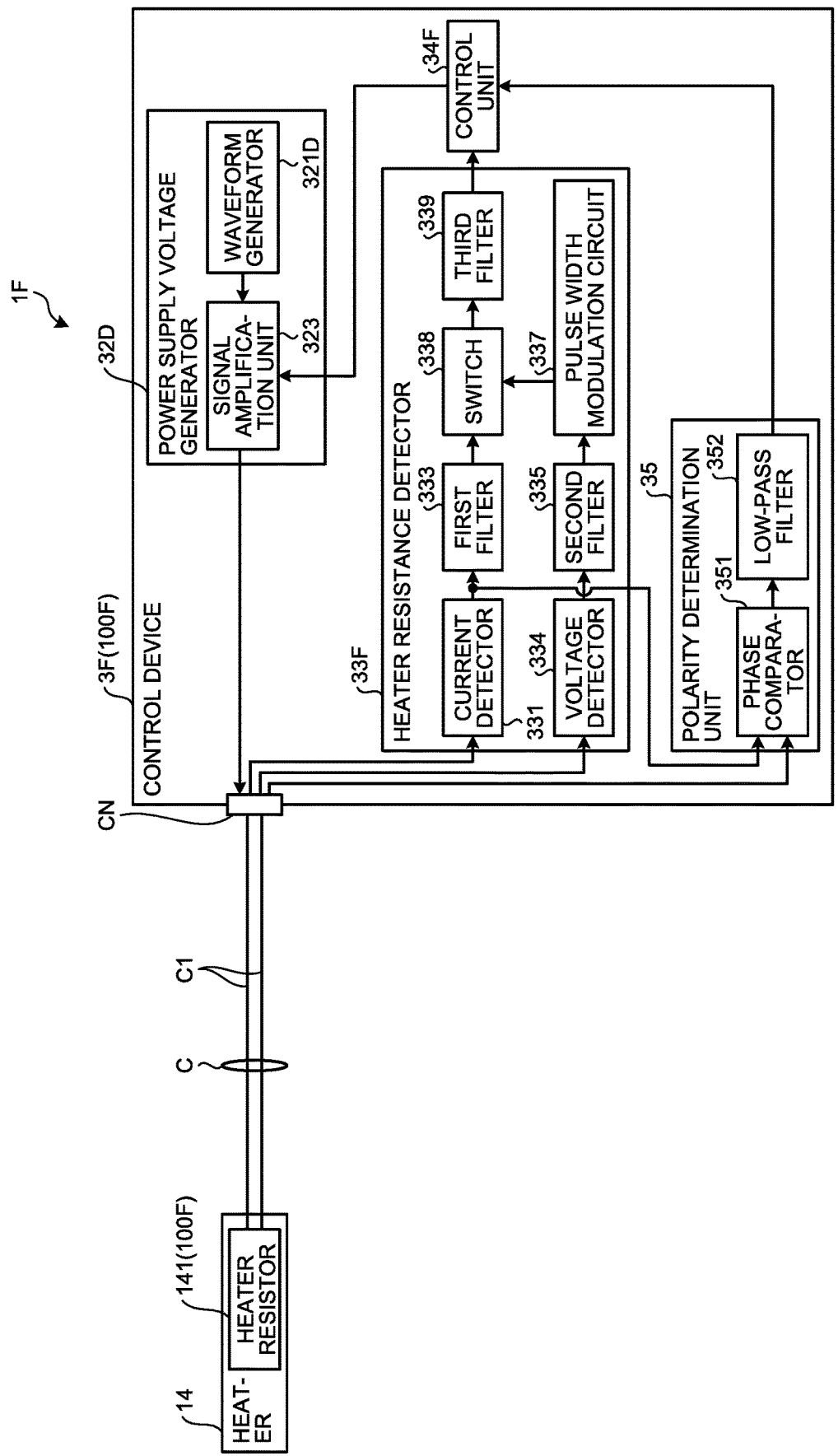
FIG. 42 is a block diagram illustrating a treatment system according to a fourth embodiment.
Figure 43:
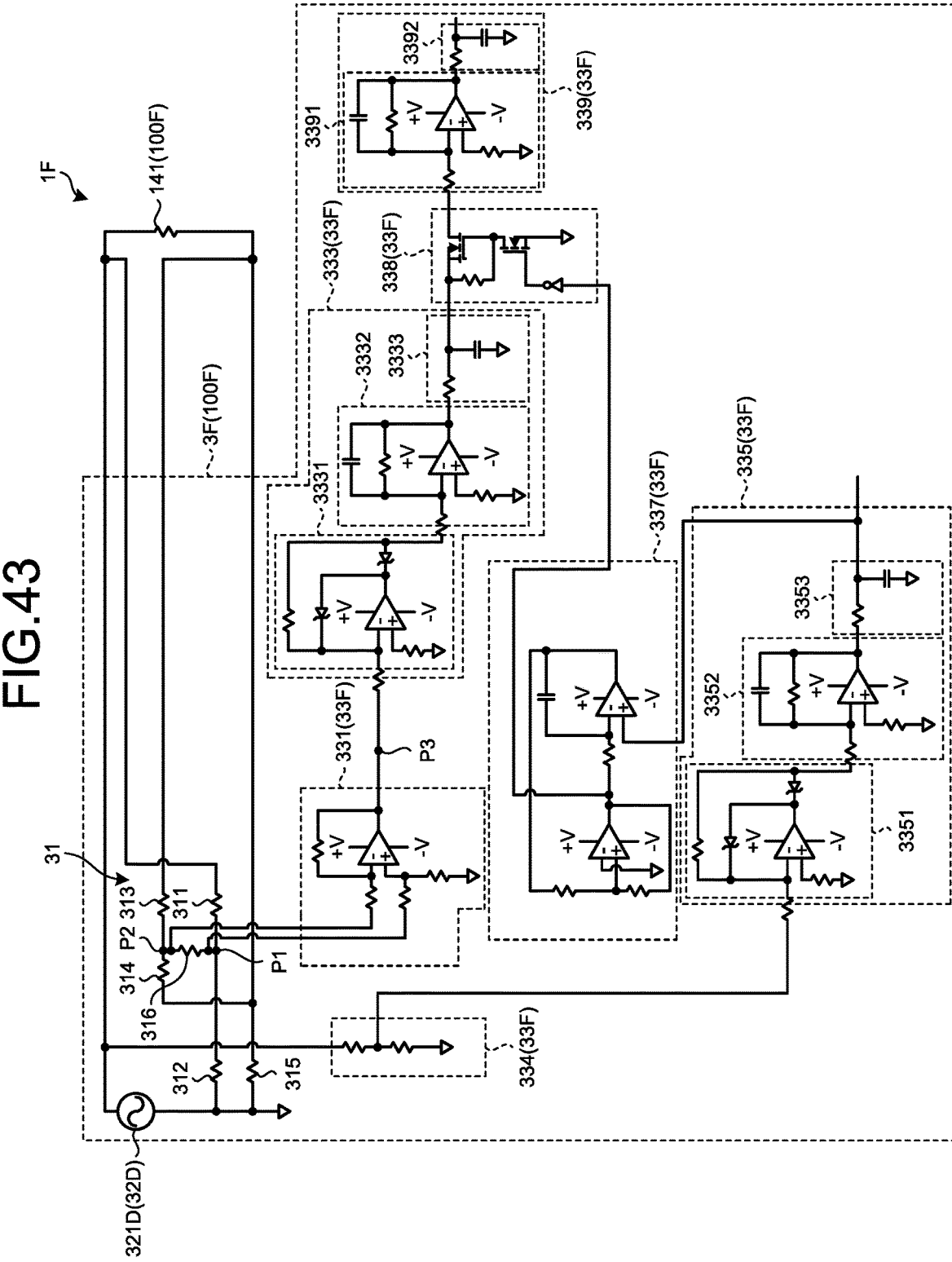
FIG. 43 is a diagram illustrating a circuit configuration of a treatment system.

FIG. 42 is a block diagram illustrating a treatment system 1F according to the fourth embodiment. FIG. 43 is a diagram illustrating a circuit configuration of the treatment system 1F. Note that FIG. 42 omits illustration of the double bridge circuit 31 similarly to FIGS. 3 and 31. Also note that FIG. 43 omits illustration of the signal amplification unit 323, a control unit 34F and the polarity determination unit 35 for convenience of explanation.

As illustrated in FIG. 42 or 43, the treatment system 1F (control device 3F) according to the fourth embodiment employs a heater resistance detector 33F and a control unit 34F having functions different from the heater resistance detector 33D and the control unit 34D respectively, compared to the treatment system 1D described above in the third embodiment.

Note that the power supply voltage of the power supply voltage generator 32D according to the fourth embodiment will be referred to as a power supply voltage $V_9$ (=$A_{10} \sin \omega t$) in order to distinguish it from the power supply voltage $V_5$ (=$A_7 \sin \omega t$) described above in the third embodiment.

As illustrated in FIG. 42 or 43, the heater resistance detector 33F includes a pulse width modulation circuit 337, a switch 338, and a third filter 339 in addition to the current detector 331, the first and second filters 333 and 335, and the voltage detector 334 described above in the third embodiment.

Note that the detection value of the current detector 331 according to the fourth embodiment will be referred to as a detection value $V_{10}$ (=$A_{11} \cos \omega t$) to distinguish it from the detection value $V_6$ (=$A_8 \cos \omega t$) described above in the third embodiment. Furthermore, the detection value of the first filter 333 according to the fourth embodiment will be referred to as a detection value $V_{10}'$ in the following Formula (5) to distinguish it from the detection value $V_6'$ described above in the third embodiment. Furthermore, the detection value of the voltage detector 334 according to the fourth embodiment will be referred to as a detection value $V_{11}$ ($=A_{12}$ sin ωt) in order to distinguish it from the detection value $V_7$ ($=A_9$ sin ωt) described above in the third embodiment. Furthermore, the detection value of the second filter 335 according to the fourth embodiment will be referred to as a detection value $V_{11}'$ in the following Formula (6) to distinguish it from the detection value $V_7'$ described above in the third embodiment.

$$V_{10}' = \frac{A_{11}}{\sqrt{2}} \quad (5)$$

$$V_{11}' = \frac{A_{12}}{\sqrt{2}} \quad (6)$$

As illustrated in FIG. 43, the pulse width modulation circuit 337 includes, for example, a triangular wave oscillation circuit that oscillates a reference triangular wave, a comparator circuit that compares the amplitude of the triangular wave oscillated by the triangular wave oscillation circuit with the detection value $V_{11}'$ of the second filter 335, or the like, and generates and outputs a switch control signal.

The switch 338 is turned on in response to the switch control signal output from the pulse width modulation circuit 337, and allows the detection value $V_{10}'$ output from the first filter 333 to pass through the third filter 339 only during the switch ON state.

The third filter 339 includes an integration circuit 3391 and a low-pass filter 3392, as illustrated in FIG. 43.

As illustrated in FIG. 43, the integration circuit 3391 includes a capacitor and an operational amplifier, for example. Subsequently, the integration circuit 3391 integrates and outputs the output signal (the detection value $V_{10}'$ of the first filter 333) from the switch 338.

As illustrated in FIG. 43, the low-pass filter 3392 includes: a capacitor connected in parallel to the input signal; and a resistor connected in series to the input signal. Subsequently, an output signal from the integration circuit 3391 is input to the low-pass filter 3392.

Subsequently, the third filter 339 (low-pass filter 3392) outputs a detection value $V_{10}''$ represented by the following Formula (7) to control unit 34F.

$$V_{10}'' = \frac{A_{11}'}{\sqrt{2}} \quad (7)$$

Figure 44:
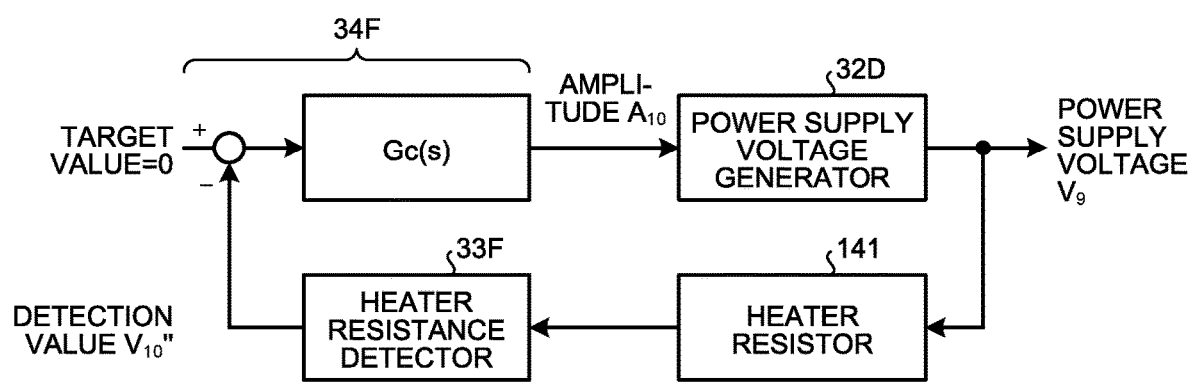
FIG. 44 is a block diagram illustrating feedback control performed by a control unit.

FIG. 44 is a block diagram illustrating feedback control performed by the control unit 34F.

Similarly to the control unit 34D described above in the third embodiment, the control unit 34F determines a magnitude relationship ($R_x < R_x t$ or $R_x > R_x t$) between the resistance value $R_x$ of the heater resistor 141 and the target resistance value $R_x t$ on the basis of the signal (voltage $V_0$) output from the polarity determination unit 35. Furthermore, the control unit 34F calculates a deviation between the detection value $V_{10}''$ output from the heater resistance detector 33F (the third filter 339) and the target value "0". Subsequently, the control unit 34F calculates an amplitude $A_{10}$ of the power supply voltage $V_9$ ($=A_{10}$ sin ωt) on the basis of the determined magnitude relationship and the calculated deviation, and then outputs the calculated amplitude $A_{10}$ to the power supply voltage generator 32D (the signal amplification unit 323) as a control target. In response to this, the power supply voltage generator 32D applies the power supply voltage $V_9$ having the amplitude $A_{10}$ calculated by the control unit 34F to the heater resistor 141 and the double bridge circuit 31. That is, in the fourth embodiment, the control unit 34F performs amplitude modulation on the power supply voltage $V_9$ via the signal amplification unit 323 similarly to the control unit 34D described above in the third embodiment.

The heater resistor 141 and the control device 3F described above correspond to a heating device 100F (FIGS. 42 and 43) according to the disclosure.

Next, operation (heating control method) of the above-described treatment system 1F will be described.

Figure 45:
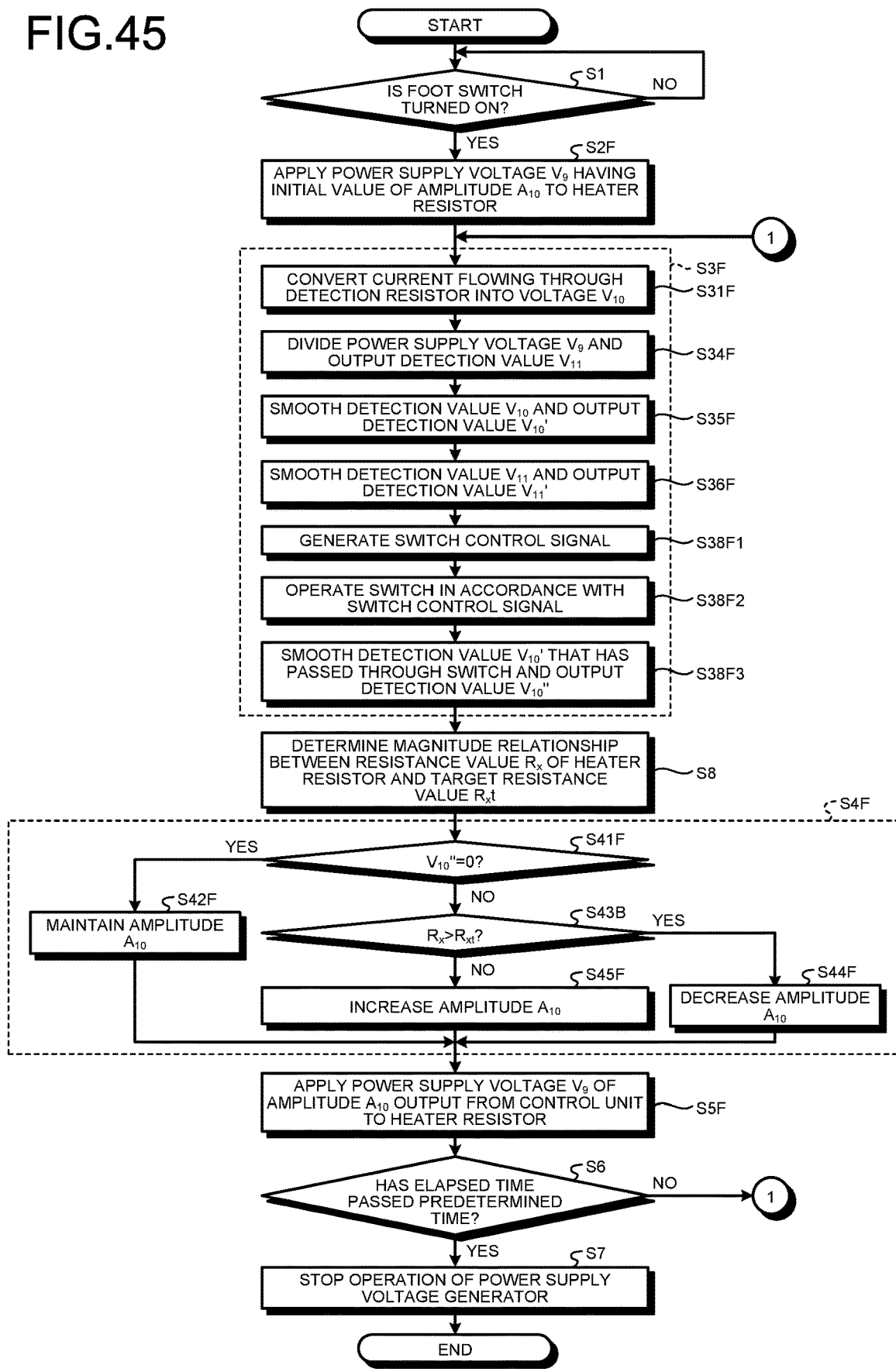
FIG. 45 is a flowchart illustrating a heating control method.

FIG. 45 is a flowchart illustrating a heating control method.

As illustrated in FIG. 45, the heating control method according to the fourth embodiment employs Steps S2F, S3F, S4F, and S5F instead of Steps S2D, S3D, S4D, and S5D, compared to the heating control method described above in the third embodiment. Therefore, Steps S2F, S3F, S4F, and S5F alone will be described below.

Step S2F is a process similar to Step S2D described above in the third embodiment, except that the description of the power supply voltage has been changed from the power supply voltage $V_5$ to the power supply voltage $V_9$ ($=A_{10}$ sin ωt).

After Step S2F, the heater resistance detector 33F calculates a detection value $V_{10}''$ and outputs the calculated value to the control unit 34F (Step S3F).

Specifically, Step S3F includes Steps S31F, S34F, S35F, and S36F similar to Steps S31D, S34 to S36 described above in the third embodiment, and additional Steps S38F1, S38F2, and S38F3. Here, Step S31F is different from Step S31D only in that the description of the detection value of current detector 331 has been changed from the detection value $V_6$ to the detection value $V_{10}$ ($=A_{11}$ cos ωt). Moreover, Step S34F is different from Step S34 only in that the description of the detection value of the voltage detector 334 has been changed from the detection value $V_7$ to the detection value $V_{11}$ ($=A_{12}$ sin ωt). Furthermore, Step S35F is different from Step S35 only in that the description of the detection value of the first filter 333 has been changed from the detection value $V_6'$ to the detection value $V_{10}'$. Moreover, Step S36F is different from Step S36 only in that the description of the detection value of second filter 335 has been changed from the detection value $V_7'$ to the detection value $V_{11}'$.

Although FIG. 45 illustrates the procedure in which Step S34F is executed after Step S31F for convenience of explanation, Step S31F and Step S34F are to be executed in parallel in practice. Step S35F and Step S36F are also executed in parallel.

Step S38F1 is executed after Step S36F.

Specifically, in Step S38F1, the pulse width modulation circuit 337 compares the amplitude of the reference triangular wave with the detection value $V_{11}'$ of the second filter 335 in Step S36F to generate and output a switch control signal.

After Step S38F1, the switch 338 is turned on in response to the switch control signal output from the pulse width modulation circuit 337 in Step S38F1, and allows the detection value $V_{10}'$ output from the first filter 333 in Step S35F to pass through the third filter 339 only during the switch ON state (Step S38F2).

After Step S38F2, the third filter 339 uses the integration circuit 3391 and the low-pass filter 3392 to smooth the detection value $V_{10}'$ that has passed through the switch 338 in Step S38F2, and then outputs the detection value $V_{10}''$ (Step S38F3).

Although FIG. 45 illustrates the procedure in which Step S8 is executed after Step S3F for convenience of explanation, Step S3F and Step S8 are to be executed in parallel in practice.

After Step S8, the control unit 34F calculates the amplitude $A_{10}$ of the power supply voltage $V_9$ (=$A_{10}$ sin ωt) on the basis of the magnitude relationship determined in Step S8 and on the basis of the deviation between the detection value $V_{10}''$ output from the heater resistance detector 33F and the target value "0" (Step S4F).

Step S4F includes Steps S41F, S42F, S43B, S44F, and S45F similar to Steps S41D, S42D, S43B, S44D, and S45D in Step S4D described above in the third embodiment. Here, Step S41F is different from Step S41D only in that the comparison target with the target value "0" has been changed from the detection value $V_8$ to the detection value $V_{10}''$. Furthermore, Steps S42F, S44F, and S45F are different from Steps S42D, S44D, and S45D respectively only in that the change target has been changed from the amplitude $A_7$ to the amplitude $A_{10}$.

After Step S42F, Step S44F, or Step S45F, the power supply voltage generator 32D applies, in Step S5F, the power supply voltage $V_9$ having the amplitude $A_{10}$ output from the control unit 34F in Step S42F, Step S44F, or Step S45F to the heater resistor 141 and the double bridge circuit 31. Thereafter, the treatment system 1F proceeds to Step S6.

The following is a description of an example of transitions, performed by the above-described heating control method, of the power supply voltage $V_9$, the detection value $V_{11}'$ of the second filter 335, the switch control signal generated by the pulse width modulation circuit 337, the detection value $V_{10}'$ of the first filter 333 passing through the switch 338 (detection value $V_{10}'$ to be input to the third filter 339), and the detection value $V_{10}''$ of the third filter 339.

Figure 46:
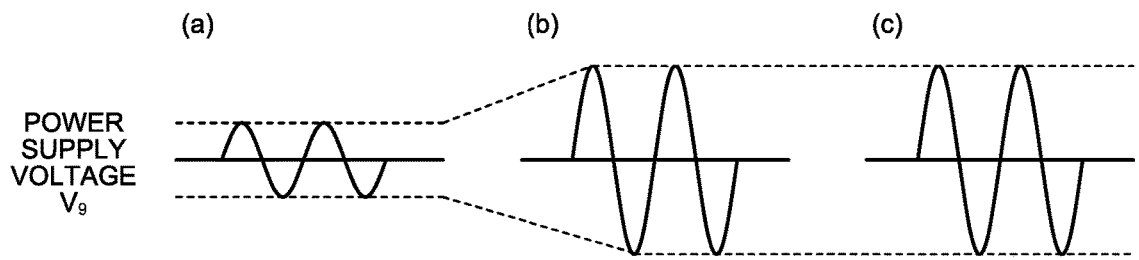
FIG. 46 is a diagram illustrating a transition of a power supply voltage.
Figure 47:
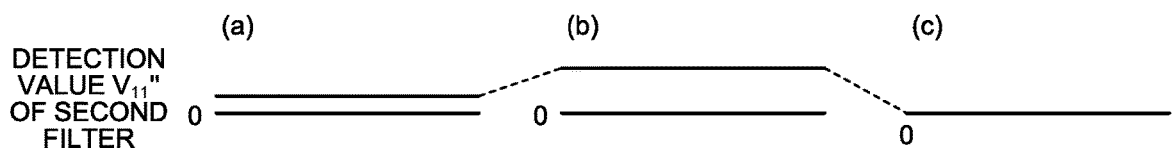
FIG. 47 is a diagram illustrating a transition of a detection value of a second filter.
Figure 48:
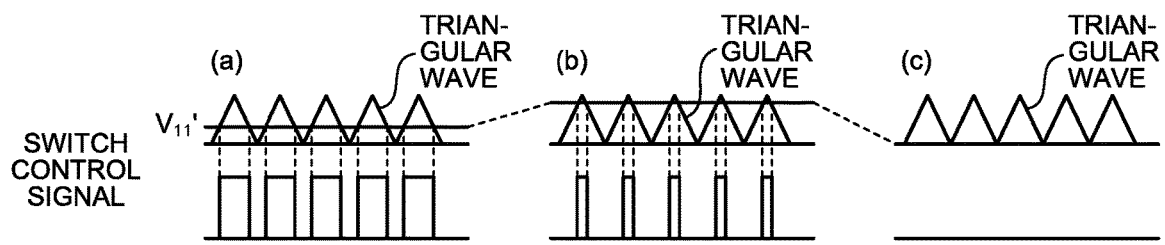
FIG. 48 is a diagram illustrating a transition of a switch control signal generated by a pulse width modulation circuit.
Figure 49:
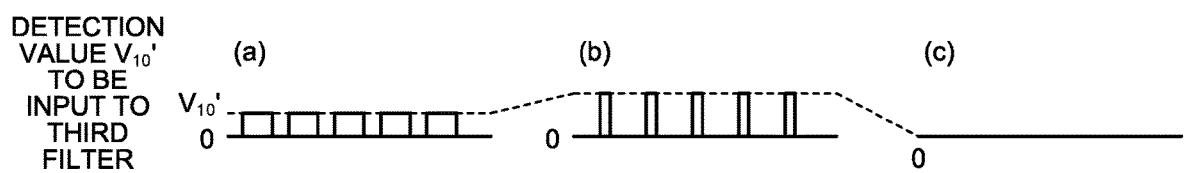
FIG. 49 is a diagram illustrating a transition of a detection value of a first filter (detection value input to a third filter) passing through a switch.
Figure 50:
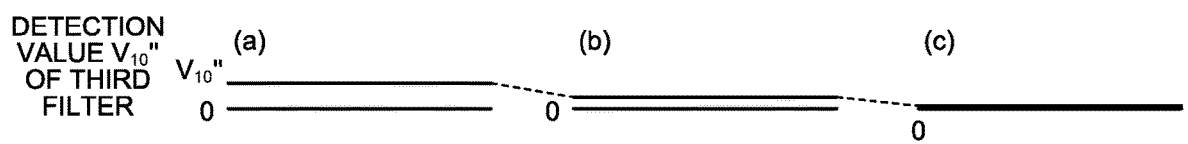
FIG. 50 is a diagram illustrating a transition of a detection value of a third filter.

FIG. 46 is a diagram illustrating a transition of the power supply voltage $V_9$. FIG. 47 is a diagram illustrating a transition of the detection value $V_{11}'$ of the second filter 335. FIG. 48 is a diagram illustrating a transition of the switch control signal generated by the pulse width modulation circuit 337. FIG. 49 is a diagram illustrating a transition of the detection value $V_{10}'$ of the first filter 333 passing through the switch 338 (the detection value $V_{10}'$ to be input to the third filter 339). FIG. 50 is a diagram illustrating a transition of the detection value $V_{10}''$ of the third filter 339. Note that (a) of FIG. 46, (a) of FIG. 47, (a) of FIG. 48, (a) of FIG. 49, and (a) of FIG. 50 illustrate a case where the resistance value $R_x$ of the heater resistor 141 is sufficiently smaller than the target resistance value $R_x t$ (a case where the heater temperature is sufficiently lower than the target temperature). (b) of FIG. 46, (b) of FIG. 47, (b) of FIG. 48, (b) of FIG. 49, and (b) of FIG. 50 illustrate a case where the resistance value $R_x$ of the heater resistor 141 approaches the target resistance value $R_x t$ (a case where the heater temperature approaches the target temperature) as a result of heating control, compared with the states illustrated in (a) of FIG. 46, (a) of FIG. 47, (a) of FIG. 48, (a) of FIG. 49, (a) of FIG. 50. (c) of FIG. 46, (c) of FIG. 47, (c) of FIG. 48, (c) of FIG. 49, and (c) of FIG. 50 illustrate a case where the resistance value $R_x$ of the heater resistor 141 matches the target resistance value $R_x t$ (a case where the heater temperature matches the target temperature) as a result of heating control.

As observed in comparison between (a) of FIG. 46 and (b) of FIG. 46, in a case where the resistance value $R_x$ of the heater resistor 141 is smaller than the target resistance value $R_x t$ (the heater temperature is lower than the target temperature), the power supply voltage $V_9$ is set such that the amplitude $A_{10}$ will be increased by the processes in Steps S45F and S5F in order to increase the resistance value $R_x$ of the heater resistor 141 (increase the heater temperature). In a case where the resistance value $R_x$ of the heater resistor 141 matches the target resistance value $R_x t$ (in a case where the heater temperature matches the target temperature) as illustrated in (c) of FIG. 46, the power supply voltage $V_9$ is set to be maintained to have the amplitude $A_{10}$ ((b) of FIG. 46) of the power supply voltage $V_9$ in the immediately preceding loop (a loop including Steps S3F, S4F, S5F, and S6) by the processes in Steps S42F and S5F.

The detection value $V_{11}'$ of the second filter 335 is a value obtained by smoothing the detection value $V_{11}$ obtained by dividing the power supply voltage $V_9$ by the half-wave rectifier circuit 3351, the integration circuit 3352, and the low-pass filter 3353. Therefore, the detection value $V_{11}'$ changes in accordance with the amplitude modulation of the power supply voltage $V_9$ as illustrated in (a) and (b) of FIG. 47.

As illustrated in (a) and (b) of FIG. 48, in the switch control signal, switch ON time at a high level changes in accordance with the detection value $V_{11}'$ of the second filter 335 (amplitude modulation of the power supply voltage $V_9$). Specifically, an increase in the amplitude $A_{10}$ of the power supply voltage $V_9$ increases the detection value $V_{11}'$, leading to reduction of the switch ON time in the switch control signal. In contrast, a decrease in the amplitude $A_{10}$ of the power supply voltage $V_9$ decreases the detection value $V_{11}'$ leading to extension of the switch ON time in the switch control signal.

As illustrated in FIG. 49, the detection value $V_{10}'$ output from the first filter 333 passes through the switch 338 during the switch ON time in the switch control signal.

As illustrated in (a) and (b) of FIG. 50, the detection value $V_{10}''$ of the third filter 339 approaches "0" as the resistance value $R_x$ of the heater resistor 141 approaches the target resistance value $R_x t$ (as the heater temperature approaches the target temperature) by the processes of Steps S45F and S5F. Furthermore, as illustrated in (c) of FIG. 50, the detection value $V_{10}''$ indicates "0" in a case where the resistance value $R_x$ of the heater resistor 141 matches the target resistance value $R_x t$ (in a case where the heater temperature matches the target temperature).

Here, the detection value $V_{10}$ of the current detector 331 (the detection value $V_{10}'$ of the first filter 333) undergoes thinning of a first current component according to the disclosure that changes with the amplitude modulation of the power supply voltage $V_9$, in accordance with the switch control signal (FIG. 49). Therefore, as observed in comparison of (a) to (c) of FIG. 46 with (a) to (c) of FIG. 50, the detection value $V_{10}''$ after thinning would not change in accordance with the amplitude modulation of the power supply voltage $V_9$, but would change in accordance with the change in the heater temperature (change in the resistance value $R_x$ of the heater resistor 141). That is, the detection value $V_{10}''$ corresponds to the second current component according to the disclosure.

Even with the configuration of the fourth embodiment described above, effects similar to those in the first embodiment can be obtained.

Fifth Embodiment

Next, a fifth embodiment of the disclosure will be described.

In the following description, identical reference numerals are given to the components and steps similar to those in the first and third embodiments described above, and detailed description thereof will be omitted or simplified.

Figure 51:
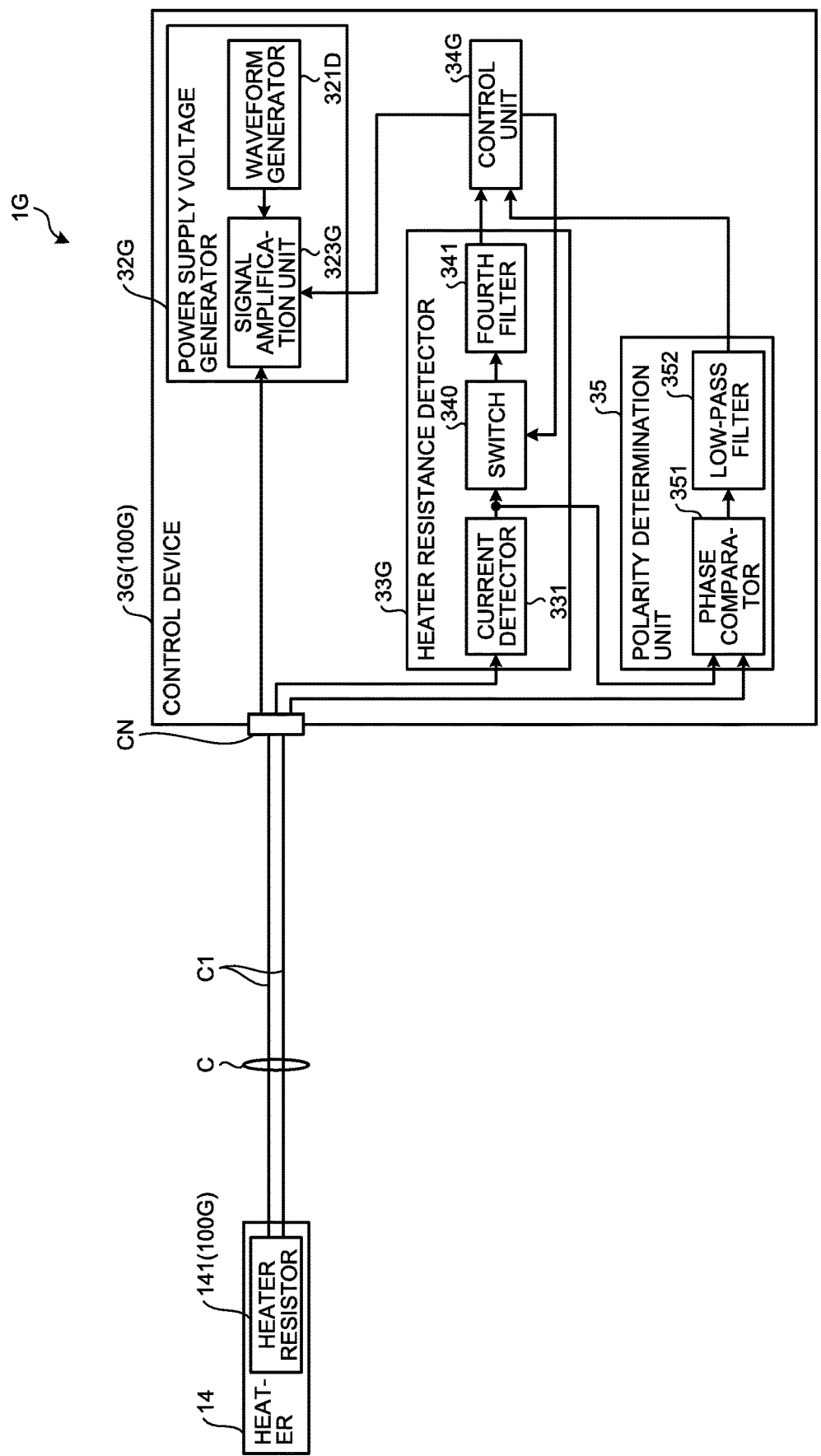
FIG. 51 is a block diagram illustrating a treatment system according to a fifth embodiment.

FIG. 51 is a block diagram illustrating a treatment system 1G according to the fifth embodiment.

In contrast to the treatment system 1D described above in the third embodiment, a treatment system 1G (control device 3G) according to the fifth embodiment as illustrated in FIG. 51 employs a power supply voltage generator 32G that includes a signal amplification unit 323G instead of the signal amplification unit 323 as well as employing a heater resistance detector 33G and a control unit 34G having functions different from those of the heater resistance detector 33D and the control unit 34D, respectively.

Note that the power supply voltage of the waveform generator 321D according to the fifth embodiment will be referred to as a power supply voltage $V_{14}$ ($=A_{14} \sin \omega t$) in order to distinguish it from the power supply voltage $V_5$ ($=A_7 \sin \omega t$) described above in the third embodiment. The amplitude $A_{14}$ is a constant value.

Under the control of the control unit 34G, the signal amplification unit 323G changes the amplitude (performs amplitude modulation) of the power supply voltage $V_{14}$ generated at the waveform generator 321D during first time T3 for each of a fixed period of time T5 (sum of the first time T3 and second time T4 (refer to FIGS. 54 and 55)). In the following, the amplitude after the amplitude modulation will be referred to as an amplitude $A_{13}$ (power supply voltage after amplitude modulation: power supply voltage $V_{14}$ ($=A_{13} \sin \omega t$)) for convenience of explanation.

Figure 54:
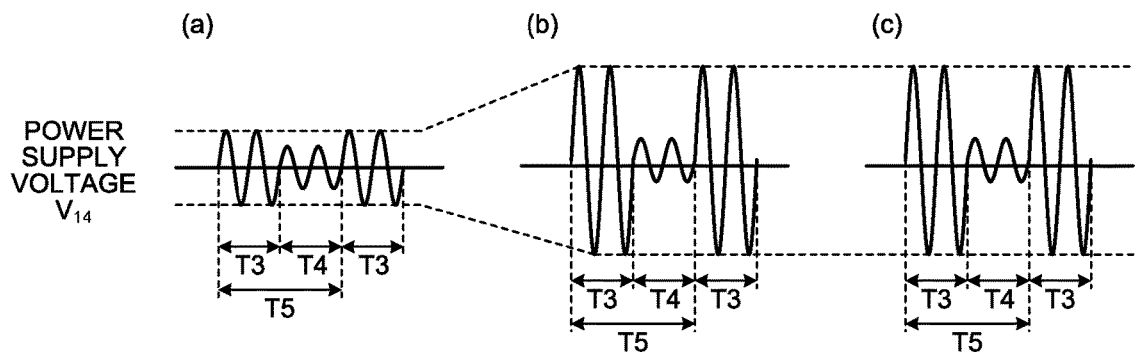
FIG. 54 is a diagram illustrating a transition of a power supply voltage.
Figure 55:
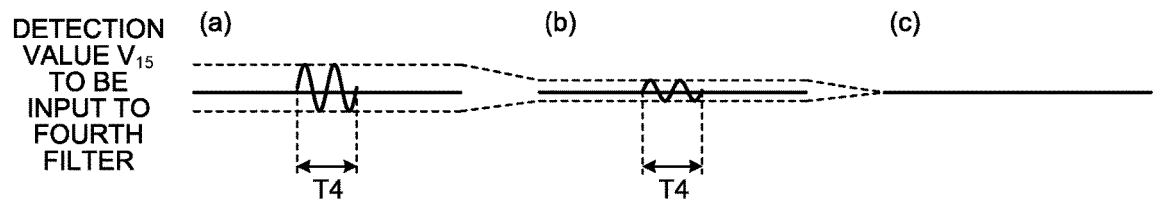
FIG. 55 is a diagram illustrating a transition of a detection value (detection value input to a fourth filter) of a current detector passing through a switch.

That is, the power supply voltage generator 32G alternately transitions between a state of applying the power supply voltage $V_{14}$ ($=A_{13} \sin \omega t$) to the heater resistor 141 and the double bridge circuit 31 during the first time T3 (refer to FIGS. 54 and 55) and a state of applying the power supply voltage $V_{14}$ ($=A_{14} \sin \omega t$) having the constant amplitude $A_{14}$ during the second time T4 (refer to FIGS. 54 and 55).

As illustrated in FIG. 51, the heater resistance detector 33G includes a switch 340 and a fourth filter 341 in addition to the current detector 331 described above in the third embodiment.

Note that the detection value of the current detector 331 according to the fifth embodiment will be referred to as a detection value $V_{15}$ ($=A_{15} \cos \omega t$) to distinguish it from the detection value $V_6$ ($=A_8 \cos \omega t$) described above in the third embodiment.

Under the control of the control unit 34G, the switch 340 is turned on during the first time T3 and allows the detection value $V_{15}$ output from the current detector 331 to pass through the fourth filter 341 only during the switch ON state.

Although not specifically illustrated, the fourth filter 341 includes a half-wave rectifier circuit, an integration circuit, and a low-pass filter, similarly to the first and second filters 333 and 335 described above in the third embodiment. Subsequently, the fourth filter 341 by uses the half-wave rectifier circuit, the integration circuit, and the low-pass filter to smooth the detection value $V_{15}$ that has passed through the switch 340 and outputs a detection value $V_{15}'$ represented by the following Formula (8).

$$V_{15}' = \frac{A_{15}}{\sqrt{2}} \tag{8}$$

Figure 52:
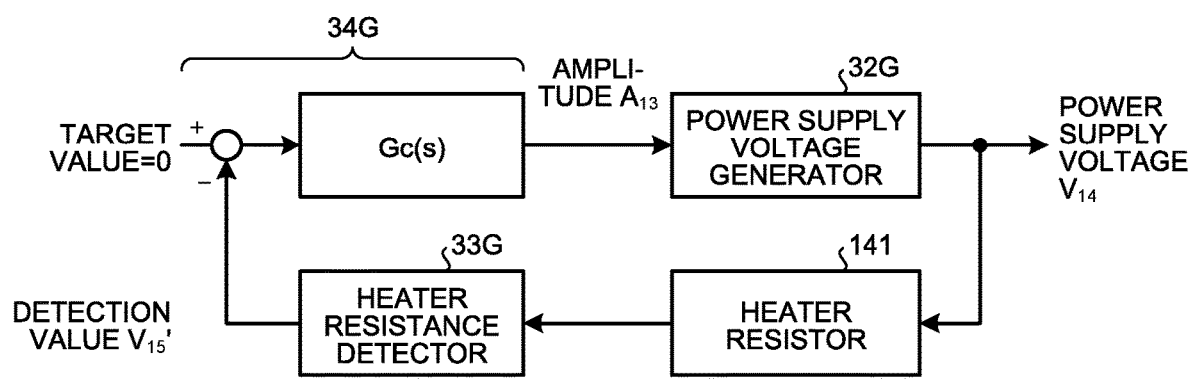
FIG. 52 is a block diagram illustrating feedback control performed by a control unit.

FIG. 52 is a block diagram illustrating feedback control performed by the control unit 34G.

Similarly to the control unit 34D described above in the third embodiment, the control unit 34G determines a magnitude relationship ($R_x < R_x t$ or $R_x > R_x t$) between the resistance value $R_x$ of the heater resistor 141 and the target resistance value $R_x t$ on the basis of the signal (voltage $V_0$) output from the polarity determination unit 35. Furthermore, the control unit 34G calculates a deviation between the detection value $V_{15}'$ output from the heater resistance detector 33G (the fourth filter 341) and the target value "0". Subsequently, the control unit 34G calculates the amplitude $A_{13}$ of the power supply voltage $V_{14}$ ($=A_{13} \sin \omega t$) during the first time T3 on the basis of the determined magnitude relationship and the calculated deviation, and then outputs the calculated amplitude $A_{13}$ to the power supply voltage generator 32G (the signal amplification unit 323G) as a control target. In response to this, the power supply voltage generator 32G applies the power supply voltage $V_{14}$ having the amplitude $A_{13}$ calculated by the control unit 34G to the heater resistor 141 and the double bridge circuit 31 during the first time T3. That is, in the fifth embodiment, the control unit 34G performs amplitude modulation on the power supply voltage $V_{14}$ via the signal amplification unit 323G, similarly to the control unit 34D described above in the third embodiment.

The heater resistor 141 and the control device 3G described above correspond to a heating device 100G (FIG. 51) according to the disclosure.

Next, operation (heating control method) of the above-described treatment system 1G will be described.

Figure 53:
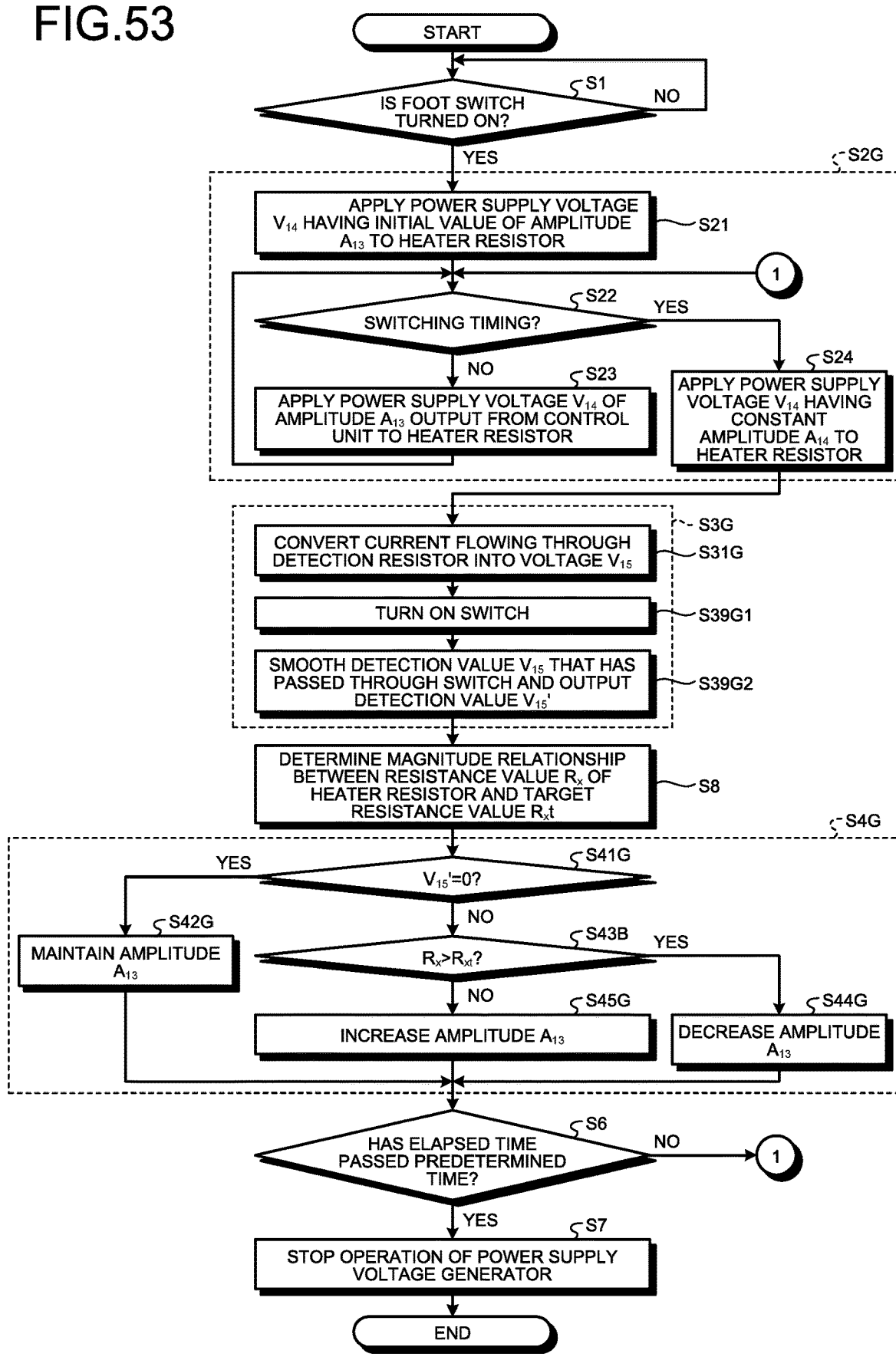
FIG. 53 is a flowchart illustrating a heating control method.

FIG. 53 is a flowchart illustrating a heating control method.

As illustrated in FIG. 53, the heating control method according to the fifth embodiment omits Step S5D and employs Steps S2G, S3G, and S4G instead of Steps S2D, S3D, and S4D, compared to the heating control method described above in the third embodiment. Therefore, Steps S2G, S3G, and S4G alone will be described below.

Step S2G includes Steps S21 to S24.

Specifically, the control unit 34G outputs an initial value of the amplitude $A_{13}$ of the power supply voltage $V_{14}$ ($=A_{13} \sin \omega t$) to the power supply voltage generator 32G (signal amplification unit 323G). Subsequently, the power supply voltage generator 32G applies the power supply voltage $V_{14}$ having the initial value of the amplitude $A_{13}$ to the heater resistor 141 and the double bridge circuit 31 (Step S21).

After Step S21, the control unit 34G judges whether a switching timing Tm (refer to FIGS. 54 and 55) for setting the amplitude of the power supply voltage $V_{14}$ to the constant amplitude $A_{14}$ has arrived (Step S22).

In a case where it is judged that the switching timing Tm has not arrived, the control unit 34G outputs a control signal to the power supply voltage generator 32G (signal amplification unit 323G). Subsequently, the power supply voltage generator 32G applies the power supply voltage $V_{14}$ having the amplitude $A_{13}$ output from the control unit 34G to the heater resistor 141 and the double bridge circuit 31 (Step S23). Thereafter, the treatment system 1G returns to Step S22.

In contrast, in a case where it is judged that the switching timing Tm has arrived, the control unit 34G outputs a control signal to the power supply voltage generator 32G (signal amplification unit 323G). Subsequently, the power supply voltage generator 32G applies the power supply voltage $V_{14}$ having the constant amplitude $A_{14}$ to the heater resistor 141 and the double bridge circuit 31 (Step S24).

After Step S2G (S24), the heater resistance detector 33G calculates a detection value $V_{15}'$ and outputs the calculated value to the control unit 34G (Step S3G).

Specifically, Step S3G includes Steps S39G1 and S39G2 in addition to Step S31G similar to Step S31D described above in the third embodiment. Here, Step S31G is different from Step S31D only in that the description of the detection value of current detector 331 has been changed from the detection value $V_6$ to the detection value $V_{15}$ (=$A_{15}$ cos ωt).

After Step S31G, the switch 340 is turned on under the control of the control unit 34G (Step S39G1).

After Step S39G1, the fourth filter 341 uses a half-wave rectifier circuit, an integration circuit, and a low-pass filter (not illustrated) to smooth the detection value $V_{15}$ that has passed through the switch 340 in Step S39G1, and then outputs a detection value $V_{15}'$ (Step S39G2).

Although FIG. 53 illustrates the procedure in which Step S8 is executed after Step S3G for convenience of explanation, Step S3G and Step S8 are to be executed in parallel in practice.

After Step S8, the control unit 34G calculates the amplitude $A_{13}$ of the power supply voltage $V_{14}$ (=$A_{13}$ sin ωt) on the basis of the magnitude relationship determined in Step S8 and the deviation between the detection value $V_{15}'$ output from the heater resistance detector 33G and the target value "0" (Step S4G).

Step S4G includes Steps S41G S42G, S43B, S44G, and S45G similar to Steps S41D, S42D, S43B, S44D, and S45D in Step S4D described above in the third embodiment. Here, Step S41G is different from Step S41D only in that the comparison target with the target value "0" has been changed from the detection value $V_8$ to the detection value $V_{15}'$. Furthermore, Steps S42G, S44G, and S45G are different from Steps S42D, S44D, and S45D respectively only in that the change target has been changed from the amplitude $A_7$ to the amplitude $A_{13}$.

After Step S42G, Step S44G, or Step S45G, the treatment system 1G proceeds to Step S6. In Step S23 described above, the power supply voltage generator 32G applies the power supply voltage $V_{14}$ having the amplitude $A_{13}$ output from the control unit 34G in Step S42G, Step S44G, or Step S45G to the heater resistor 141 and the double bridge circuit 31.

The following is a description of an example of transitions, by the above-described heating control method, of the power supply voltage $V_{14}$, the detection value $V_{15}$ of the current detector 331 passing through the switch 340 (detection value $V_{15}$ input to the fourth filter 341), and the detection value $V_{15}'$ of the fourth filter 341.

Figure 56:
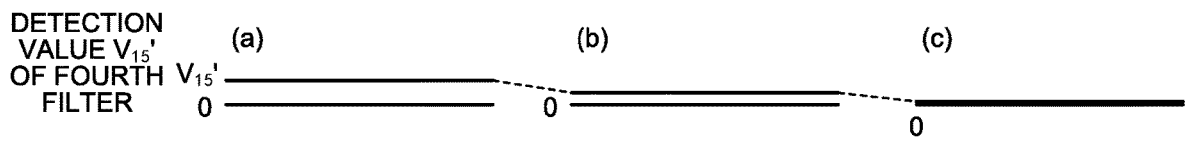
FIG. 56 is a diagram illustrating a transition of a detection value of the fourth filter.

FIG. 54 is a diagram illustrating a transition of the power supply voltage $V_{14}$. FIG. 55 is a diagram illustrating a transition of the detection value $V_{15}$ of the current detector 331 passing through the switch 340 (detection value $V_{15}$ input to the fourth filter 341). FIG. 56 is a diagram illustrating a transition of the detection value $V_{15}'$ of the fourth filter 341. Note that (a) of FIG. 54, (a) of FIG. 55, and (a) of FIG. 56 illustrate a case where the resistance value $R_x$ of the heater resistor 141 is sufficiently smaller than the target resistance value $R_x$t (a case where the heater temperature is sufficiently lower than the target temperature). (b) of FIG. 54, (b) of FIG. 55, and (b) of FIG. 56 illustrate a case where the resistance value $R_x$ of the heater resistor 141 approaches the target resistance value $R_x$t (a case where the heater temperature approaches the target temperature) as a result of heating control, compared with the states illustrated in (a) of FIG. 54, (a) of FIG. 55, and (a) of FIG. 56. (c) of FIG. 54, (c) of FIG. 55, and (c) of FIG. 56 illustrate a case where the resistance value $R_x$ of the heater resistor 141 matches the target resistance value $R_x$t (a case where the heater temperature matches the target temperature) as a result of heating control.

As observed in comparison between (a) and (b) of FIG. 54, in a case where the resistance value $R_x$ of the heater resistor 141 is smaller than the target resistance value $R_x$t (the heater temperature is lower than the target temperature, the power supply voltage $V_{14}$ is set such that the amplitude $A_{13}$ will be increased by the processes in Steps S45G and S23 in order to increase the resistance value $R_x$ of the heater resistor 141 (increase the heater temperature). In a case where the resistance value $R_x$ of the heater resistor 141 matches the target resistance value $R_x$t (in a case where the heater temperature matches the target temperature) as illustrated in (c) of FIG. 54, the power supply voltage $V_{14}$ is set to be maintained to have the amplitude $A_{13}$ ((b) of FIG. 54) of the power supply voltage $V_{14}$ in the immediately preceding loop (a loop including Steps S22 to S24, S3G, S8, S4G, and S6) by the processes in Steps S42G and S23.

As illustrated in (a) and (b) of FIG. 55, and (a) and (b) of FIG. 56, regarding the detection value $V_{15}$ of the current detector 331, each of the detection value $V_{15}$ after passing through the switch 340 and the detection value $V_{15}'$ obtained by smoothing the detection value $V_{15}$ approaches "0" as the resistance value $R_x$ of the heater resistor 141 approaches the target resistance value $R_x$t (as the heater temperature approaches the target temperature) by the processes of Step S45G and Step S23. Furthermore, as illustrated in (c) of FIG. 55 and (c) of FIG. 56, each of the detection value $V_{15}$ after passing through the switch 340 and the detection value $V_{15}'$ obtained by smoothing the detection value $V_{15}$ indicates "0" in a case where the resistance value $R_x$ of the heater resistor 141 matches the target resistance value $R_x$t (in a case where the heater temperature matches the target temperature).

Here, the detection value $V_{15}$ of the current detector 331 undergoes removal of the first current component according to the disclosure that changes with the amplitude modulation of the power supply voltage $V_{14}$, due to operation of the switch 340 (FIG. 55). Therefore, as observed in comparison of (a) to (c) of FIG. 54 with (a) to (c) of FIG. 55 or (a) to (c) of FIG. 56, the detection value $V_{15}$ after passing through the switch 340 and the detection value $V_{15}'$ obtained by smoothing the detection value $V_{15}$ would not change in accordance with the amplitude modulation of the power supply voltage $V_{14}$, but would change in accordance with the change in the heater temperature (change in the resistance value $R_x$ of the heater resistor 141). That is, the detection value $V_{15}$ after passing through the switch 340 and the detection value $V_{15}'$ obtained by smoothing the detection value $V_{15}$ correspond to the second current component according to the disclosure.

Even with the configuration of the fifth embodiment described above, effects similar to those in the first embodiment can be obtained.

Other Embodiments

Embodiments of the disclosure have been described hereinabove; however, the disclosure is not intended to be limited to the above-described first to fifth embodiments or their modifications 1-1 to 1-3, 2-1, 3-1 to 3-3.

In the above-described first to fifth embodiments and modifications 1-1 to 1-3, 2-1, and 3-1 to 3-3 described above, the second jaw 9 may be omitted.

In the first to fifth embodiments and the modifications 1-1 to 1-3, 2-1, and 3-1 to 3-3, it is allowable to have a configuration in which the second jaw 9 also includes the heat generating structure 12 and thermal energy is applied to living tissues from both the first and second jaws 8 and 9.

In the first to fifth embodiments and the modifications 1-1 to 1-3, 2-1 and 3-1 to 3-3, it is allowable to have a configuration in which high-frequency energy and ultrasonic energy are further applied, in addition to thermal energy, to the living tissues.

In the first to fifth embodiments and modifications 1-1 to 1-3, 2-1, and 3-1 to 3-3 described above, grasping surfaces of the heat transfer plate 13 and the opposing plate 16 that come into contact with the living tissue are formed with flat surfaces. However, the disclosure is not limited to this. For example, the cross-sectional shape of the grasping surface may be a protruding shape, a recessed shape, an inverted V-shape, or the like.

In the above-described second embodiment, the driving voltage according to the disclosure is a low-frequency AC voltage, and the detection voltage according to the disclosure is a high-frequency AC voltage. However, the disclosure is not limited to this. Conversely, the driving voltage according to the disclosure may be a high-frequency AC voltage, and the detection voltage according to the disclosure may be a low-frequency AC voltage.

Although the above-described fourth and fifth embodiments use a configuration in which amplitude modulation is performed on the power supply voltages $V_9$ and $V_{14}$, the disclosure is not limited to this, and it is allowable to use a configuration in which pulse width modulation is performed.

The above-described first to fifth embodiments and modifications 1-1 to 1-3, 2-1, and 3-1 to 3-3 uses a configuration in which the control units 34, 34A to 34G stop operation of the power supply voltage generators 32, 32A to 32E, 32G in a case where it is judged that elapsed time after starting heating control has passed a predetermined time (Steps S6 and S7). However, the disclosure is not limited to this configuration. For example, it is allowable to use a configuration in which the application of the power supply voltage $V_1$, $V_3$, $V_5$, $V_9$, and $V_{14}$ to the heater resistor 141 and the double bridge circuit 31 is continued while the foot switch 4 is on and the operation of the power supply voltage generators 32, 32A to 32E, and 32G is to be stopped when the foot switch 4 is turned off.

The above-described second to fifth embodiments and modifications 2-1, 3-1 to 3-3 use a configuration in which the phase difference between the voltage waveforms W1 and W2 at the intermediate point P1 or the intermediate point P2 and the voltage waveform W3 at the point P3 is used for the determination of the magnitude relationship between the resistance value $R_x$ of the heater resistor 141 and the target resistance value $R_x t$ ($R_x < R_x t$ or $R_x > R_x t$). However, the disclosure is not limited to this configuration. For example, it is allowable to use a configuration in which a voltage waveform between the intermediate point P1 and the point P3 and a voltage waveform between the intermediate point P2 and the point P3 are individually obtained, and the magnitude relationship between the resistance value $R_x$ of the heater resistor 141 and the target resistance value $R_x t$ ($R_x < R_x t$ or $R_x > R_x t$) is determined using the magnitude relationship between the obtained voltage waveforms.

In the above-described second to fifth embodiments and modifications 2-1 and 3-1 to 3-3, a polarity determination unit having a function different from that of the polarity determination unit 35 may be employed.

Figure 57:
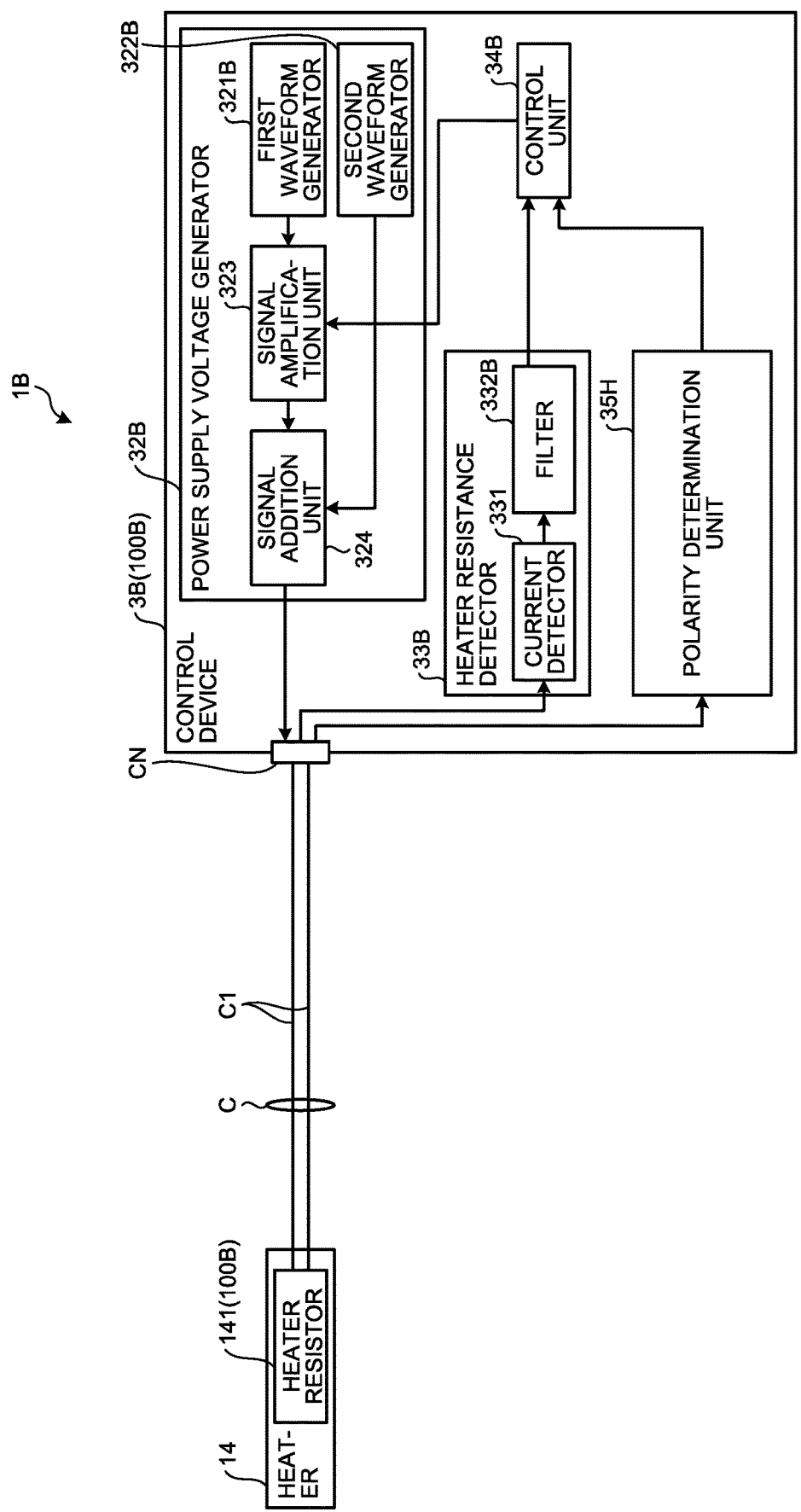
FIG. 57 is a diagram illustrating an example of another polarity determination unit.
Figure 58:
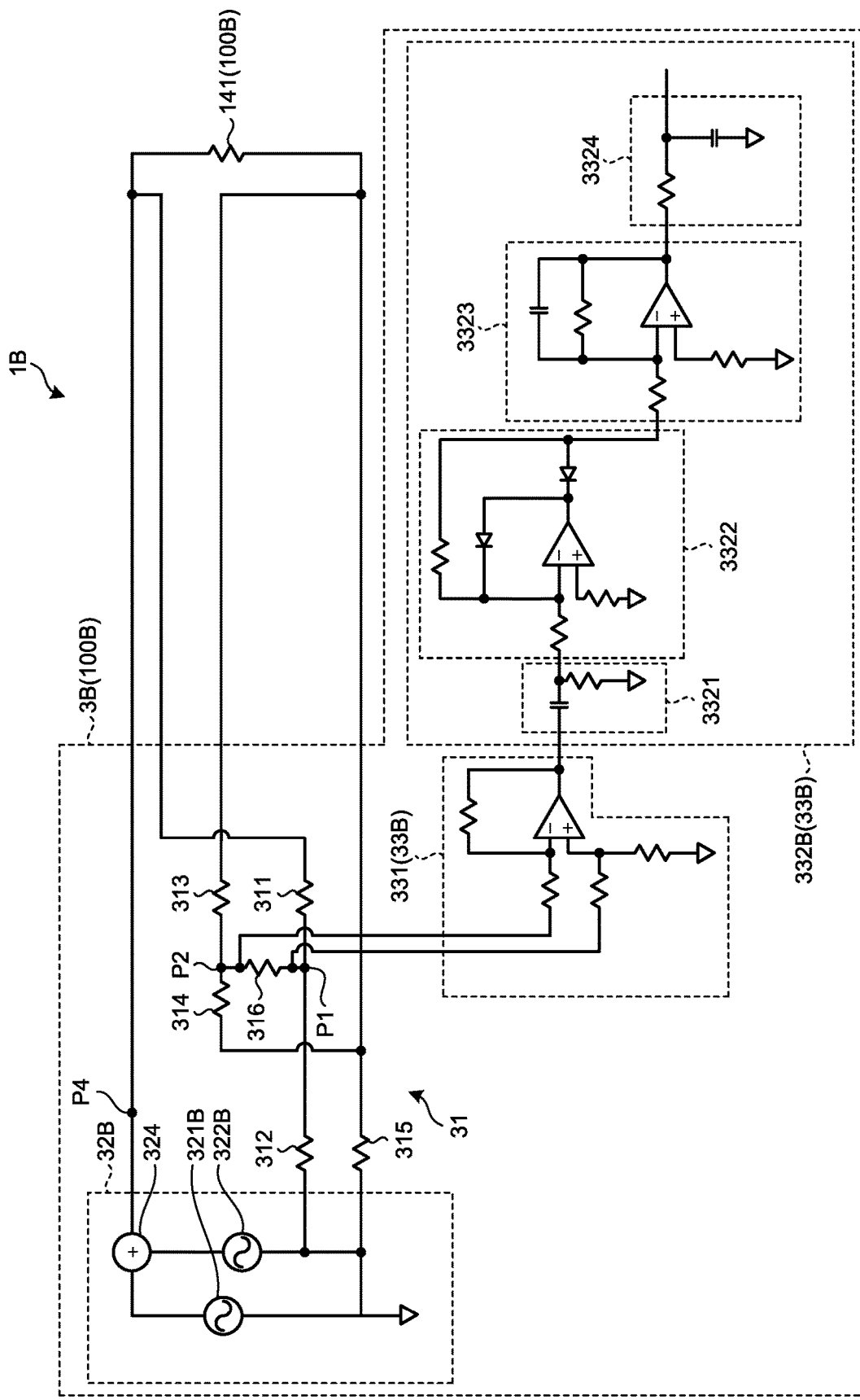
FIG. 58 is a diagram illustrating an example of another polarity determination unit.

FIGS. 57 and 58 are diagrams illustrating an example of another polarity determination unit 35H. FIGS. 57 and 58 illustrate a case where the polarity determination unit 35H is applied to the treatment system 1B according to the second embodiment described above for convenience of explanation.

The polarity determination unit 35H (FIG. 57) detects each of the voltage at a point P4 (FIG. 58) and the current flowing through the third auxiliary ratio arm resistor 315 and calculates a resistance value $R_{prev}$. Furthermore, when a certain time (for example, 50 msec) has passed after the calculation, the polarity determination unit 35H detects the voltage at the point P4 and the current flowing through the third auxiliary ratio arm resistor 315 again, and calculates a resistance value $R_{next}$. Subsequently, the polarity determination unit 35H calculates a difference ($R_{next} - R_{prev}$) between the resistance value $R_{next}$ and the resistance value $R_{prev}$, and then outputs the calculation result to the control unit 34B.

Here, in a case where the resistance value $R_x$ of the heater resistor 141 is smaller than the target resistance value $R_x t$ ($R_x < R_x t$), the difference ($R_{next} - R_{prev}$) between the resistance value $R_{next}$ and the resistance value $R_{prev}$ is obtained as a positive value. Therefore, in a case where the polarity determination unit 35H has output the positive difference ($R_{next} - R_{prev}$), the control unit 34B determines that the resistance value $R_x$ of the heater resistor 141 is smaller than the target resistance value $R_x t$ ($R_x < R_x t$).

In contrast, in a case where the resistance value $R_x$ of the heater resistor 141 is greater than the target resistance value $R_x t$ ($R_x > R_x t$), the difference ($R_{next} - R_{prev}$) between the resistance value $R_{next}$ and the resistance value $R_{prev}$ is obtained as a negative value. Therefore, in a case where the polarity determination unit 35H has output the difference ($R_{next} - R_{prev}$), being a negative value, the control unit 34B determines that the resistance value $R_x$ of the heater resistor 141 is greater than the target resistance value $R_x t$ ($R_x > R_x t$).

The heating device, the treatment system, and the heating control method according to the disclosure have an effect that the heater temperature can be controlled to the target temperature with high accuracy.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system comprising:
   a first jaw;
   a second jaw, the first jaw and the second jaw confirmed to grasp a living tissue;
   a heater resistor provided on the first jaw, the heater resistor configured to generate heat by energization; and
   a control device including:
      a double bridge circuit having a detection resistor electrically connected to the heater resistor, the double bridge circuit configured to allow current to flow through the detection resistor when the detection resistor detects a difference between a resistance value of the heater resistor and a predetermined target resistance value, a power supply voltage generator configured to generate a power supply voltage to be applied to the heater resistor and the double bridge circuit,
a controller configured to modulate the power supply voltage, and
a heater resistance detector configured to detect the current flowing through the detection resistor.

2. The treatment system according to claim 1, wherein:
the power supply voltage generator is configured to generate the power supply voltage by superimposing a driving power supply voltage having a first frequency and a detection power supply voltage, the driving power supply voltage having a first frequency, the detection power supply voltage having a second frequency different from the first frequency,
the heater resistance detector includes:
a current detector configured to detect the current flowing through the detection resistor; and
a filter configured to remove a component of the first frequency from a detection value obtained by the current detector and extract a component of the second frequency,
the heater resistance detector is configured to detect an alternating-current (AC) component, which is different than a direct current (DC) component, from the current flowing through the detection resistor, the DC component changing in accordance with a modulation of the power supply voltage, the AC component changing in accordance with a temperature change of the heater resistor, and
the controller is configured to modulate the power supply voltage based on the AC component.

3. The treatment system according to claim 2, wherein:
the driving power supply voltage is an alternating-current (AC) voltage,
the detection power supply voltage is a direct-current (DC) voltage, and
the controller is configured to modulate the driving power supply voltage from the driving power supply voltage and the detection power supply voltage.

4. The treatment system according to claim 2, wherein:
each of the driving power supply voltage and the detection power supply voltage is an alternating-current (AC) voltage, and
the controller is configured to modulate the driving power supply voltage.

5. The treatment system according to claim 1, wherein the heater resistance detector includes:
a current detector configured to detect the current flowing through the detection resistor; and
a voltage detector configured to detect a power supply voltage, the voltage detector configured to detect based on a detection value obtained by each of the current detector and the voltage detector.

6. The treatment system according to claim 5, wherein the heater resistance detector further includes a division circuit configured to calculate a current component by dividing a first detection value by a second detection value, the first detection value obtained by the current detector, the second detection value obtained by the voltage detector.

7. The treatment system according to claim 5, wherein:
the heater resistance detector further includes:
a pulse width modulation circuit configured to generate a switch control signal by performing pulse width modulation on a detection value obtained by the voltage detector, and
a switch configured to switch to control outputting of a detection value obtained by the current detector based on the generated switch control signal, and
the heater resistance detector is configured to detect the current component based on a detection value output from the switch.

8. The treatment system according to claim 1, wherein:
the power supply voltage generator is configured to sequentially apply a driving power supply voltage and a detection power supply voltage as the power supply voltage to the heater resistor and the double bridge circuit,
the controller is configured to modulate only the driving power supply voltage based on the current component, and
the heater resistance detector is configured to detect a current flowing through the detection resistor as the current component when the detection power supply voltage is applied to the heater resistor and the double bridge circuit.

9. The treatment system according to claim 1, wherein the controller is configured to perform one of amplitude modulation and pulse width modulation on the power supply voltage.

10. A heating control method comprising:
applying a power supply voltage to a heater resistor generating heat by energization and a double bridge circuit having a detection resistor connected to the heater resistor, the double bridge circuit configured to allow a current to flow through the detection resistor wherein the detection resistor detects a difference between a resistance value of the heater resistor and a predetermined target resistance value;
modulating the applied power supply voltage; and
detecting the current flowing through the detection resistor.

11. A control device comprising:
a double bridge circuit having a detection resistor configured to be electrically connected to a heater resistor configured to generate heat by energization, the double bridge circuit configured to allow a current to flow through the detection resistor when the detection resistor detects a difference between a resistance value of the heater resistor and a predetermined target resistance value;
a power supply voltage generator configured to generate a power supply voltage to be applied to the heater resistor and the double bridge circuit;
a controller configured to modulate the generated power supply voltage; and
a heater resistance detector configured to detect the current flowing through the detection resistor.

12. A heating device comprising:
the heater resistor according to claim 11; and
the control device according to claim 11;
wherein a heater resistance detector is configured to detect an alternating-current (AC) component, which is different than a direct current (DC) component, from the current flowing through the detection resistor, the DC component changing in accordance with a modulation of the power supply voltage, the AC component changing in accordance with a temperature change of the heater resistor, the controller being configured to modulate the power supply voltage based on the AC component.

13. The control device according to claim 11, wherein the controller is configured to:
    determine magnitude relationship between the resistance value of the heater resistor and the target resistance value; and
    change an amplitude of the power supply voltage based on the magnitude relationship.

14. The control device according to claim 13, wherein the controller is configured to maintain the amplitude of the power supply voltage when the resistance value is equal to the target resistance value.

15. The control device according to claim 13, wherein the controller is configured to increase the amplitude of the power supply voltage when the resistance value is smaller than the target resistance value or the resistance value is equal to the target resistance value.

16. The control device according to claim 13, wherein the controller is configured to decrease the amplitude of the power supply voltage when the resistance value is larger than the target resistance value.

17. The treatment system according to claim 1, wherein the controller is configured to:
    determine magnitude relationship between the resistance value of the heater resistor and the target resistance value; and
    change an amplitude of the power supply voltage based on the magnitude relationship.

18. The treatment system according to claim 17, wherein the controller is configured to maintain the amplitude of the power supply voltage when the resistance value is equal to the target resistance value.

19. The treatment system according to claim 17, wherein the controller is configured to increase the amplitude of the power supply voltage when the resistance value is smaller than the target resistance value or the resistance value is equal to the target resistance value.

20. The treatment system according to claim 17, wherein the controller is configured to decrease the amplitude of the power supply voltage when the resistance value is larger than the target resistance value.

* * * * *